(12) United States Patent
Monif

(10) Patent No.: US 9,128,098 B2
(45) Date of Patent: Sep. 8, 2015

(54) FUIDI HERD MANAGEMENT AND RISK STRATIFICATION METHODS

(71) Applicant: Gilles R. G. Monif, Bellevue, NE (US)

(72) Inventor: Gilles R. G. Monif, Bellevue, NE (US)

(*) Notice: Subject to any disclaimer, the term of this patent is extended or adjusted under 35 U.S.C. 154(b) by 119 days.

(21) Appl. No.: 13/690,530

(22) Filed: Nov. 30, 2012

(65) Prior Publication Data

US 2014/0116352 A1 May 1, 2014

Related U.S. Application Data

(63) Continuation-in-part of application No. 13/665,576, filed on Oct. 31, 2012, now abandoned.

(51) Int. Cl.
| | | |
|---|---|---|
| *C12Q 1/68* | (2006.01) | |
| *G01N 33/68* | (2006.01) | |
| *G01N 33/569* | (2006.01) | |

(52) U.S. Cl.
CPC ............ *G01N 33/6854* (2013.01); *C12Q 1/686* (2013.01); *C12Q 1/689* (2013.01); *G01N 33/5695* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 4,965,188 A | 10/1990 | Mullis et al. | |
| 5,628,994 A | 5/1997 | Kaper et al. | |
| 5,861,163 A | 1/1999 | Kim et al. | |
| 6,277,580 B1 | 8/2001 | Ellingson et al. | |
| 6,833,135 B1 | 12/2004 | Frazao Moniz Pereira et al. | |
| 7,422,869 B2 | 9/2008 | Eda et al. | |
| 7,476,530 B1 | 1/2009 | Monif | |
| 8,008,033 B2 | 8/2011 | Monif | |
| 8,143,012 B2 | 3/2012 | Monif | |
| 8,361,737 B2 | 1/2013 | Monif | |
| 2002/0064861 A1 | 5/2002 | Barletta et al. | |
| 2003/0044431 A1 | 3/2003 | Schurig et al. | |
| 2003/0092080 A1 | 5/2003 | Braun et al. | |
| 2004/0109875 A1 | 6/2004 | Kernodle et al. | |
| 2005/0058663 A1 | 3/2005 | Monif | |
| 2005/0232937 A1 | 10/2005 | Willemsen et al. | |
| 2005/0250120 A1 | 11/2005 | Cole et al. | |
| 2007/0042383 A1 | 2/2007 | Kapur et al. | |
| 2007/0134274 A1 | 6/2007 | Talaat | |
| 2007/0134708 A1 | 6/2007 | Talaat et al. | |
| 2007/0202131 A1 | 8/2007 | Jacobs, Jr. et al. | |
| 2010/0021897 A1 | 1/2010 | Williams et al. | |
| 2012/0171689 A1 | 7/2012 | Monif | |

FOREIGN PATENT DOCUMENTS

| | | |
|---|---|---|
| EP | 1 223 225 A1 | 7/2002 |
| JP | 2005-95101 A | 4/2005 |
| WO | WO-03/058248 A2 | 7/2003 |
| WO | WO-2004/000878 A1 | 12/2003 |
| WO | WO-2008/033806 A1 | 3/2008 |

OTHER PUBLICATIONS

Monif, Grg and Williams, JE, "The Significance of a Negative Map ELISA Test for Mycobacterium Avium Subspecies Paratuberculosis" *Journal of Applied Research in Veterinary Medicine*, 2013, 11(2):117-122.

Gilmour, NJL et al., "Experimental Oral Infection of Calves with Mycobacterium Johnei" J. Comp. Path., 1965, 75:281-286.

Harris, NB and Barletta, RG, "Mycobacterium avium subsp. paratuberculosis in Veterinary Medicine" *Clinical Microbiology Reviews*, 2001, 14(3):489-512.

Reddacliff, LA and Whittington, RJ, "Experimental infection of weaner sheep with S strain Mycobacterium avium subsp. paratuberculosis" *Veterinary Microbiology*, 2003, 96:247-258.

Sangari, FJ et al., "Mycobacterium avium Invades the Intestinal Mucosa Primarily by Interacting with Enterocytes" *Infection and Immunity*, 2001, 69(3):1515-1520.

Schleig, PM et al., "Attachment of Mycobacterium avium subspecies paratuberculosis to bovine intestinal organ cultures: Method development and strain differences" *Veterinary Microbiology*, 2005, 108:271-279.

Secott, TE et al., "Fibronectin Attachment Protein Homologue Mediates Fibronectin Binding by *Mycobacterium avium* subsp. *paratuberculosis*" American Society for Microbiology, 2001, 69(4):2075-2082.

Secott, TE et al., "Fibronectin Attachment Protein Is Necessary for Efficient Attachment and Invasion of Epithelial Cells by Mycobacterium avium subsp paratuberculosis" *Infection and Immunity*, 2002, 70(5):2670-2675.

Stabel, JR "Production of γ-Interferon by Peripheral Blood Mononuclear Cells: An Important Diagnostic Tool for Detection of Subclinical Paratuberculosis" *Journal of Veterinary Diagnostic Investigation*, 1996, 8:345-350.

(Continued)

*Primary Examiner* — Jennifer Graser
(74) *Attorney, Agent, or Firm* — Saliwanchik, Lloyd & Eisenschenk

(57) ABSTRACT

The invention concerns the detection of pathogenic *mycobacterium* comprising *Mycobacterium avium* subsp. *paratuberculosis* (Map) and genomic variants in a bulk milk sample, and more particularly a method for herd management that stratifies the risk of bulk tank milk lots derived from diagnostic-tested subgroups potentially containing DNA from pathogenic *mycobacterium* including Map. The method involves creating defined risk groups (categories) of milk-producing animals, such as dairy cows, for the presence of Map or related genomic variants in their milk. Another aspect of the invention concerns a method to strengthen the ability of milk-producing animals to resist environmental challenges by Map based on identifying those animals that have and maintain a low antibody level to Map using their female progeny as replacement animals.

20 Claims, 6 Drawing Sheets

(56) References Cited

OTHER PUBLICATIONS

Eiichi M. "Epidemiological situation and control strategies for paratuberculosis in Japan" *Japanese Journal of Veterinary Research*, 2012; 60: 19s-29s.

Naser, S.A. et al. "Culture of Mycobacterium avium subspecies paratuberculosis (MAP) from the Blood of Patients with Crohn's disease: A Follow-Up Blind Multi Center Investigation" *The Open Inflammation Journal*, 2009, 2:22-23.

Web site (temporary) idi.lpdesignsomaha.com: after Nov. 1, 2009, info@infectiousdiseasesincorporated.com.

Monif, G. et aL, "The natural history of Mycobacterium avium subspeciesn paratuberculosis as interpreted by the FUIDI #2 Map Test" 10*th* *International Colloquim on Paratuberculosis*, Minneapolis, MN, Aug. 9-14, 2009, p. 111.

Monif, G. "The FUIDI Herd Management Schema" 10*th* *International Colloquim on Paratuberculosis*, Minneapolis, MN, Aug. 9-14, 2009, p. 141.

Dorshorst, N. C. et al. "Decision analysis model for paratuberculosis control in commercial dairy herds" *Preventive Veterinary Medicine*, 2006, 75:92-122.

Collins, M. et al. "Evaluation of Five Antibody Detection Tests for Diagnosis of Bovine Paratuberculosis" *Clinical and Diagnostic Laboratory Immunology*, Jun. 2005, 12(6)685-692.

Williams, M. et at., The Paratuberculosis Newsletter, Mar. 2008, pp. 1, 2, 7, 8 and 9.

NCBI GenBank Accession No. U16276, May 11, 2005, pp. 1-2.

NCBI GenBank Accession No. X70277, Jun. 24, 1993, p. 1.

NCBI GenBank Accession No. AF286339, May 11, 2005, pp. 1-2.

Lowe et al. 1990. A computer program for selection of oligonucleotide primers for polymerase chain reactions. *Nucleic Acid Research*, 18(7):1757-1761.

The nucleic acid sequences search reports (AC: AQY98577) for SEQID Nos. 5, 8-10 and 38-40, 2005.

*retest individually at any time if diarrhea or reduced lactation occur

*retest individually at any time if diarrhea or reduced lactation occur

*retest individually at any time if diarrhea or reduced lactation occur

FUIDI HERD MANAGEMENT AND RISK STRATIFICATION METHODS

CROSS-REFERENCE TO RELATED APPLICATION

The present application is a continuation-in-part of U.S. patent application Ser. No. 13/665,576, filed Oct. 31, 2012, now abandoned, and which is hereby incorporated by reference herein in its entirety, including any figures, tables, nucleic acid sequences, amino acid sequences, and drawings.

The Sequence Listing for this application is labeled "Seq-List-replace" which was created on Dec. 24, 2014 and is 63 KB. The entire contents of the sequence listing are incorporated herein by reference in their entirety.

BACKGROUND OF THE INVENTION

*Paratuberculosis* (Johne's disease) is caused by *Mycobacterium avium* subsp. *paratuberculosis* (Map), a facultative intracellular, acid-fast bacillus, and affects ruminants worldwide. In the United States, the disease causes the industry economic losses estimated at $200 and 250 million. The control of the disease is hampered by ineffective diagnostic methods, particularly in detection of sub-clinically infected animals.

A segment of infected animals in a given herd can be presumptively diagnosed based on clinical signs of diarrhea, emaciation, and/or serology. The animals can be reliably diagnosed with conventional and/or radiometric fecal culture. Detection of sub-clinically infected animals by serological and culture testing frequently leads to false negative results. Producers depend on "test-and-cull" programs to control the disease.

Several methods for screening for the presence of Map in tissue samples from affected animals are known. Commonly used immunological methods for detecting Map in a sample include agar gel immunodiffusion (AGID) tests and ELISA assays. More rapid DNA-based tests have been developed that utilize PCR in conjunction with pairs of primers that specifically detect species-specific insertion sequences present in Map strains, but not in other strains of *Mycobacterium avium* complex. A commercial DNA-based assay is available for detecting a 413 bp PCR product amplified from the Map insertion sequence defined as IS900 (Vary, P. H. et al., *J Clin Microbiol* 1990; 28:933-937, which is incorporated herein by reference in its entirety). When applied to the testing of milk for the detection of DNA of Map, the IS900-based PCR primers in commercial use do not identify the DNA of related pathogenic *mycobacterium*. To more completely prevent pathogenic mycobacteria from entering the human food supply through milk and milk-base products, the PCR primers used to evaluate milk for pathogenic mycobacteria would need to be more inclusive.

The current "gold standard" method for diagnosis of sub-clinical Map infection has been based upon fecal recovery of live Map using artificial culture media. Beckton-Dickinson Biosciences has recently developed an automated system (BACTEC MGIT 960 system) that can be used as a fully automated diagnostic tool for Johne's disease. Although this technique is highly specific, it is still suboptimal in terms of sensitivity. Additionally, culture from a fecal sample is only deemed negative after 49 days. This, however, is an imperfect diagnosis because cultures may become positive as long as six months after inoculation. In very rare instances, cultures have been reputed to become positive between six months and one year. Due to the amount of time a sample must be cultured, the expense of the specialized culture reagents and the BACTEC MGIT 960 system, this test is expensive. The cost to process a single sample ranges from $16.00 to $45.00 (depending upon the degree to which a given state subsidizes testing costs).

Map is not killed by pasteurization (1, 2). Viable Map and genomic variants enter the human food chain through milk and milk products. *Mycobacterium avium* subspecies *paratuberculosis* can be cultured from milk and selected cheeses (3-5) and constitutes the primary means by which Map and other pathogenic enteric *mycobacterium* enter into the human food supply.

Current testing using IS900 Map ELISA tests fail to identify up to one-third of cows shedding Map into their milk; Pinedo et al. found that 23.5% of cows with Map identified in their milk were deemed serologically negative for Map infection by IS900 ELISA Map tests. Another 11.8% had but a suspicious antibody titer (6). Wisziewska-Laszcych et al confirmed this initial report (7). The National Animal Health Monitoring System Study of 515 dairy farms demonstrated the presence of Map DNA in the bulk tank samples from 31.2% if the participating dairy farms.

In June 2001, the United Kingdom Food Standard Agency issued its report for food standards. The conclusion statement states "There is undoubtedly sufficient cause for concern (relative to Map as being the cause of Crohn's disease) for further action to be taken urgently to determine what the available data means . . . . This question can be divided into two areas: What action should be taken to reduce exposure to Map even though the causal link is not established; and what action can be taken to increase the knowledge base so that future decisions may be based upon more information (8)."

In 2008, the American Academy of Microbiologists published its report on *Mycobacterium avium paratuberculosis*: Infrequent human pathogen or public health threat (9). The executive summary states, "the association of MAP and CD is no longer in question. The critical issue today is not whether MAP is associated with CD, but whether MAP causes CD or is only incidentally present."

By 2008, the majority of Koch's postulates for causation that can be ethically addressed had been effectively met (10-16). In 2009, three independent diagnostic laboratories (Michael T. Collins, Saleh A. Naser, and that of the Centers for Disease Control and Prevention) recovered Map from the blood of individuals with Crohn's disease (17). These three laboratories reaffirm the validity of Naser's previous recovery of Map from the blood of Crohn's patients as well as from the breast milk of two postpartum CD females without corresponding recovery from non-Crohn's diseased individuals.

From a medical infectious disease point of view, the validation of Naser's original findings cuts short the argument as to causality. If an individual has certain retroviruses in his or her white blood cells, he or she has HIV infection. If the individual has hepatitis B or C virus in his or her white blood cells, he or she has hepatitis infection. If an individual has Map in his or her white blood cells, he or she has infection with Map.

The natural history of Map infection/disease presumes a progressive three stage development. Classically, the pathogenesis of Johne's disease has been viewed as the progressive culmination of three stages of microbial involvement of the host animal Initial infection has been postulated to be acquired early and remain latent with or without intermittent evidence of fecal shedding until such time as serological evidence of infection can be detected (subclinical disease). Thereafter, the animals experience a progressive, chronic granulomatous infection that culminates in Johne's disease (17-18). What has been delineated in the literature is the progressive development of disease. The pathogenesis of Map induced disease is not the natural history of Map infection.

In developing the pathogenesis of Johne's disease in herbivores, three basic assumptions were made:
1. that *Mycobacterium avium* subspecies *paratuberculosis* (Map) is the cause, and not a cause, of Johne's disease;
2. that the IS900 insertion sequence is unique to Map isolates; and
3. that *Mycobacterium avium* complex (Mac) that includes *Mycobacterium avium* subsp. *avium* and *M. hominissuis* are environment and not pathogenic *mycobacterium*.

*Mycobacterium avium* subspecies *paratuberculosis* (Map) is theorized to have evolved from *Mycobacterium avium* subsp. *avium* (Ma) (17-20). Map and Ma, by genetic criteria, are classified as subsets of the same species (20, 21). The literature on Johne's disease (chronic granulomatous enteritis in cattle) tends to deny the existence of pathogenic Map phenotypic variants more closely related to MA than to Map and that some *mycobacterium* are more Ma-like than Map-like (24-26). Genomic polymorphism is to be anticipated within species evolution. Such isolates are not identified by IS900 PCR primers. Darcel and Logen-Handsame have postulated that the failure of commercial Map ELISA tests to identify all clinically ill animals has been due to a lack of representation of the entire range of immunodominant test antigens (26).

IS1311 is present in Ma/Mac as well as Map. Primers based upon the IS1311 insertion sequence that identify Ma variants and Map are encompassed in the direct and nested fecal FecaMap® patented primers. The IS1311 insertion sequence is present in the vast majority of pathogenic *mycobacterium*. A long evolutionary time span is suggested by the presence of mutations in some of the IS1311 elements (17). None of the commercial Map ELISA tests including FUID#1 Map ELISA test have an antigen spectrum that identifies all potential pathogenic *mycobacterium*.

A large Danish study demonstrated that declines in milk production attributable to Map occur over a long period of time and may not be realized without more advanced management tools (27).

BRIEF SUMMARY OF THE INVENTION

The inventor has made the following important observations:
1. Map and genomic variants are embedded in the herbivore food chain;
2. highly infected animals are the disseminators of infection, but not the ultimate reservoir of infection;
3. virtually every cow in a large confined herd will eventually become infected with Map and/or its genomic variants;
4. the vast majority of infected animals obtain immune governance over *mycobacterium* replication;
5. in selected animals, immune governance can be overcome due to parturition and either added nutritional or environmental stress; and
6. long-term utilization of the FUIDI system and retention of selective heifers born to mothers that have demonstrate the ability to handle their infection will result in a herd with enhanced genetic ability to withstand occasional environmental challenges.

Current USDA sanctioned tests identify a titer of *Mycobacterium avium* subsp. *paratuberculosis* (Map) antibody chosen to protect the manufacturers from a false-positive test result. However, neither the Map ELISA manufacturers nor USDA have publically defined the significance of a "negative" Map test.

The natural history of Map infection has been constructed on limited serological data and relatively insensitive *mycobacterium* culture isolation technology. The present invention is based, at least in part, upon tests that (1) identify animals that have had significant antigenic exposure to Map at some time and (2) assess the probability of active *mycobacterium* replication (e.g., the FUIDI Map ELISA tests), and their resultant application in an epidemiological field trial. In dairies, milk is collected from a number of cows through a milking system and directed to a bulk milk tank for storage until the milk is transported off site. As indicated above, none of the commercial Map ELISA tests, including the FUID#1 Map ELISA test, have an antigen spectrum that identifies all potential pathogenic *mycobacterium*. By using IS1311 primers (Genbank accession # U16276) to test bulk tank milk, a second level of screening is introduced that identifies polymorphic genomic variants not identified by IS900 primers.

One aspect of the invention concerns a method of detecting the presence of Map and other pathogenic *mycobacterium* in a bulk milk sample obtained from a volume of milk from a plurality of milk-producing animals, comprising determining the presence of the Map IS1311 insertion sequence (Genbank accession # U16276) in the bulk milk sample.

Another aspect of the invention concerns a method for herd animal management that stratifies the risk of bulk tank milk lots derived from diagnostic-tested subgroups potentially containing DNA from pathogenic *mycobacterium* comprising Map, the method comprising:
(a) determining the level of Map-specific antibodies in blood samples from individual milk-producing animals, wherein said determining comprises:
  (i) conducting a first test that identifies whether the animals have had antigenic exposure to Map; and
  (ii) conducting a second test that assesses the probability of an animal with demonstrable anti-Map antibodies having ongoing active Map replication;
(b) categorizing the animals into a plurality of categories based, at least in part, on the results of the first and second tests; and
(c) detecting the presence of Map in a bulk milk sample obtained from a volume of milk from a plurality of animals in each category by determining the presence of the Map IS1311 insertion sequence (Genbank accession # U16276) in the bulk milk sample. In some embodiments, the animals are categorized, and preferably separated, into five categories (also referred to herein as groups).

Another aspect of the invention concerns a method to strengthen the ability of milk-producing animals to resist environmental challenges by pathogenic *mycobacterium* comprising Map, the method comprising:
(a) identifying milk-producing animals that have a low antibody level to Map (anti-Map antibody level);
(b) serially monitoring the level of anti-Map antibodies in the identified animals;
(c) retaining female animals that maintain a low anti-Map antibody level; and
(d) incorporating female animals born to mothers that maintain a low-anti-Map antibody level into a herd as replacement animals to replace female animals taken out of milk production.

BRIEF DESCRIPTION OF THE SEQUENCES

Figure 1A:
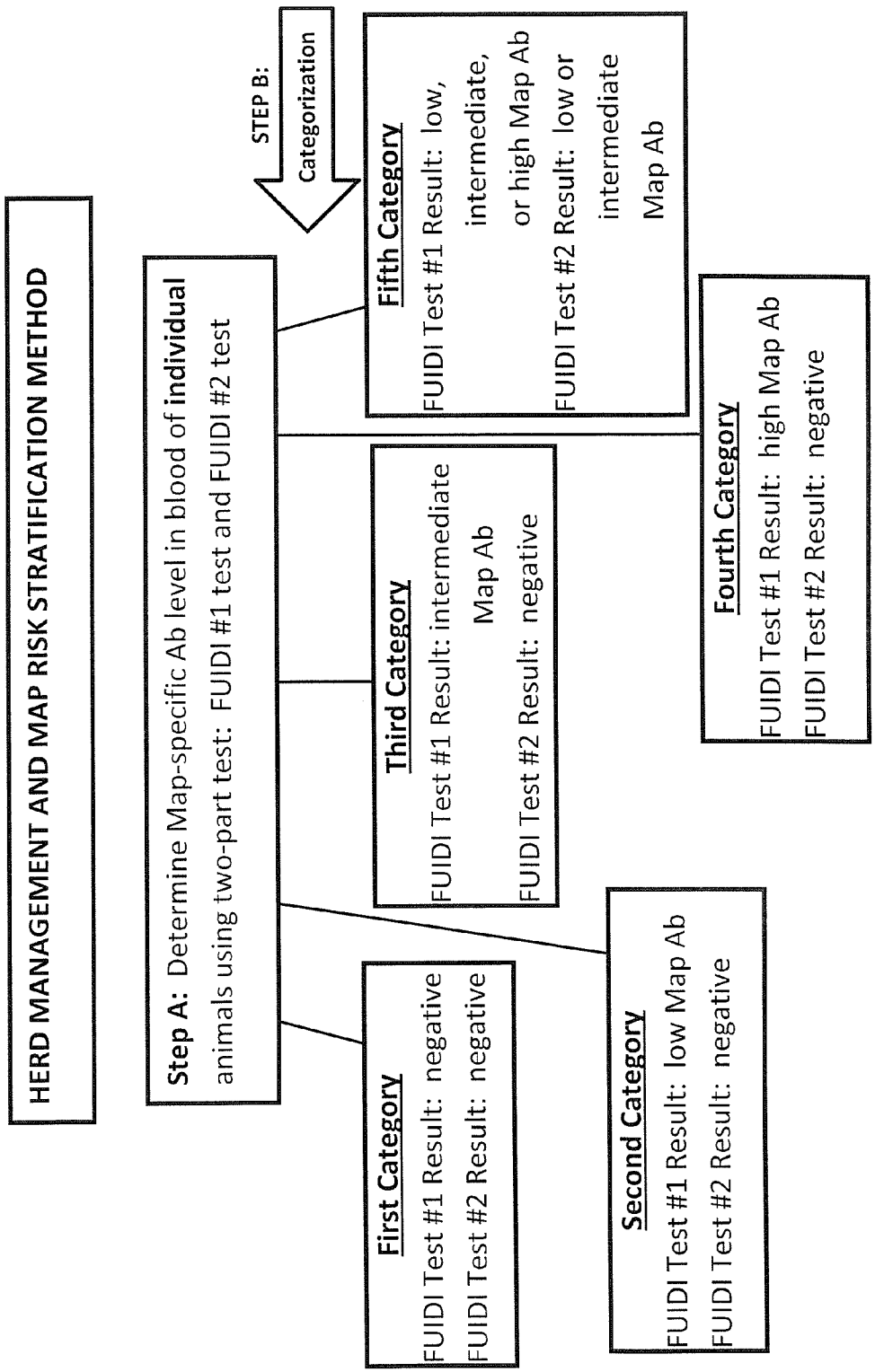
FIGS. 1A-1F show an embodiment of the herd management and Map Risk Stratification Method of the invention, including blood testing of individual animals with FUIDI test #1 and FUIDI test #2 (Step A) and categorization (Step B) (FIG. 1A), and bulk milk testing of each category of animals (Step C) with subsequent monitoring regimens (FIGS. 1B-1F).

SEQ ID NOs: 1-4 are primers suitable for use in PCR techniques for the identification of MAP in biological samples. Primers IS1 (CGA TTT ATC AGG CAC TCA TCG) (SEQ ID NO:1) and IS2 (CAA ATA GGC CTC CAT CAC CA) recognize a 242 base pair sequence of Map IS1311 and primers IS3 (ATG AAC GGA GCG CAT CAC) and IS4 (CGA CCG AAG CTT GGG AAT) overlap and span a 104 base pair region within the Map IS1311 insertion sequence.

SEQ ID NO: 5 is the complete cds sequence of *Mycobacterium avium* subsp. *paratuberculosis* (Map) and *Mycobacterium avium* subsp. *avium* (MAA) insertion sequence IS1311 transposase gene.

SEQ ID NO: 6 is the amino acid sequence of the MAP and MAA insertion sequence IS1311 transposase.

SEQ ID NO: 7 is the nucleotide sequence the *Mycobacterium avium* insertion sequence ISMav2 derived from the MAP genome project.

SEQ ID NOs: 8-212 are primer and probe sequences suitable for use in PCR techniques for the identification of MAP in biological samples.

SEQ ID NO: 213 is the nucleotide sequence of the *Mycobacterium avium* sequence F57.

DETAILED DISCLOSURE OF THE INVENTION

U.S. Pat. No. 8,143,012 (Monif; entitled Fuidi Herd Management Schema), U.S. Pat. No. 8,008,033 (Monif; entitled Fuidi Herd Management Schema), U.S. Pat. No. 7,476,530 (Monif; entitled *Mycobacterium avium* subspecies *paratuberculosis* oral vaccine and methods), and U.S. Patent Application Publication No. 2010/0021897 (Williams et al.; entitled *Mycobacterium Avium* Subspecies *Paratuberculosis* (Map) Diagnostic Test) are each incorporated herein by reference in their entireties.

The methods of the invention concern herd management and stratification of risk associated with Map infection (Map and MAP are used interchangeably herein to refer to *Mycobacterium avium* subspecies *paratuberculosis*). The methods of the invention can facilitate the reduction of the amount of Map entering the human food supply. The key to preservation of the dairy industry resides in keeping in production infected dairy cows that posse a minimal risk to contaminating their biological fluids.

One aspect of the invention concerns a method for herd animal management that stratifies the risk of bulk tank milk lots derived from diagnostic-tested subgroups potentially containing DNA from pathogenic *mycobacterium* comprising Map, the method comprising:

(a) determining the level of a Map-specific antibodies in blood samples from individual milk-producing animals, wherein said determining comprises:
   (i) conducting a first test that identifies if animals have had antigenic exposure to Map; and
   (ii) conducting a second test that assesses the probability of active Map replication in the animals;
(b) categorizing the animals into a plurality of categories based, at least in part, on the results of the first and second tests; and (c) detecting the presence of Map in a bulk milk sample obtained from a volume of milk from a plurality of animals in each category by determining the presence of the Map IS1311 insertion sequence (Genbank accession # U16276) in the bulk milk sample.

The terms "bulk milk sample" and "bulk tank milk sample" (BTM sample) are used interchangeably herein to refer to samples of pooled milk (milk from a plurality of animals, such as from a bulk tank, but not necessarily from a bulk tank). For milking groups that are too small to produce bulk tank quantities of milk, 10 ccs of milk may be obtained from each of the teats (e.g., four teats) and pooled with the same volume of samples of milk from every other animal (e.g., 40 cc). After mixing, a bulk tank equivalent sample can be drawn for IS1311 analysis (e.g., Step C). Thus, a bulk milk sample or BTM sample is inclusive of such a pooled sample.

Preferably, prior to collecting the bulk milk sample, the milk is agitated for at least 10 minutes. Agitation ensures that the milk sample will represent all the milk in the tank. Preferably, all samples are collected from the top of the bulk tank or other container. Bulk tank milk samples are preferably not obtained from the tank outlet, which is difficult to sanitize and may produce inaccurate results. The sample may be collected using a clean and sanitized dipper or a sterile pipette and syringe. Because results from a single bulk milk sample can provide inconclusive results, it is preferred that two, three, or more bulk milk samples be used for IS1311 analysis (e.g., Step C). Preferably, the temperature of the bulk (pooled) milk is recorded and the sample container is labeled. The sample may be transported on ice. The sample may be stored prior to analysis. Preferably, analysis of the sample is carried out as soon as possible after collection. Preferably, the bulk milk sample represents one milking. When the bulk milk sample is collected from a bulk milk tank, the sample is preferably collected after 1-2 hours of milking.

In the various methods of the invention in which the presence of the Map IS1311 insertion sequence is determined. The determination of the amount of nucleic acid (e.g., DNA) is carried out with a technology that allows quantification of the amount of IS1311 identified DNA in the bulk milk sample. In some embodiments, the presence of the Map IS1311 insertion sequence may be determined by amplifying a Map IS1311-specific nucleic acid in the bulk milk sample using polymerase chain reaction (PCR); and detecting the amplified IS1311 insertion sequence shared by *Mycobacterium avium* subspecies *avium*, *Mycobacterium avium* subspecies *paratuberculosis*, *Mycobacterium hominissuis*, and *Mycobacterium avium* complex (MAC).

The presence of the Map IS1311 insertion sequence may be determined by contacting the sample with an oligonucleotide (primer or primer fragment) within, or which overlaps with, the Map IS1311 insertion sequence, allowing an amplification reaction to occur, and detecting the amplification product. Examples of primer sets suitable for detecting the presence of Map in biological samples (e.g., in a bulk milk sample) are provided herein. One non-limiting example of such a primer set is found in two pairs of PCR primers, the first pair (IS1 (SEQ ID NO: 1) and IS2 (SEQ ID NO: 2)) designed to amplify 242 base pair (bp) sequence of the IS1311 insertion sequence, and the second pair (IS3 (SEQ ID NO: 3) and IS4 (SEQ ID NO: 4)) designed to span a 104 bp region within the IS1311 insertion sequence. These pairs of primers can be used in standard or nested PCR protocols. The IS1311 primer pairs identify 6-8 copies whereas primers based upon the IS900 insertion sequence identify 14-18 copies.

In some embodiments, the first primer set comprises the oligonucleotides of primer set 1 (SEQ ID NO: 1 and 2) or fragments of SEQ ID NO:1 and SEQ ID NO:2 that comprise at least 8 contiguous nucleotides of SEQ ID NOs:1 and 2. In some embodiments, the second primer set comprises the oligonucleotides of primer set 2 (SEQ ID NOs: 3 and 4) or fragments of SEQ ID NO:3 and SEQ ID NO:4 that comprise at least 8 contiguous nucleotides of SEQ ID NOs:3 and 4. In some embodiments, the first primer set comprises fragments of at least 8 consecutive nucleotides of SEQ ID NOs:1 and 2 and the second primer set comprises fragments of at least 8 consecutive nucleotides of SEQ ID NOs:3 and 4. More particularly, the invention may utilize two sets of primers in a "nested PCR" method of detecting Map. Primer sets suitable for the identification of Map in biological samples (e.g., a bulk tank milk sample) are provided by the subject invention as well. One non-limiting example of such a primer set is found in two pairs of PCR primers, the first pair (IS1 (SEQ ID NO: 1) and IS2 (SEQ ID NO: 2)) designed to amplify the 242 bp IS1311 sequence, and the second pair (IS3 (SEQ ID NO: 3) and IS4 (SEQ ID NO: 4)) designed to span a 104 bp region within the IS1311 region are also provided by the subject invention. These pairs of primers can be used in standard or nested PCR protocols. In some embodiments three consecutive bulk milk samples are collected and tested using IS1311 base and nested primers.

In some embodiments, in (a)(i) and (a)(ii), either or both the first test and second test are immunoassays (e.g., enzyme-linked immunosorbent assays (ELISA)) that target antigen targets in the blood of the animal. Preferably, the first test comprises FUIDI #1 and/or the second test comprises FUIDI #2. The FUIDI #1 and FUIDI #2 tests (referred to collectively as the FUIDI test) are described in U.S. Pat. No. 8,143,012 (Monif), which is incorporated herein by reference in its entirety. To achieve the mandated specificity indicative of only Map, the target antigens of other commercial Map ELISA tests have had to be based upon a limit antigenic array such as the lipoarabinomannan or selected Map surface proteins. The serological response is a partial function of antigen complexity. Different antigens elicit divergent types of antibodies. Whole organism antigenic utilization elicits an array of antibodies whose spectrum of reactivity exceeds that induced by subunits of the organism. By using combinations of whole organism protoplasmic proteins, the FUIDI test presents a significantly broader antigen array.

The method for herd animal management includes a step of categorizing the animals into a plurality of categories based, at least in part, on the results of the first and second tests. Categorization of animals can be made on the basis of a threshold or cut-off, or range of antibody. For example, categorization of animals can be based on the presence of any detectable Map-specific antibody (a first level or "low" level of Map-specific antibody, which represents a "positive" test), a second level or "intermediate" level of Map-specific antibody that is higher than the first level, and a third level or "high" level of Map-specific antibody that is higher than the second level. Low, intermediate, and high ranges of antibody can be established by those of ordinary skill in the art. Table 1, below, shows a comparison of positivity between Map ELISA tests. The level of Map-specific antibody designated as a positive test for the probability of developing disease was based upon serial testing of animals documented at necropsy to have developed advanced disease (Johne's disease).

TABLE 1

Correlation between preFUIDI #1 OD readings and positive Parachek ® and IDEXX ® ELISA tests

| PreFUIDI #1 OD | Parachek ® positive/total number | IDEXX ® positive/total number |
|---|---|---|
| 2.0-2.50 (positive) | 0/4 | 0/4 |
| 2.51-3.50 (positive) | 2/6 | 1/6 |
| greater than 3.51 (strong positive) | 4/8 | 5/8 |

Utilization of the methods of the invention facilitates the subdivision of a dairy herd into milking animals into categories (also referred to herein as groups). Several factors can contribute to the optimal group size of cows in any dairy herd (Grant R. J., and Albright, J. L., "Effect of Animal Grouping on Feeding Behavior and Intake of Dairy Cattle," J. Dairy Sci. 2001, 84 (E. Suppl.), E:156-E163, which is incorporated herein by reference in its entirety), such as feed bunk space and competition for feed, water and free stalls; social interactions among cows and how they are affected by group size; space available to the cow; size of holding area and capacity of milking parlor; animal body size and age; body condition; days in milk (DIM); stall size and equity (stalls equally comfortable and equally likely to be used); and adequacy of ventilation. In some embodiments, the number of animals in each category is over 500 animals. In some embodiments, the number of animals in each category is over 200. In some embodiments, the number of animals in each category is in the range of 200 to 500. In some embodiments, the number of animals in each category is in the range of 150 to 199. In some embodiments, the number of animals in each category is in the range of 100 to 150. In some embodiments, the number of animals in each category is in the range of 50 to 99. In some embodiments, the number of animals in each category is in the range of 40 to 100.

Optionally, the animals of each category can be physically separated from contact with or exposure to animals of any other category (e.g., by separation in different pastures or confinements such as stalls, pens, milking parlors, concrete lots, etc.). In some embodiments, the animals of each category are not physically separated.

Animals of a category can be visually or electronically tagged or otherwise labeled as belonging to a category using a variety of methods known in the art for labeling livestock or wildlife (e.g., electronic chip, electronic or non-electronic ear tag). Animals can be removed from a category as necessary and as indicated according to the monitoring regimens of the methods of the invention. Animals that meet the category's criteria can be added to the category to maintain a desired number of animals in each category (the number of animals in each category may be the same or different). Multiple herds of animals can be categorized and monitored using the methods of the invention. Optionally, animals from a given category in one herd can be moved to the corresponding category of another herd, e.g., to maintain a desired number of animals in a category.

Various arrangements of category separation and labeling are possible. In some embodiments, animals of each category are separated and tagged or otherwise labeled. In other embodiments, animals of each category are not separated, but are tagged or otherwise labeled. In other embodiments, the animals of each category are separated, but are not tagged or otherwise labeled.

In some embodiments, as shown in FIG. 1A, following determination of Map-specific antibody level in blood of individual animals (Step A), the animals are categorized (Step B) into five categories. Preferably, the five categories comprise:

(i) a first category of animals having no detectable Map-specific antibodies in the first and second tests;

(ii) a second category of animals having a low level of Map-specific antibody in the first test and no detectable Map-specific antibody in the second test;

(iii) a third category of animals having an intermediate level of Map-specific antibody in the first test and no detectable Map-specific antibody in the second test;

(iv) a fourth category of animals having a high level of Map-specific antibody in the first test and no detectable Map-specific antibody in the second test; and (v) a fifth category of animals having a low, intermediate, or high level of Map-specific antibody in the first test, and low or intermediate level of Map-specific antibody in the second test.

In some embodiments, in which the first test comprises FUIDI #1 and/or the second test comprises FUIDI #2, the five categories comprise:

(i) a first category of animals having no detectable Map-specific antibodies in the FUIDI#1 and FUIDI#2 tests;

(ii) a second category of animals having a low level of Map-specific antibody in the FUIDI#1 test and no detectable Map-specific antibody in the FUIDI#2 test;

(iii) a third category of animals having an intermediate level of Map-specific antibody in the FUIDI#1 test and no detectable Map-specific antibody in the FUIDI#2 test;

(iv) a fourth category of animals having a high level of Map-specific antibody in the FUIDI#1 test and no detectable Map-specific antibody in the FUIDI#2 test; and (v) a fifth category of animals having a low, intermediate, or high level of Map-specific antibody in the FUIDI#1 test, and low or intermediate level of Map-specific antibody in the FUIDI#2 test.

First and Second Categories (Also Refereed to Herein as Groups a and B)

In some embodiments, if negative and barring clinical indications to the contrary (diarrhea or reduced lactation), Groups A and B can be effectively monitored through periodic bulk milk testing using direct and nesting primers based on the IS1311 insertion sequence after each change of diet or every three months.

If Map-like DNA is identified in a bulk milk sample, three other bulk milk samples should be retested as soon as possible. Repeat testing is done to rule out incidental fecal contamination. If the test for the IS1311 insertion sequence (e.g., IS1311 PCR test) continues to demonstrate the presence of Map or genomic variant DNA, the risk group (i.e., category) is retested using the FUIDI #2 Map test. Any animal whose milk production shows a decline should have its milk tested using IS1311 primers. If serological retesting and selected milk testing fails to identify one or more shredders, the milk of the remaining animals can be tested using IS1311 primers.

Third Category (Also Referred to Herein as Group C)

Group C can be handled as one would with Groups A or B; however, animals in this subgroup should preferably have their milk test in the month prior to and in the two months after calving. Animals that have controlled a prior significant infectious Map challenge may reactivate *mycobacterium* replication, if subjected to environmental and/or nutritional stress at this time of depressed cellular immunity.

Fourth Category (Also Referred to Herein as Group D)

Group D is comparable to Group C, except that the probability of break down at parturition is greater in Group D. Milk testing should preferably be done monthly in the three months before calving and two months after.

Fifth Category (Also Referred to as Group E)

Animals in Group E have the highest potential for shedding Map into milk. Emphasis should be given to ample proper nutrition. If Map-like DNA is detected in bulk milk using IS1311 direct and/or nested primers, the individual animals should have their milk tested using these primers as well as IS 900 primers in order to identify the shedder or shedders and remove these animals from the milking group.

In any group, if Map DNA is detected in two or more individual milk samples, animal is removed from production within the subgroup.

The presence of an active infection does not necessarily correlate with *mycobacterium* shedding into milk.

Allowing Map-Infected Animals to Remain in Production Through Selective Monitoring If the United States Department of Agriculture (USDA) were to implement a true test- and cull policy, more likely than not, the dairy and dairy-based industries would be significantly compromised. The incidence of infected dairy cows in large dairy herds is estimated to exceed 50%. In 2007, the USDA estimated that 70% of U.S. herds contained one or more Map infected animals (USDA-APHIS Johne's Disease in U.S. Dairies, 1991-2007, USDA website). With the overwhelming preponderance of evidence indicating that Map is causally linked to gastrointestinal disease in humans including irritable bowel and Crohn's disease and with this evidence having been dispersed in the public realm for a defined period of time, doing nothing is a precarious option. The methods of the invention facilitate separation of Map-infected animals (e.g., Map-infected dairy cows) from Map infectious animals coupled with public health safety nets to identify both Map and genomic variants at the bulk tank stage as well as monitoring animals at augmented risk for immunological breakdown. By creating milking groups with varying potential for shedding of Map into milk, the level and cost of herd monitoring can be reduced.

As shown schematically in FIGS. 1B-1D, as part of a selective monitoring program that may be used as a component of the herd management method of the invention, after determining the presence of the Map IS1311 insertion sequence in a bulk milk sample from the first, second, or third risk category of animals in accordance with step (c), if the Map IS1311 insertion sequence is determined to be absent in the bulk milk sample of step (c), steps (a) and (c) may be repeated annually to reassess the risk category.

As shown schematically in FIGS. 1B-1E, as part of a selective monitoring program, after determining the presence of the Map IS1311 insertion sequence in a bulk milk sample from the first, second, third, or fourth risk category of animals in accordance with step (c), if the Map IS1311 insertion sequence is determined to be present in the bulk milk sample step (c), step (c) may be repeated one or more times to exclude incidental contamination (e.g., incidental fecal contamination). Optionally, after repeating step (c) one or more times to exclude incidental contamination, if the Map IS1311 insertion sequence is determined to be present in repeated step (c) such that incidental contamination is excluded, the selective monitoring program may further comprise determining the presence of the Map IS1311 insertion sequence in a milk sample of each individual animal in the risk category (see FIGS. 1D-1E). Optionally, if the Map IS1311 insertion sequence is determined to be present in the milk sample of at least one individual animal, the selective monitoring program, the method may further comprise removing that individual animal or animals from milk production, and if the Map IS1311 insertion sequence is determined to be absent in the milk sample of at least one individual animal, the method may further comprise repeating step (a) and step (c) annually to reassess the risk category.

Figure 1B:
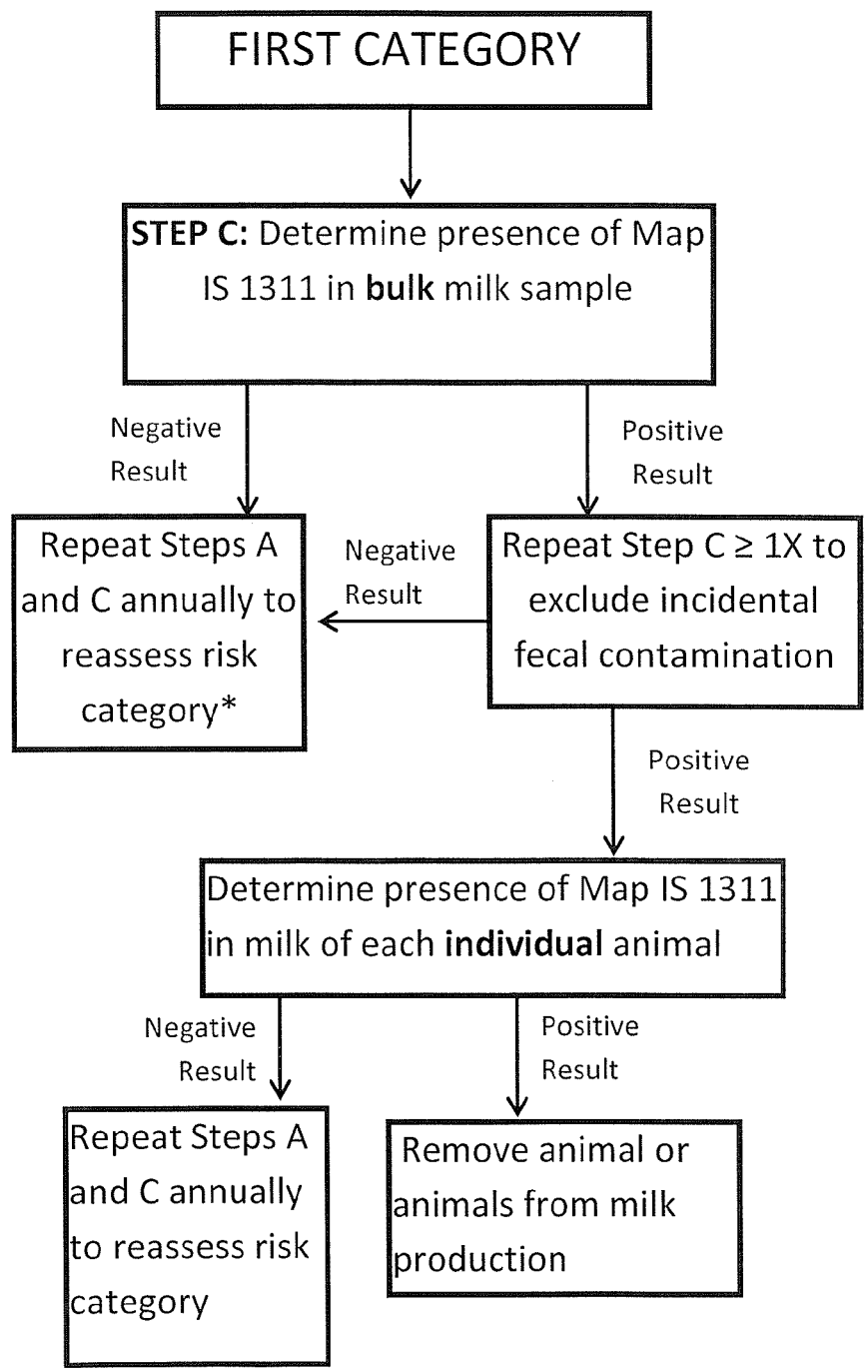
Figure 1C:
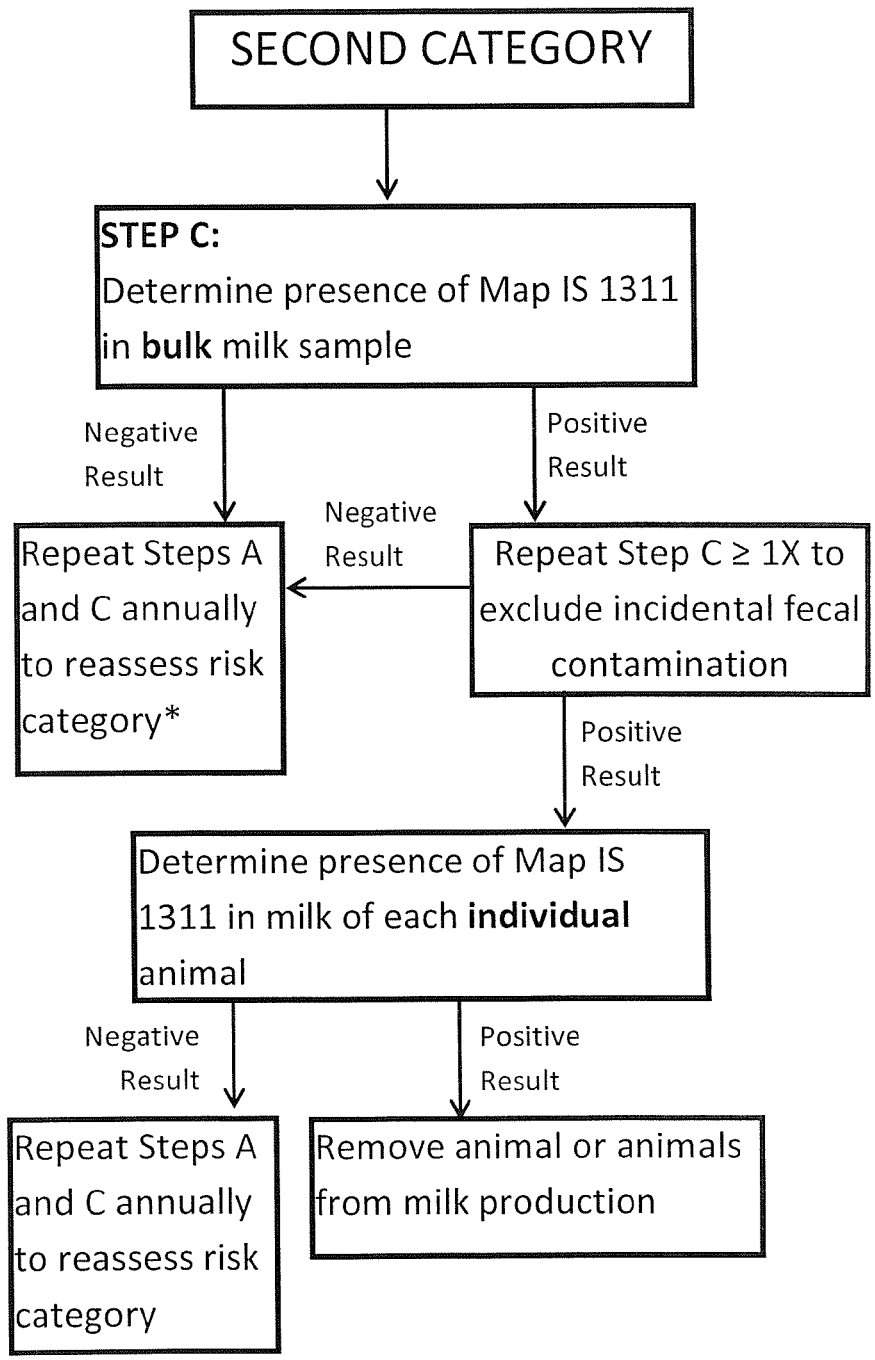
Figure 1D:
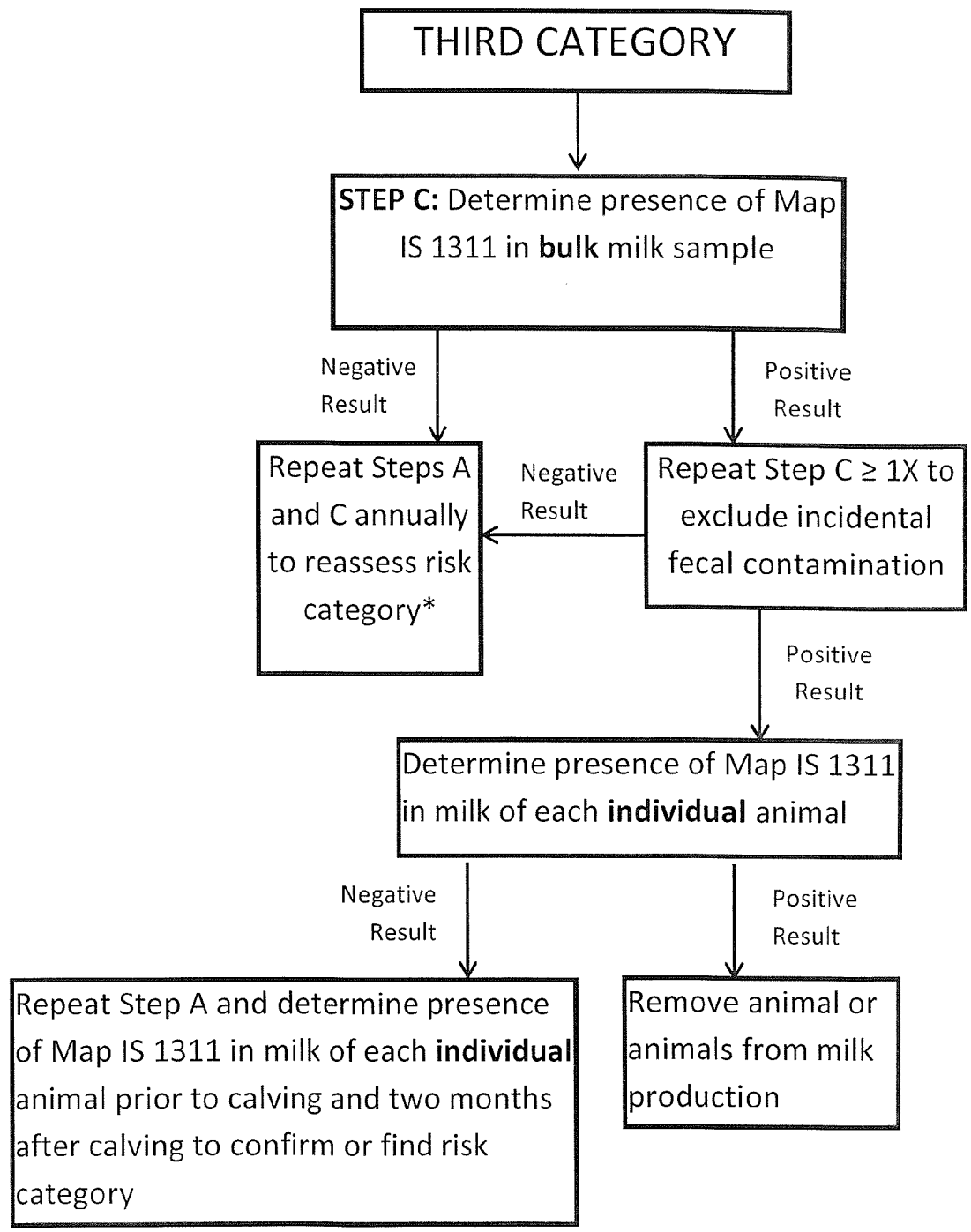

As shown in FIG. 1D, as part of a selective monitoring program, after determining the presence of the Map IS1311 insertion sequence in a bulk milk sample from the third risk category of animals in accordance with step (c), if the Map IS1311 insertion sequence is determined to be absent in the bulk milk sample, step (a) may be repeated and the presence of the Map IS1311 in milk of each individual animal may be determined prior to calving and two months after calving.

As shown in FIGS. 1B and 1C, as part of a selective monitoring program, after determining the presence of the Map IS1311 insertion sequence in a bulk milk sample from the first or second risk category of animals in accordance with step (c), if the Map IS1311 insertion sequence is determined to be present in the bulk milk sample of step (c), step (c) may be repeated one or more times to exclude incidental contamination (e.g., incidental fecal contamination), and if the Map IS1311 insertion sequence is determined to be present in repeated step (c) such that incidental contamination is excluded, the presence of the Map IS1311 insertion sequence in a milk sample of each individual animal in the risk category may be determined, and if absent, steps (a) and (c) may be repeated annually to reassess risk category.

Figure 1E:
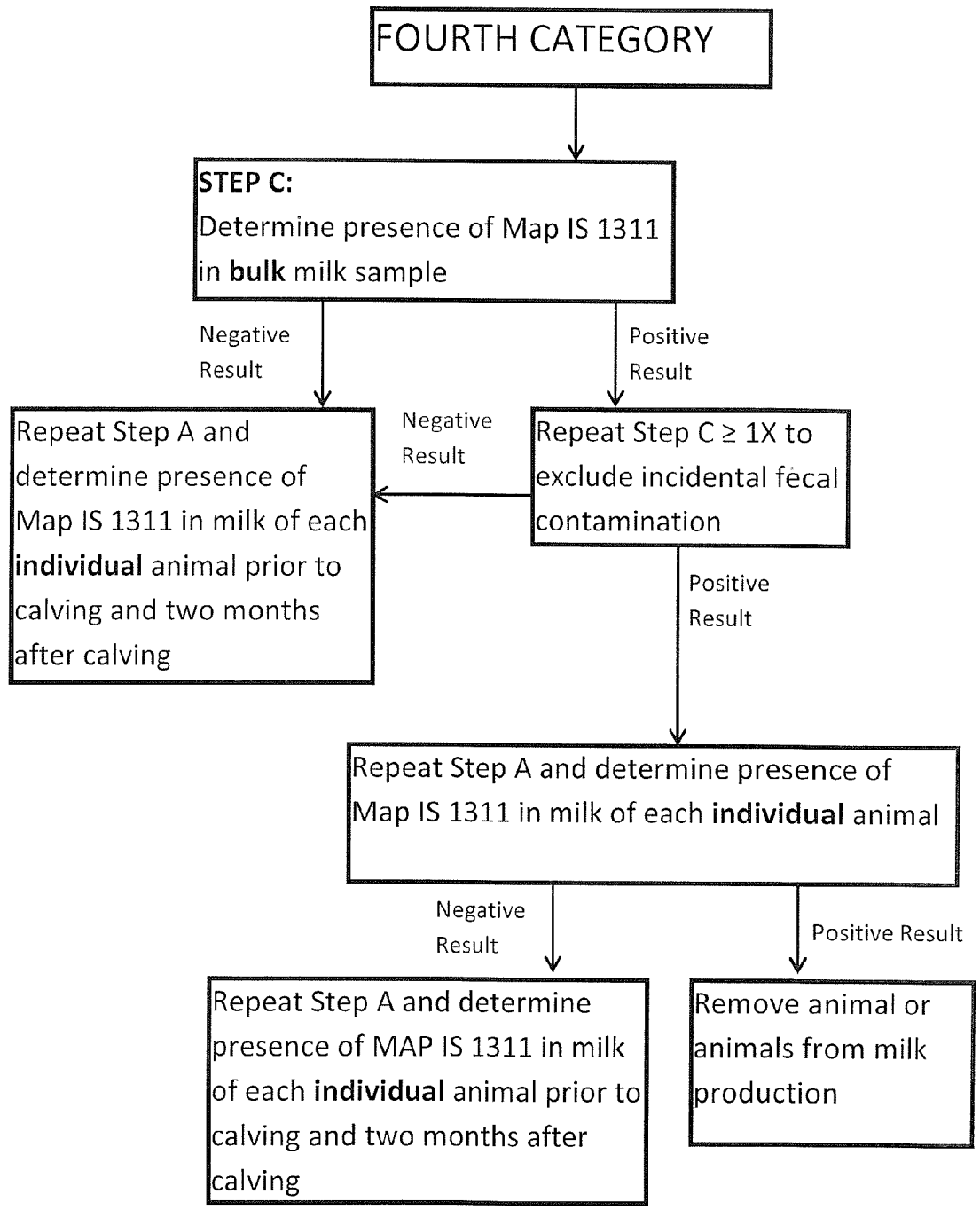

As shown in FIGS. 1D and 1E, as part of a selective monitoring program, after determining the presence of the Map IS1311 insertion sequence in a bulk milk sample from the third or fourth risk category of animals in accordance with step (c), if the Map IS1311 insertion sequence is determined to be present in the bulk milk sample of step (c), step (c) may be repeated one or more times to exclude incidental contamination, and if the Map IS1311 insertion sequence is determined to be present in repeated (c) such that incidental contamination is excluded, the presence of the Map IS1311 insertion sequence in a milk sample of each individual animal in the risk category may be determined, and if absent, step (a) may be repeated and the presence of Map IS1311 of each individual animal may be determined prior to calving and two months after calving.

As shown in FIG. 1E, as part of a selective monitoring program, after determining the presence of the Map IS1311 insertion sequence in a bulk milk sample from the fourth risk category of animals in accordance with step (c), if the Map IS1311 insertion sequence is determined to be absent in the bulk milk sample of step (c), step (a) may be repeated and the presence of Map IS1311 in milk of each individual animal may be determined prior to calving and two months after calving.

Figure 1F:
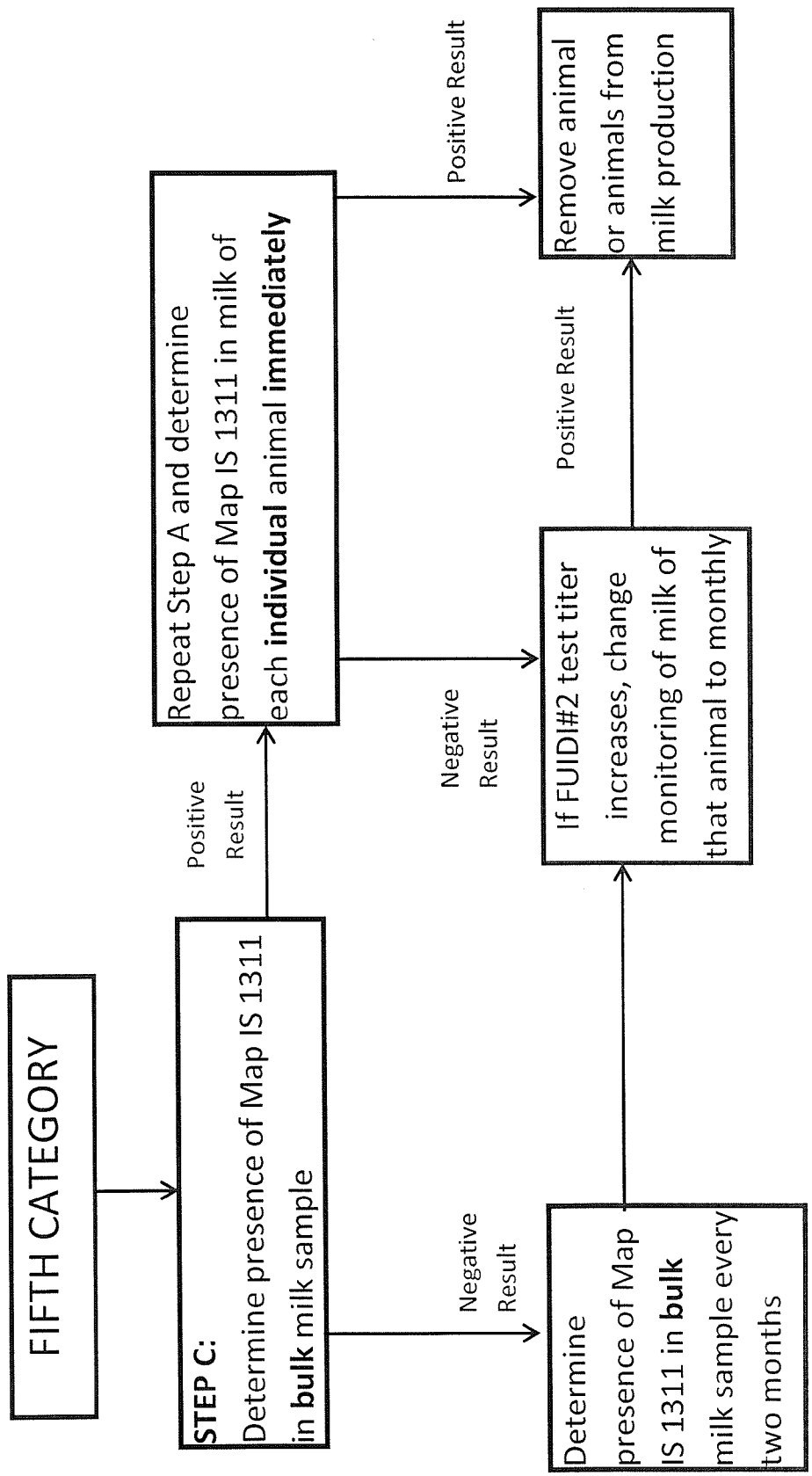

As shown in FIG. 1F, as part of a selective monitoring program, after determining the presence of the Map IS1311 insertion sequence in the bulk milk sample from the fifth risk category of animals in accordance with step (c), if the Map IS1311 insertion sequence is determined to be absent in the bulk milk sample of step (c), the presence of Map IS1311 in a bulk milk sample of the fifth risk category of animals may be determined every two months. Optionally, the method includes increasing the frequency of Map IS1311 determination in milk samples of individual animals of the fifth category to monthly if the second Map-specific antibody titer in the second test (e.g., FUIDI #2) increases. The method may further include removing the animal or animals from milk production if Map IS1311 is determined to be present in the milk sample of the individual animal or animals tested.

As shown in FIG. 1F, as part of a selective monitoring program, after determining the presence of the Map IS1311 insertion sequence in a bulk milk sample from the fifth risk category of animals in accordance with step (c), if the Map IS1311 insertion sequence is determined to be present in the bulk milk sample of step (c), step (a) may be repeated and the presence of Map IS1311 in milk of each animal of the fifth risk category may be determined immediately. The method may further include removing the animal of animals from milk production if Map IS1311 is determined to be present in milk of the individual animal or animals.

In some embodiments, as indicated in FIGS. 1B-1D, when repeating steps (a) and (c) annually to reassess risk category following a negative result from step (c), the animals may be retested individually at any time if clinical indications of Map such as diarrhea or reduced lactation occur.

In some embodiments, the determining of the presence of Map IS1311 insertion sequence in (c) comprises amplifying Map IS1311-specific nucleic acid in the bulk milk sample using polymerase chain reaction (PCR); and detecting the IS1311 insertion sequence shared by *Mycobacterium avium* subspecies *avium*, *Mycobacterium avium* subspecies *paratuberculosis*, *Mycobacterium hominissuis*, and *Mycobacterium avium* complex (MAC). Amplification typically comprises contacting the bulk milk sample with a primer set that amplifies a nucleic acid sequence within the Map 1311 insertion sequence. In some embodiments, the amplification comprises contacting the bulk milk sample with a primer set comprising a first primer pair and a second primer pair, wherein the first primer pair is designed to amplify the 242 base pair IS1311 sequence, and wherein the second primer pair is designed to span a region within the IS1311 sequence.

In some embodiments, the determining in (c) comprises the steps of:
  (a) treating the bulk milk sample to solubilize the nucleic acids therein;
  (b) forming a polymerase chain reaction (PCR) solution comprising:
    (i) at least a portion of the solubilized nucleic acids from step (a);
    (ii) a PCR primer set that amplifies a nucleic acid sequence within the Map IS1311 insertion sequence;
    (iii) a mixture of nucleoside triphosphate monomers; and
    (iv) a PCR polymerase in a buffered solution;
  (c) carrying out a PCR on the PCR solution to amplify any Map IS1311-specific nucleic acid which is specific for the particular primer set used to a level sufficient for detection; and
  (d) detecting the presence of amplified MAP IS1311-specific nucleic acid in the resulting solution which is specific for the particular primer set used; wherein the detection of the amplified Map IS1311-specific nucleic acid which is specific for the particular primer set used indicates that Map is present in the bulk milk sample.

In some embodiments in which a primer set is used in (c), the primer set comprises direct and nested primer sets comprising: IS1 (SEQ ID NO: 1), IS2 (SEQ ID NO: 2), IS3 (SEQ ID NO: 3), and IS4 (SEQ ID NO: 4), or a fragment comprising at least 8 contiguous nucleotides thereof In some embodiments, the detection of the presence of amplified Map IS1311-specific nucleic acid comprises gel electrophoresis of the amplified Map IS1311-specific nucleic acid solution and staining of the resulting gel to visualize the band of the MAP IS1311-specific nucleic acid specific for the particular primer set used.

In some embodiments, at least one of the oligonucleotides in the primer set or at least one of the nucleoside triphosphate monomers contains a label which will be incorporated into the amplified Map IS1311-specific nucleic acid and can be used for the detection of the amplified Map IS1311-specific nucleic acid.

In some embodiments, the detection of the presence of amplified Map IS1311-specific nucleic acid comprises in (c) uses a nested polymerase chain reaction (PCR) procedure comprising the steps of:
 (a) treating the bulk milk sample to solubilize the nucleic acids therein;
 (b) forming a first PCR solution containing at least a portion of the solubilized nucleic acids from step (a), a first PCR primer set, a first mixture of nucleoside triphosphate monomers, and a first PCR polymerase in a first buffered solution, wherein the first primer set comprises a first pair of oligonucleotides as set forth in primer set 1, 3, 4, 5, 6, 7, 8, 9, 10, 11, 12, 63, 64, 65, 66 or 67 or fragments of the first pair of oligonucleotides that are at least 8 consecutive nucleotides in length;
 (c) performing a first polymerase chain reaction on the first PCR solution to amplify any IS1311-specific nucleic acid which is specific for the first primer set used;
 (d) forming a second PCR solution containing at least a portion of the PCR-reacted first PCR solution from step (c), a second PCR primer set, a second mixture of nucleoside triphosphate monomers, and a second PCR polymerase in a second buffered solution, wherein the second primer set comprises a second pair of oligonucleotides as set forth in primer set 2, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 68, 69, 70, 71 or 72 or fragments of the second pair of oligonucleotides that are at least 8 consecutive nucleotides in length;
 (e) performing a second polymerase chain reaction on the second PCR reaction solution to amplify any Map IS1311-specific nucleic acid which is specific for the second primer set used to a level sufficient for detection; and
 (f) detecting the presence of amplified Map IS1311-specific nucleic acid in the resulting solution from step (e) which is specific for the second primer set; wherein the detection of the amplified Map IS1311-specific nucleic acid which is specific for the second primer set indicates that Map is present in the bulk milk sample.

In some embodiments, the detection in step (f) may comprise gel electrophoresis of the amplified Map IS1311-specific nucleic acid solution and staining of the resulting gel to visualize the Map IS1311-specific nucleic acid on the gel. In some embodiments, either the primers, or one or more of the monomers, or both, employed in steps (b) and (d) contains a label whereby the amplified Map IS1311-specific nucleic acid that results in step (e) contains the label, and the detection in step (f) comprises detecting the presence of the label.

Increasing Herd Ability to Withstand Environmental Challenges by Map-Like *Mycobacterium*

Groups A and B are composed of animals that have effectively handled their infection by Map. Recovery from *mycobacterium* infections is primarily a function of cell-mediated immunity rather than humeral immunity. Heifers from these groups constitute prime candidates for internal restocking. If this policy is implemented over time, it is more probable than not, that one will develop a herd with increased cell-mediated immunity. Accordingly, another aspect of the invention is a method to strengthen the ability of milk-producing animals to resist environmental challenges by pathogenic *mycobacterium* comprising *Mycobacterium avium* subspecies *paratuberculosis* (Map), the method comprising:
 (a) identifying milk-producing animals that have a low antibody level to Map (anti-Map antibody level);
 (b) serially monitoring the level of anti-Map antibodies in the identified animals;
 (c) retaining female animals that maintain a low anti-Map antibody level; and
 (d) incorporating female animals into a herd as replacement animals to replace female animals taken out of milk production, wherein the incorporated female animals are progeny of animals that maintain a low-anti-Map antibody level.

In some embodiments, the individual animals identified by their prior exposure, magnitude of immune stimulation, and status of the infection, allow identification of animals that have effectively contained environmental challenges by pathogenic *mycobacterium*, specifically *Mycobacterium avium* subspecies *paratuberculosis*.

In some embodiments, the female progeny from animals whose mother do exhibit the continued ability to effectively handle environmental challenges by pathogenic *mycobacterium* comprising *Mycobacterium avium* subspecies *paratuberculosis* constitute prime replacement animals.

In some embodiments, the replacement animals are drawn from animals with a documented ability to tolerate environmental challenges by pathogenic *mycobacterium* in order to enhance overall herd immunity to Map and other intra-cellular pathogens.

Another aspect of the invention concerns a method of detecting the presence of pathogenic *mycobacterium* comprising *Mycobacterium avium* subsp. *paratuberculosis* (Map) in a bulk milk sample obtained from a volume of milk from a plurality of milk-producing animals, comprising determining the presence of the Map IS1311 insertion sequence (Genbank accession # U16276) in the bulk milk sample. The presence of the Map IS1311 insertion sequence may be determined, for example, by amplifying Map IS 1311-specific nucleic acid in the bulk milk sample using polymerase chain reaction (PCR); and detecting the IS1311 insertion sequence shared by *Mycobacterium avium* subspecies *avium, Mycobacterium avium* subspecies *paratuberculosis, Mycobacterium hominissuis*, and *Mycobacterium avium* complex (MAC). Amplification may comprise contacting the bulk milk sample with a primer set that amplifies a nucleic acid sequence within the Map 1311 insertion sequence. In some embodiments, the amplifying comprises contacting the bulk milk sample with a primer set comprising a first primer pair and a second primer pair, wherein the first primer pair is designed to amplify the 242 base pair IS1311 sequence, and wherein the second primer pair is designed to span a region within the IS1311 sequence.

In some embodiments of the various methods of the invention, the milk-producing animals are selected from among cows, sheep, goats, llamas, buffalo, camels, and yaks. In some embodiments of the various methods of the invention, the milk-producing animals are cows.

In some embodiments of the various methods of the invention, the presence of the Map IS1311 insertion sequence may be determined by:
 (a) treating the bulk milk sample to solubilize the nucleic acids therein;
 (b) forming a polymerase chain reaction (PCR) solution comprising:
  (i) at least a portion of the solubilized nucleic acids from step (a);

(ii) a PCR primer set that amplifies a nucleic acid sequence within the Map IS1311 insertion sequence;

(iii) a mixture of nucleoside triphosphate monomers; and (iv) a PCR polymerase in a buffered solution;

(c) carrying out a PCR on the PCR solution to amplify any Map IS1311-specific nucleic acid which is specific for the particular primer set used to a level sufficient for detection; and (d) detecting the presence of amplified MAP IS1311-specific nucleic acid in the resulting solution which is specific for the particular primer set used; wherein the detection of the amplified Map IS1311-specific nucleic acid which is specific for the particular primer set used indicates that Map is present in the bulk milk sample.

In some embodiments, the primer set comprises direct and nested primer sets comprising: IS1 (SEQ ID NO: 1), IS2 (SEQ ID NO: 2), IS3 (SEQ ID NO: 3), and IS4 (SEQ ID NO: 4), or a fragment comprising at least 8 contiguous nucleotides thereof.

In some embodiments, the detection of the presence of amplified Map IS1311-specific nucleic acid comprises gel electrophoresis of the amplified Map IS1311-specific nucleic acid solution and staining of the resulting gel to visualize the band of the MAP IS1311-specific nucleic acid specific for the particular primer set used.

In some embodiments, at least one of the oligonucleotides in the primer set or at least one of the nucleoside triphosphate monomers contains a label which will be incorporated into the amplified Map IS1311-specific nucleic acid and can be used for the detection of the amplified Map IS1311-specific nucleic acid.

In some embodiments, the presence of the Map IS1311 insertion sequence may be determined using a nested polymerase chain reaction (PCR) procedure comprising the steps of:

(a) treating the bulk milk sample to solubilize the nucleic acids therein;

(b) forming a first PCR solution containing at least a portion of the solubilized nucleic acids from step (a), a first PCR primer set, a first mixture of nucleoside triphosphate monomers, and a first PCR polymerase in a first buffered solution, wherein the first primer set comprises a first pair of oligonucleotides as set forth in primer set 1, 3, 4, 5, 6, 7, 8, 9, 10, 11, 12, 63, 64, 65, 66 or 67 or fragments of the first pair of oligonucleotides that are at least 8 consecutive nucleotides in length;

(c) performing a first polymerase chain reaction on the first PCR solution to amplify any IS1311-specific nucleic acid which is specific for the first primer set used;

(d) forming a second PCR solution containing at least a portion of the PCR-reacted first PCR solution from step (c), a second PCR primer set, a second mixture of nucleoside triphosphate monomers, and a second PCR polymerase in a second buffered solution, wherein the second primer set comprises a second pair of oligonucleotides as set forth in primer set 2, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 68, 69, 70, 71 or 72 or fragments of the second pair of oligonucleotides that are at least 8 consecutive nucleotides in length;

(e) performing a second polymerase chain reaction on the second PCR reaction solution to amplify any Map IS1311-specific nucleic acid which is specific for the second primer set used to a level sufficient for detection; and (f) detecting the presence of amplified Map IS1311-specific nucleic acid in the resulting solution from step (e) which is specific for the second primer set; wherein the detection of the amplified Map IS1311-specific nucleic acid which is specific for the second primer set indicates that Map is present in the bulk milk sample.

In some embodiments, the detection in step (f) comprises gel electrophoresis of the amplified Map IS1311-specific nucleic acid solution and staining of the resulting gel to visualize the Map IS1311-specific nucleic acid on the gel. In some embodiments, either the primers, or one or more of the monomers, or both, employed in steps (b) and (d) contains a label whereby the amplified Map IS1311-specific nucleic acid that results in step (e) contains the label, and the detection in step (f) comprises detecting the presence of the label.

The subject invention provides, in one of its various embodiments, a PCR-based method for detecting a subclinical or clinical Map infection in an animal subject by testing a biological sample. In some embodiments, the invention utilizes two sets of primers in a "nested PCR" method of detecting Map. Primer sets suitable for the identification of Map in biological samples are provided by the subject invention as well. One non-limiting example of such a primer set is found in two pairs of PCR primers, the first pair (IS1 (SEQ ID NO: 1) and IS2 (SEQ ID NO: 2)) designed to amplify the 242 bp IS1311 sequence, and the second pair (IS3 (SEQ ID NO: 3) and IS4 (SEQ ID NO: 4)) designed to span a 104 bp region within the IS1311 region are also provided by the subject invention. These pair of primers can be used in standard or nested PCR protocols.

In the context of this invention, the term "successive" can be used interchangeably with the terms "contiguous" or "consecutive" or the phrase "contiguous span" throughout the subject application. Thus, in some embodiments, a polynucleotide fragment, probe fragment and/or primer fragment may be referred to as "a contiguous span of at least X nucleotides, wherein X is any integer value beginning with 8; the upper limit for these various fragments is one nucleotide less than the total number of nucleotides associated with a particular SEQ ID NO: provided in the Sequence Listing appended hereto (e.g., the number of nucleotides present in the polynucleotide comprising SEQ ID NO: 5 is 1317, thus a fragment of SEQ ID NO: 5 corresponds to any consecutive span of X nucleotides of SEQ ID NO: 5, wherein X is any integer between, and including, 8 and 1316).

The terms "detect", "detecting", "determine", "determining", and grammatical variations thereof include assaying or otherwise establishing the presence or absence of the target (e.g., Map, Map-specific antibodies, Map-specific antigen, Map IS1311 insertion sequence (Genbank accession #U16276)) in a sample, such as blood or a bulk milk sample. The terms encompass quantitative, semi-quantitative, and qualitative detection methodologies. In embodiments of the invention involving detection of a protein (as opposed to nucleic acid molecules), the detection method is preferably an immunoassay such as an ELISA-based method. In embodiments of the invention involving detection of a nucleic acid such as a Map-specific nucleic acid, the detection method is preferably an amplification method such as polymerase chain reaction (PCR), including for example nested PCR. Preferably, in the various embodiments of the invention, the detection method provides an output (i.e., readout or signal) with information concerning the presence, absence, or amount of the target in a sample from a subject. For example, the output may be qualitative (e.g., "positive" or "negative"), or quantitative (e.g., a concentration such as nanograms per milliliter).

The terms "nucleotide sequence", "nucleic acids", "polynucleotide", "oligonucleotide" or "nucleic acid sequence" can be used interchangeably and are understood to mean, according to the present invention, either a double-stranded DNA, a single-stranded DNA or products of transcription of the said DNAs (e.g., RNA molecules). It should also be understood that the present invention does not relate to genomic polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

The terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment. "Link" or "join" refers to any method known in the art for functionally connecting peptides, including, without limitation, recombinant fusion, covalent bonding, disulfide bonding, ionic bonding, hydrogen bonding, and electrostatic bonding. Additionally, the terms "complementary", "fully complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" can be used herein as a synonym to "complementary polynucleotide", "complementary nucleic acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the specified polynucleotide (e.g., a specified SEQ ID NO:).

The term "fragment(s)", "probe fragment(s)" or "primer fragment(s)" is used herein to denote a nucleic acid sequence comprising, consisting essentially of, or consisting of at least 8 consecutive nucleotides of any one of SEQ ID NOs: 1, 2, 3, 4, 5, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 108, 110, 111, 112, 113, 114, 115, 116, 117, 118, 119, 120, 121, 122, 123, 124, 125, 126, 127, 128, 129, 120, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212 or 213, said fragment of at least 8 consecutive nucleotides being at least one nucleotide shorter than the number of nucleotides associated with a particular SEQ ID NO: (e.g., any one of SEQ ID NOs: 1-5 and 7-213). The subject invention also provides fragments/primers/probes that comprise, consist essentially of, or consist of 100 or fewer consecutive nucleotides as set forth in SEQ ID NO: 5, 7 or 213, provided that each of said fragments, primers or probes contains a span of at least 8 consecutive nucleotides of at least one sequence as set forth in SEQ ID NOs: 1-4 or 8-212 (or polynucleotide sequences fully complementary thereto). In other words, a fragment, probe, or primer can comprise, consist essentially of, or consist of a contiguous/consecutive span of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 consecutive nucleotides of SEQ ID NO: 5, provided that said contiguous/consecutive span of nucleotides includes at least 8 consecutive nucleotides of at least one of the sequences set forth in SEQ ID NOs: 1, 2, 3 or 4 (or nucleotides sequences fully complementary thereto). In certain embodiments, the primers or probes of SEQ ID NO: 1 comprise, consist essentially of, or consist of at least 8, 9, 10, 11, 12, 13, 14, 15, 16, 17, 18, 19, 20 or 21 consecutive nucleotides as set forth in SEQ ID NO: 1. For SEQ ID NO: 2, various primers or probes according to the subject invention comprise, consist essentially of, or consist of at least 8, 9, 10, 11, 12, 13, 14, 15, 16, 17, 18, 19 or 20 consecutive nucleotides as set forth in SEQ ID NO: 2. With respect to SEQ ID NOs: 3 and 4, primers or probes comprise, consist essentially of, or consist of at least 8, 9, 10, 11, 12, 13, 14, 15, 16, 17 or 18 consecutive nucleotides as set forth in SEQ ID NOs: 3 and 4, respectively. Specifically excluded from the scope of the subject invention is the full length nucleic acid sequence identified in SEQ ID NO: 5, 7 or 213 (accession numbers# U16276, AF286339 and X70277 respectively). The primers, probes, and/or fragments set forth in this paragraph can be, optionally, labeled as set forth below.

As used herein, "nested polymerase chain reaction" or nested PCR represents a variation of standard PCR in that two pairs (instead of one pair) PCR primers are used to amplify a fragment. The first pair of PCR primers amplify a fragment similar to a standard PCR. However, a second pair of primers called nested primers (as they lie/are nested within the first fragment) bind inside the first PCR product fragment to allow amplification of a second PCR product which is shorter than the first one. The advantage of nested PCR is that if the wrong PCR fragment was amplified, the probability is quite low that the region would be amplified a second time by the second set of primers. Thus, Nested PCR is a very specific PCR amplification. Nested PCR requires two sets of primers which are used to amplify a specific DNA fragment using two separate runs of PCR. The second pair of primers function to amplify a smaller specific DNA fragment located within the first PCR product. The DNA target template is bound by the first set of primers. The primers may bind to alternative, similar primer binding sites which give multiple products; however, only one of these PCR products give the intended sequence. PCR products from the first PCR reaction are subjected to a second PCR run; however, with a second new set of primers. As these primers are "nested" within the first PCR product, they make it very unlikely that non-specifically amplified PCR product would contain binding sites for both sets of primers. This nested PCR amplification ensures that the PCR product from the second PCR amplification has little or no contamination from non-specifically amplified PCR products from alternative primer target sequences.

The subject invention provides, in one embodiment, methods for the identification of the presence of nucleic acids according to the subject invention in transformed host cells or in cells isolated from an individual suspected of being infected by MAP. In these varied embodiments, the invention provides for the detection of nucleic acids in a sample (obtained from the individual or from a cell culture) comprising contacting a sample with a nucleic acid (polynucleotide) of the subject invention (such as an RNA, mRNA, DNA, cDNA, or other nucleic acid). In a preferred embodiment, the polynucleotide is a probe that is, optionally, labeled and used in the detection system. Many methods for detection of nucleic acids exist and any suitable method for detection is encompassed by the instant invention. Typical assay formats utilizing nucleic acid hybridization includes, and are not limited to, 1) nuclear run-on assay, 2) slot blot assay, 3) northern blot assay (Alwine, et al., *Proc. Natl. Acad. Sci.* 74:5350), 4) magnetic particle separation, 5) nucleic acid or DNA chips, 6) reverse Northern blot assay, 7) dot blot assay, 8) in situ hybridization, 9) RNase protection assay (Melton, et al., *Nuc. Acids Res.* 12:7035 and as described in the 1998 catalog of Ambion, Inc., Austin, Tex.), 10) ligase chain reaction, 11) polymerase chain reaction (PCR), 12) reverse transcriptase (RT)-PCR (Berchtold, et al., *Nuc. Acids. Res.* 17:453), 13) differential display RT-PCR (DDRT-PCR), 14) nested PCR, 15) quantitative PCR or other suitable combinations of techniques and assays. Labels suitable for use in these detection methodologies include, and are not limited to 1) radioactive labels, 2) enzyme labels, 3) chemiluminescent labels, 4) fluorescent labels, 5) magnetic labels, or other suitable labels, including those set forth below. The general methods of PCR are well known in the art and are thus not described in detail herein. For a review of PCR methods, protocols, and principles in designing primers, see, e.g., Innis, et al., PCR Protocols: A Guide to Methods and Applications, Academic Press, Inc. N.Y., 1990. PCR reagents and protocols are also available from commercial vendors, such as Roche Molecular Systems. Furthermore, labels useful in producing probes for use in the disclosed methods are well known in the art and widely available to the skilled artisan. Likewise, methods of incorporating labels into the nucleic acids are also well known to the skilled artisan.

Thus, the subject invention also provides detection probes (e.g., fragments of the disclosed polynucleotide sequences) for hybridization with a target sequence or the amplicon generated from the target sequence. Such a fragment or detection probe will comprise a contiguous/consecutive span of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 consecutive nucleotides of SEQ ID NO: 5, provided that said contiguous/consecutive span of nucleotides includes at least 8 consecutive nucleotides of at least one of the sequences set forth in SEQ ID NOs: 1, 2, 3 or 4. Labeled probes or primers can also comprise any one of SEQ ID NOs: 1, 2, 3, 4 or 8-187 or at least 8 consecutive nucleotides of any one of the sequences set forth in SEQ ID NOs: 1, 2, 3, 4 or 8-187. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}$P, $^{35}$S, $^{3}$H, $^{125}$I) or with a molecule such as biotin, acetylaminofluorene, digoxigenin, 5-bromodeoxyuridine, or fluorescein to provide probes that can be used in numerous applications.

Polynucleotides of the subject invention can also be used for the qualitative and quantitative analysis of gene expression using arrays or polynucleotides that are attached to a solid support. As used herein, the term array means a one-, two-, or multi-dimensional arrangement of polynucleotides of sufficient length to permit specific detection of gene expression. Preferably, the fragments are at least 15 nucleotides in length and the array contains at least one of SEQ ID NOs: 1, 2, 3, 4, 5, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 108, 110, 111, 112, 113, 114, 115, 116, 117, 118, 119, 120, 121, 122, 123, 124, 125, 126, 127, 128, 129, 120, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, or 186 or any combination thereof (for example, various non-limiting examples are: SEQ ID NO: 1 only, SEQ ID NO: 2 only, SEQ ID NO: 3 only, SEQ ID NO: 4 only, SEQ ID NOs: 1 and 2; SEQ ID NOs: 1 and 3; SEQ ID NOs: 1 and 4; SEQ ID NOs: 2 and 3; SEQ ID NOs: 2 and 4; SEQ ID NOs: 3 and 4 SEQ ID NOs: 1, 2 and 3; SEQ ID NOs: 1, 3 and 4; SEQ ID NOs: 2, 3 and 4; or SEQ ID NOs: 1, 2, 3 and 4). More preferably, the fragments are at least 100 nucleotides in length. More preferably, the fragments are more than 100 nucleotides in length. In some embodiments the fragments may be more than 500 nucleotides in length.

For example, quantitative analysis of gene expression may be performed with full-length polynucleotides of the subject invention, or fragments thereof, in a complementary DNA microarray as described by Schena et al. (*Science* 270:467-470, 1995; *Proc. Natl. Acad. Sci. U.S.A.* 93:10614-10619, 1996). Polynucleotides, or fragments thereof, are amplified by PCR and arrayed onto silylated microscope slides. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

mRNA is isolated from a biological sample and probes are prepared by a single round of reverse transcription. Probes are hybridized to 1 cm$^2$ microarrays under a 14×14 mm glass coverslip for 6-12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of the polynucleotides present in a biological sample can also be performed in complementary DNA arrays as described by Pietu et al. (Genome Research 6:492-503, 1996). The polynucleotides of the invention, or fragments thereof, are PCR amplified and spotted on membranes. Then, mRNAs originating from biological samples derived from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, the polynucleotide sequences of to the invention may also be used in analytical systems, such as DNA chips. DNA chips and their uses are well known in the art and (see for example, U.S. Pat. Nos. 5,561,071; 5,753,439; 6,214,545; Schena et al., *BioEssays,* 1996, 18:427-431; Bianchi et al., *Clin. Diagn. Virol.,* 1997, 8:199-208; each of which is hereby incorporated by reference in their entireties) and/or are provided by commercial vendors such as Affymetrix, Inc. (Santa Clara, Calif.). In addition, the nucleic acid sequences of the subject invention can be used as molecular weight markers in nucleic acid analysis procedures.

The term "biological sample" is used to denote a sample derived from an individual or milk-producing animal as defined herein. Such samples include blood samples, serum samples, cellular blood components, milk (milk from an individual or pooled milk from a plurality of individuals), other bodily fluids, fecal samples or tissue samples (e.g., tissue biopsies).

The terms "bulk milk sample" and "bulk tank milk sample" (BTM sample) are used interchangeably herein to refer to samples of pooled milk (milk from a plurality of animals, such as from a bulk tank, but not necessarily from a bulk tank). For milking groups that are too small to produce bulk tank quantities of milk, 10 ccs of milk may be obtained from each of the teats (e.g., four teats) and pooled with the same volume of samples of milk from every other animal (e.g., 40 cc). After mixing, a bulk tank equivalent sample can be drawn for IS1311 analysis (e.g., Step C). Thus, a bulk milk sample or BTM sample is inclusive of such a pooled sample.

The terms "individual" and "subject" are used interchangeably herein to indicate any non-human animal or human individual that is or may become infected by Map (i.e., a species susceptible to Map infection). In some embodiments, individuals are suspected of being infected by Map. Thus, various non-limiting examples of "individuals" include apes, chimpanzees, orangutans, humans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, giant pandas, hyena, seals, sea lions, and elephant seals. Reptiles include, and are not limited to, alligators, crocodiles, turtles, tortoises, snakes, iguanas, and/or other lizards. Avian species include, and are not limited to, chickens, turkeys, pigeons, quail, parrots, macaws, dove, Guinea hens, lovebirds, parakeets, flamingos, eagles, hawks, falcons, condor, ostriches, peacocks, ducks, and swans. In some embodiments, an individual is a milk-producing animal.

The term "milk-producing animal" is used herein to indicate any non-human milk-producing animal, including mammals such as cows, sheep, goats, llamas, buffalo, camels, and yaks.

Prior to conducting an assay for MAP-specific nucleic acids, nucleic acid can be purified from a biological sample if desired. Commercially available kits can be used, according to the manufacturer's recommendations, in the preparation for DNA samples for PCR based methods provided by the subject application. One such kit is the POWERSOIL Soil DNA Extraction Kit (MO BIO Laboratories, Inc., Carlsbad, Calif.). This kit is disclosed in United States Patent Application Publication No. 20050282202A1, Brolaski et al., published Dec. 22, 2005 and in PCT application PCT/US05/17933, Brolaski et al. (PCT publication WO/2006/073472), published Jul. 13, 2006. The disclosure of each of these published applications is hereby incorporated by reference in their entireties and for all purposes. Other methods suitable for purifying nucleic acids from various biological samples can also be used (see, for example, the DNA purification methods discussed in "A rapid, automated protocol for detection of *Mycobacterium avian* subsp. *paratuberculosis* in bovine feces and tissues", Tallec et al., Qiagen News, Issue 6, 2002).

As used herein, the term "FUIDI #1" (or FUIDI #1 test, or FUIDI#1 Map ELISA test) refers to an ELISA that identifies whether a given animal has been infected with Map and the corresponding degree of antigen-induced serological response. The FUIDI #1 Map ELISA test is the first step in refining for the dairy producers animals requiring selective monitoring. Serial FUIDI #1 testing identifies infected animals that achieved successful termination of Map replication and can be retained in product with semi-annual or annual serological testing. As with the current commercial Map ELISA tests, the FUIDI #1 Map ELISA test has a cut-off value that identifies within a less than one standard deviation animals with an increased probability of progression to clinical disease. The FUIDI #1 ELISA tests deviate from the antigenic array used in the IDEXX and Prionic Map ELISA tests. In the 2009 USDA Laboratory Certification Test, the FUIDI #1 Map ELISA test had a perfect score.

As used herein, the term "FUIDI #2" (or FUIDI #2 test, or FUIDI#2 Map ELISA test) refers to a test developed to differentiate animals experiencing active organism replication from those animals that have achieved organism immune capture. Done concomitantly with the FUIDI #1 test, the dairy producer has the ability to achieve four time-limited goals:

1) The test narrows the number of infected animals identified by the FUIDI #1 test to those cows whose milk will require testing before being cleared for human consumption.
2) Through serial testing of animals with active infection, the FUIDI #2 allows a producer to identify the animals with low level titer that achieve termination of Map replication. As with the FUIDI #1 low titer animals without active infection, it is theorized that the progeny of animals will be better able to handle environmental challenges by pathogenic mycobacteria than animals that do not exhibit a comparable ability
3) The test identifies animals at risk for impending clinical disease.
4) The test identifies animals with active infection whose milk needs to be effectively monitored.

Animals with high FUIDI #1 titers but who are FUIDI #2 negative, if subjected to environmental or dietary stress appear to have the potential for reactivation of organism replication at parturition.

A positive FUIDI #1 Map ELISA Test indicates prior antigenic contact, but does not distinguish between a prior infection whose organism replication has been arrested by the host's cell-mediated immunity and ongoing active infection. A positive FUIDI #2 Map ELISA test is indicative of recent or on-going *mycobacterium* synthesis. Early identification of progressive active infection using the FUIDI #2 test permits a producer to cull an animal before the disease process affects slaughter weight, institute a pregnancy or, if pregnant, resort to alternative intervention to enhance cell-mediated immunity.

In various aspects of the methods of the invention, the MAP infection can be a subclinical infection, the individual can be a cow or other milk-producing animal, and the biological sample can be blood, fecal material or milk. The term "subclinical" is meant as not displaying signs of a disease that are detectable by conventional veterinary or medical examination. In comparison, the term "clinical" means displaying signs of a disease that are detectable by conventional veterinary or medical examination, e.g., rapid weight loss and diarrhea despite good appetite.

In other embodiments, the subject invention provides for diagnostic assays based upon Western blot formats or standard immunoassays known to the skilled artisan that detect antibodies specific for *Mycobacterial* spp. For example, assays such as enzyme linked immunosorbent assays (ELISAs), radioimmunoassays (RIAs), lateral flow assays, reversible flow chromatographic binding assay (see, for example, U.S. Pat. No. 5,726,010, which is hereby incorporated by reference in its entirety), immunochromatographic strip assays, automated flow assays, and assays utilizing peptide- or antibody-containing biosensors may be employed for the detection of antibodies in the sera of animals/individuals having Johne's Disease.

Assays useful in carrying out the steps of the invention and methods for conducting the assays are well-known in the art and the methods may test biological samples (e.g., serum, plasma, blood, or milk (from a single individual or pooled milk)) qualitatively (e.g., presence or absence of antibodies or nucleic acid sequences) or quantitatively (e.g., comparison of a sample against a standard curve prepared using an antibody standard or nucleic acid standard).

Thus, the subject invention provides a method of identifying animals that have Johne's Disease comprising contacting a test sample with a crude soluble protoplasmic antigen of *M. avium* detecting the presence of an antibody-antigen complex. A test sample can comprise serum or milk from an individual.

The antibody-based assays can be considered to be of four types: direct binding assays, sandwich assays, competition assays, and displacement assays. In a direct binding assay, either the antibody or antigen is labeled, and there is a means of measuring the number of complexes formed. In a sandwich assay, the formation of a complex of at least three components (e.g., antibody-antigen-antibody) is measured. In a competition assay, labeled antigen and unlabeled antigen compete for binding to the antibody, and either the bound or the free component is measured. In a displacement assay, the labeled antigen is pre-bound to the antibody, and a change in signal is measured as the unlabeled antigen displaces the bound, labeled antigen from the receptor.

Lateral flow assays can be conducted according to the teachings of U.S. Pat. No. 5,712,170 and the references cited therein. U.S. Pat. No. 5,712,170 and the references cited therein are hereby incorporated by reference in their entireties. Displacement assays and flow immunosensors useful for carrying out displacement assays are described in: (1) Kusterbeck et al., "Antibody-Based Biosensor for Continuous Monitoring", in Biosensor Technology, R. P. Buck et al., eds., Marcel Dekker, N.Y. pp. 345-350 (1990); Kusterbeck et al., "A Continuous Flow Immunoassay for Rapid and Sensitive Detection of Small Molecules", Journal of Immunological Methods, vol. 135, pp. 191-197 (1990); Ligler et al., "Drug Detection Using the Flow Immunosensor", in Biosensor Design and Application, J. Findley et al., eds., American Chemical Society Press, pp. 73-80 (1992); and Ogert et al., "Detection of Cocaine Using the Flow Immunosensor", Analytical Letters, vol. 25, pp. 1999-2019 (1992), all of which are incorporated herein by reference in their entireties. Displacement assays and flow immunosensors are also described in U.S. Pat. No. 5,183,740, which is also incorporated herein by reference in its entirety. The displacement immunoassay, unlike most of the competitive immunoassays used to detect small molecules, can generate a positive signal with increasing antigen concentration.

Labels suitable for use in these detection methodologies include, and are not limited to 1) radioactive labels, 2) enzyme labels, 3) chemiluminescent labels, 4) fluorescent labels, 5) magnetic labels, or other suitable labels, including those set forth below. These methodologies and labels are well known in the art and widely available to the skilled artisan. Likewise, methods of incorporating labels into the nucleic acids are also well known to the skilled artisan. For example, antibodies can be labeled with a radioactive element ($^{32}$P, $^{35}$S, $^{3}$H, $^{125}$I) or with a molecule such as biotin, acetylaminofluorene, digoxigenin, 5-bromo-deoxyuridine, peroxidase, fluorescein or other labels generally known to the skilled artisan.

METHODS AND MATERIALS

Various non-limiting embodiments provided by the subject invention include:

Embodiment 1. A composition of matter comprising:
(a) a PCR primer set specific for *Mycobacterium avium* subsp. *paratuberculosis* (MAP) comprising the primers identified in any one of the following primer sets:

| Primer Set | SEQ ID NOs: | |
|---|---|---|
| 1 | 1 | 2 |
| 2 | 3 | 4 |
| 3 | 8 | 9 |
| 4 | 11 | 12 |
| 5 | 14 | 15 |
| 6 | 17 | 18 |
| 7 | 20 | 21 |
| 8 | 23 | 24 |
| 9 | 26 | 27 |
| 10 | 29 | 30 |
| 11 | 32 | 33 |
| 12 | 35 | 36 |
| 13 | 38 | 39 |
| 14 | 41 | 42 |
| 15 | 44 | 45 |
| 16 | 47 | 48 |
| 17 | 50 | 51 |
| 18 | 53 | 54 |
| 19 | 56 | 57 |
| 20 | 59 | 60 |
| 21 | 62 | 63 |
| 22 | 65 | 66 |
| 23 | 68 | 69 |
| 24 | 71 | 72 |
| 25 | 74 | 75 |
| 26 | 77 | 78 |
| 27 | 80 | 81 |
| 28 | 83 | 84 |
| 29 | 86 | 87 |
| 30 | 89 | 90 |
| 31 | 92 | 93 |
| 32 | 95 | 96 |
| 33 | 98 | 99 |

-continued

| Primer Set | SEQ ID NOs: | |
|---|---|---|
| 34 | 101 | 102 |
| 35 | 104 | 105 |
| 36 | 107 | 108 |
| 37 | 110 | 111 |
| 38 | 113 | 114 |
| 39 | 116 | 117 |
| 40 | 119 | 120 |
| 41 | 122 | 123 |
| 42 | 125 | 126 |
| 43 | 128 | 129 |
| 44 | 131 | 132 |
| 45 | 134 | 135 |
| 46 | 137 | 138 |
| 47 | 140 | 141 |
| 48 | 143 | 144 |
| 49 | 146 | 147 |
| 50 | 149 | 150 |
| 51 | 152 | 153 |
| 52 | 155 | 156 |
| 53 | 158 | 159 |
| 54 | 161 | 162 |
| 55 | 164 | 165 |
| 56 | 167 | 168 |
| 57 | 170 | 171 |
| 58 | 173 | 174 |
| 59 | 176 | 177 |
| 60 | 179 | 180 |
| 61 | 182 | 183 |
| 62 | 185 | 186 |
| 63 | 188 | 189 |
| 64 | 191 | 192 |
| 65 | 194 | 195 |
| 66 | 197 | 198 |
| 67 | 200 | 201 |
| 68 | 203 | 204 |
| 69 | 205 | 206 |
| 70 | 207 | 208 |
| 71 | 209 | 210 |
| 72 | 211 | 212 |

(b) a PCR primer set specific for *Mycobacterium avium* subsp. *paratuberculosis* (MAP) comprising the primers identified in any one of the following primer sets:

| Primer Set | SEQ ID NO: |
|---|---|
| 73 | 8, 9 and 10 |
| 74 | 11, 12 and 13 |
| 75 | 14, 15 and 16 |
| 76 | 17, 18 and 19 |
| 77 | 20, 21 and 22 |
| 78 | 23, 24 and 25 |
| 79 | 26, 27 and 28 |
| 80 | 29, 30 and 31 |
| 81 | 32, 33 and 34 |
| 82 | 35, 36 and 37 |
| 83 | 38, 39 and 40 |
| 84 | 41, 42 and 43 |
| 85 | 44, 45 and 46 |
| 86 | 47, 48 and 49 |
| 87 | 50, 51 and 52 |
| 88 | 53, 54 and 55 |
| 89 | 56, 57 and 58 |
| 90 | 59, 60 and 61 |
| 91 | 62, 63 and 64 |
| 92 | 65, 66 and 67 |
| 93 | 68, 69 and 70 |
| 94 | 71, 72 and 73 |
| 95 | 74, 75 and 76 |
| 96 | 77, 78 and 79 |
| 97 | 80, 81 and 82 |
| 98 | 83, 84 and 85 |
| 99 | 86, 87 and 88 |
| 100 | 89, 90 and 91 |
| 101 | 92, 93 and 94 |
| 102 | 95, 96 and 97 |
| 103 | 98, 99 and 100 |
| 104 | 101, 102 and 103 |
| 105 | 104, 105 and 106 |
| 106 | 107, 108 and 109 |
| 107 | 110, 111 and 112 |
| 108 | 113, 114 and 115 |
| 109 | 116, 117 and 118 |
| 110 | 119, 120 and 121 |
| 111 | 122, 123 and 124 |
| 112 | 125, 126 and 127 |
| 113 | 128, 129 and 130 |
| 114 | 131, 132 and 133 |
| 115 | 134, 135 and 136 |
| 116 | 137, 138 and 139 |
| 117 | 140, 141 and 142 |
| 118 | 143, 144 and 145 |
| 119 | 146, 147 and 148 |
| 120 | 149, 150 and 151 |
| 121 | 152, 153 and 154 |
| 122 | 155, 156 and 157 |
| 123 | 158, 159 and 160 |
| 124 | 161, 162 and 163 |
| 125 | 164, 165 and 166 |
| 126 | 167, 168 and 169 |
| 127 | 170, 171 and 172 |
| 128 | 173, 174 and 175 |
| 129 | 176, 177 and 178 |
| 130 | 179, 180 and 181 |
| 131 | 182, 183 and 184 |
| 132 | 185, 186 and 187 |
| 133 | 188, 189 and 190 |
| 134 | 191, 192 and 193 |
| 135 | 194, 195 and 196 |
| 136 | 197, 198 and 199 |
| 137 | 200, 201 and 202 |

(c) a PCR primer set specific for *Mycobacterium avium* subsp. *paratuberculosis* (MAP) comprising the following combinations of primers:

| Combinations of Primers (SEQ ID NOs:) | |
|---|---|
| 8 and 9 and | 38 and 39; |
| | 41 and 42; |
| | 44 and 45; |
| | 47 and 48; or |
| | 50 and 51 |
| 11 and 12 and | 53 and 54; |
| | 56 and 57; |
| | 59 and 60; |
| | 62 and 63; or |
| | 65 and 66 |
| 14 and 15 and | 68 and 69; |
| | 71 and 72; |
| | 74 and 75; |
| | 77 and 78; or |
| | 80 and 81 |
| 17 and 18 and | 83 and 84; |
| | 86 and 87; |
| | 89 and 90; |
| | 92 and 93; or |
| | 95 and 96 |
| 20 and 21 and | 98 and 99; |
| | 101 and 102; |
| | 104 and 105; |
| | 107 and 108; or |
| | 110 and 111 |
| 23 and 24 and | 113 and 114; |
| | 116 and 117; |

| Combinations of Primers (SEQ ID NOs:) | |
|---|---|
| 26 and 27 and | 119 and 120; |
| | 122 and 123; or |
| | 125 and 126 |
| | 128 and 129; |
| | 131 and 132; |
| | 134 and 135; |
| | 137 and 138; or |
| | 140 and 141 |
| 29 and 30 and | 143 and 144; |
| | 146 and 147; |
| | 149 and 150; |
| | 152 and 153; or |
| | 155 and 156 |
| 32 and 33 and | 158 and 159; |
| | 161 and 162; |
| | 164 and 165; |
| | 167 and 168; or |
| | 170 and 171 |
| 35 and 36 and | 173 and 174; |
| | 176 and 177; |
| | 179 and 180; |
| | 182 and 183; or |
| | 185 and 186 |
| 188 and 189 and | 203 and 204; |
| | 205 and 206; |
| | 207 and 208; |
| | 209 and 210; or |
| | 211 and 212 |
| 191 and 192 and | 203 and 204; |
| | 205 and 206; |
| | 207 and 208; |
| | 209 and 210; or |
| | 211 and 212 |
| 194 and 195 and | 203 and 204; |
| | 205 and 206; |
| | 207 and 208; |
| | 209 and 210; or |
| | 211 and 212 |
| 197 and 198 and | 203 and 204; |
| | 205 and 206; |
| | 207 and 208; |
| | 209 and 210; or |
| | 211 and 212; or |
| 200 and 201 and | 203 and 204; |
| | 205 and 206; |
| | 207 and 208; |
| | 209 and 210; or |
| | 211 and 212 |

(d) a PCR primer set specific for *Mycobacterium avium* subsp. *paratuberculosis* (MAP) comprising the following combinations of primers:

| Combinations of Primers (SEQ ID NOs:) | |
|---|---|
| 8 and 9 and 10 and | 38 and 39; |
| | 41 and 42; |
| | 44 and 45; |
| | 47 and 48; or |
| | 50 and 51 |
| 11 and 12 and 13 and | 53 and 54; |
| | 56 and 57; |
| | 59 and 60; |
| | 62 and 63; or |
| | 65 and 66 |
| 14 and 15 and 16 and | 68 and 69; |
| | 71 and 72; |
| | 74 and 75; |
| | 77 and 78; or |
| | 80 and 81 |
| 17 and 18 and 19 | 83 and 84; |
| | 86 and 87; |
| | 89 and 90; |
| | 92 and 93; or |
| | 95 and 96 |
| 20 and 21 and 22 and | 98 and 99; |
| | 101 and 102; |
| | 104 and 105; |
| | 107 and 108; or |
| | 110 and 111 |
| 23 and 24 and 25 and | 113 and 114; |
| | 116 and 117; |
| | 119 and 120; |
| | 122 and 123; or |
| | 125 and 126 |
| 26 and 27 and 28 and | 128 and 129; |
| | 131 and 132; |
| | 134 and 135; |
| | 137 and 138; or |
| | 140 and 141 |
| 29 and 30 and 31 and | 143 and 144; |
| | 146 and 147; |
| | 149 and 150; |
| | 152 and 153; or |
| | 155 and 156 |
| 32 and 33 and 34 and | 158 and 159; |
| | 161 and 162; |
| | 164 and 165; |
| | 167 and 168; or |
| | 170 and 171 |
| 35 and 36 and | 173 and 174; |
| | 176 and 177; |
| | 179 and 180; |
| | 182 and 183; or |
| | 185 and 186 |
| 188 and 189 and 190 and | 203 and 204; |
| | 205 and 206; |
| | 207 and 208; |
| | 209 and 210; or |
| | 211 and 212 |
| 191 and 192 and 193 and | 203 and 204; |
| | 205 and 206; |
| | 207 and 208; |
| | 209 and 210; or |
| | 211 and 212 |
| 194 and 195 and 196 and | 203 and 204; |
| | 205 and 206; |
| | 207 and 208; |
| | 209 and 210; or |
| | 211 and 212 |
| 197 and 198 and 199 and | 203 and 204; |
| | 205 and 206; |
| | 207 and 208; |
| | 209 and 210; or |
| | 211 and 212; or |
| 200 and 201 and 202 and | 203 and 204; |
| | 205 and 206; |
| | 207 and 208; |
| | 209 and 210; or |
| | 211 and 212 |

(e) a PCR primer set specific for *Mycobacterium avium* subsp. *paratuberculosis* (MAP) comprising the following combinations of primers:

| Combinations of Primers (SEQ ID NOs:) | |
|---|---|
| 8 and 9 and | 38 and 39 and 40; or |
| | 41 and 42 and 43; or |
| | 44 and 45 and 46; or |
| | 47 and 48 and 49; or |
| | 50 and 51 and 52 |
| 11 and 12 and | 53 and 54 and 55; or |
| | 56 and 57 and 58; or |
| | 59 and 60 and 61; or |
| | 62 and 63 and 64; or |
| | 65 and 66 and 67 |

-continued

| Combinations of Primers (SEQ ID NOs:) | |
|---|---|
| 14 and 15 and | 68 and 69 and 70; or |
| | 71 and 72 and 73; or |
| | 74 and 75 and 76; or |
| | 77 and 78 and 79; or |
| | 80 and 81 and 82 |
| 17 and 18 and | 83 and 84 and 85; or |
| | 86 and 87 and 88; or |
| | 89 and 90 and 91; or |
| | 92 and 93 and 94; or |
| | 95 and 96 and 97 |
| 20 and 21 and | 98 and 99 and 100; or |
| | 101 and 102 and 103; or |
| | 104 and 105 and 106; or |
| | 107 and 108 and 109; or |
| | 110 and 111 and 112 |
| 23 and 24 and | 113 and 114 and 115; or |
| | 116 and 117 and 118; or |
| | 119 and 120 and 121; or |
| | 122 and 123 and 124; or |
| | 125 and 126 and 127 |
| 26 and 27 and | 128 and 129 and 130; or |
| | 131 and 132 and 133; or |
| | 134 and 135 and 136; or |
| | 137 and 138 and 139; or |
| | 140 and 141 and 142 |
| 29 and 30 and | 143 and 144 and 145; or |
| | 146 and 147 and 148; or |
| | 149 and 150 and 151; or |
| | 152 and 153 and 154; or |
| | 155 and 156 and 157 |
| 32 and 33 and | 158 and 159 and 160; or |
| | 161 and 162 and 163; or |
| | 164 and 165 and 166; or |
| | 167 and 168 and 169; or |
| | 170 and 171 and 172 |
| 35 and 36 and | 173 and 174 and 175; or |
| | 176 and 177 and 178; or |
| | 179 and 180 and 181; or |
| | 182 and 183 and 184; or |
| | 185 and 186 and 187 |

(f) a PCR primer set specific for *Mycobacterium avium* subsp. *paratuberculosis* (MAP) comprising the following combinations of primers:

| Combinations of Primers (SEQ ID NOs:) | |
|---|---|
| 8 and 9 and 10 and | 38 and 39 and 40; or |
| | 41 and 42 and 43; or |
| | 44 and 45 and 46; or |
| | 47 and 48 and 49; or |
| | 50 and 51 and 52 |
| 11 and 12 and 13 and | 53 and 54 and 55; or |
| | 56 and 57 and 58; or |
| | 59 and 60 and 61; or |
| | 62 and 63 and 64; or |
| | 65 and 66 and 67 |
| 14 and 15 and 16 and | 68 and 69 and 70; or |
| | 71 and 72 and 73; or |
| | 74 and 75 and 76; or |
| | 77 and 78 and 79; or |
| | 80 and 81 and 82 |
| 17 and 18 and 19 and | 83 and 84 and 85; or |
| | 86 and 87 and 88; or |
| | 89 and 90 and 91; or |
| | 92 and 93 and 94; or |
| | 95 and 96 and 97 |
| 20 and 21 and 22 and | 98 and 99 and 100; or |
| | 101 and 102 and 103; or |
| | 104 and 105 and 106; or |
| | 107 and 108 and 109; or |
| | 110 and 111 and 112 |
| 23 and 24 and 25 and | 113 and 114 and 115; or |
| | 116 and 117 and 118; or |
| | 119 and 120 and 121; or |
| | 122 and 123 and 124; or |
| | 125 and 126 and 127 |
| 26 and 27 and 28 and | 128 and 129 and 130; or |
| | 131 and 132 and 133; or |
| | 134 and 135 and 136; or |
| | 137 and 138 and 139; or |
| | 140 and 141 and 142 |
| 29 and 30 and 31 and | 143 and 144 and 145; or |
| | 146 and 147 and 148; or |
| | 149 and 150 and 151; or |
| | 152 and 153 and 154; or |
| | 155 and 156 and 157 |
| 32 and 33 and 34 and | 158 and 159 and 160; or |
| | 161 and 162 and 163; or |
| | 164 and 165 and 166; or |
| | 167 and 168 and 169; or |
| | 170 and 171 and 172 |
| 35 and 36 and 37 and | 173 and 174 and 175; or |
| | 176 and 177 and 178; or |
| | 179 and 180 and 181; or |
| | 182 and 183 and 184; or |
| | 185 and 186 and 187 |

(g) an isolated polynucleotide comprising any one of SEQ ID NOs: 1 through 212 or an isolated polynucleotide comprising at least 8 consecutive nucleotides of any one of SEQ ID NOs: 1 through 212;

(h) an isolated polynucleotide comprising at least 8 consecutive nucleotides of any one of SEQ ID NOs: 1 through 212, wherein said polynucleotide has a maximum length that is equal to the number of nucleotides associated with said specific SEQ ID NO:;

(i) an isolated polynucleotide that is fully complementary to:
  (1) any one of SEQ ID NO: 1 through 212;
  (2) a polynucleotide comprising at least 8 consecutive nucleotides of any one of SEQ ID NOs: 1 through 212; or
  (3) a polynucleotide comprising at least 8 consecutive nucleotides of any one of SEQ ID NOs: 1 through 212, wherein said polynucleotide has a maximum length that is equal to the number of nucleotides associated with said specific SEQ ID NO:; or (j) an isolated polynucleotide comprising a contiguous/consecutive span of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 consecutive nucleotides of SEQ ID NO: 5, 7 or 213 provided that said contiguous/consecutive span of nucleotides includes at least 8 consecutive nucleotides of a primer or probe selected from any one of SEQ ID NOs: 1-4 and 8-212 or polynucleotides fully complementary to any one of SEQ ID NOs: 1-4 and 8-212.

Embodiment 2. The primer set or isolated polynucleotide according to embodiment 1, wherein one or more of said primers is labeled or said polynucleotide is labeled.

Embodiment 3. The primer set or isolated polynucleotide according to embodiment 2, wherein said label is a fluorescent label.

Embodiment 4. The primer set or isolated polynucleotide according to embodiment 2, wherein said label is a radioisotope.

Embodiment 5. The primer set or isolated polynucleotide according to embodiment 2, wherein said label is biotin.

Embodiment 6. A method of detecting the presence of *Mycobacterium avium* subsp. *paratuberculosis* (MAP) in a sample from individual suspected of being infected with MAP, said method comprising the steps of:
(a) providing a sample from the individual suspected of being infected with MAP;
(b) treating the sample to solubilize the nucleic acids therein;
(c) forming a PCR reaction solution comprising:
(A) at least a portion of the solubilized nucleic acids from step (b);
(B) any one of the PCR primer sets according to embodiment 1;
(C) a mixture of nucleoside triphosphate monomers; and
(D) a PCR polymerase in a buffered solution;
(d) carrying out a polymerase chain reaction on the PCR reaction solution to amplify any MAP-specific nucleic acid which is specific for the particular primer set used to a level sufficient for detection; and
(e) detecting the presence of amplified MAP-specific nucleic acid in the resulting solution which is specific for the particular primer set used; wherein the detection of the amplified MAP-specific nucleic acid which is specific for the particular primer set used indicates that MAP is present in the individual.

Embodiment 7. The method according to embodiment 6 wherein the sample is a fecal sample from an individual.

Embodiment 8. The method according to embodiment 7, wherein said individual is a bovine.

Embodiment 9. The method according to embodiment 6, wherein the primer set comprises primer set 2.

Embodiment 10. The method according to embodiment 9, wherein the primer set further comprises SEQ ID NO: 1.

Embodiment 11. The method according to embodiment 9, wherein the primer set further comprises SEQ ID NO: 2.

Embodiment 12. The method according to embodiment 9, wherein the primer set further comprises SEQ ID NO: 1 and SEQ ID NO: 2.

Embodiment 13. The method according to embodiment 6, wherein the primer set comprises a polynucleotide comprising at least 8 contiguous nucleotides of SEQ ID NO: 3 and a polynucleotide comprising at least 8 contiguous nucleotides of SEQ ID NO: 4.

Embodiment 14. The method according to embodiment 13, wherein the primer set further comprises a polynucleotide comprising at least 8 contiguous nucleotides of SEQ ID NO: 1.

Embodiment 15. The method according to embodiment 13, wherein the primer set further comprises a polynucleotide comprising at least 8 contiguous nucleotides of SEQ ID NO: 2.

Embodiment 16. The method according to embodiment 13, wherein the primer set further comprises a polynucleotide comprising at least 8 contiguous nucleotides of SEQ ID NO: 1 and a polynucleotide comprising at least 8 contiguous nucleotides of SEQ ID NO: 2.

Embodiment 17. The method according to embodiment 6, wherein the detection of the presence of amplified MAP-specific nucleic acid comprises gel electrophoresis of the amplified MAP-specific nucleic acid solution and staining of the resulting gel to visualize the band of the MAP-specific nucleic acid specific for the particular primer set used.

Embodiment 18. The method according to embodiment 17, wherein at least one of the oligonucleotides in the primer set or at least one of the nucleoside triphosphate monomers contains a label which will be incorporated into the amplified MAP-specific nucleic acid and can be used for the detection of the amplified MAP-specific nucleic acid.

Embodiment 19. A method of detecting the presence of MAP in a sample from individual suspected of being infected with MAP using a nested PCR procedure, said method comprising the steps of:
(a) providing a sample from the individual suspected of being infected with MAP;
(b) treating the sample to solubilize the nucleic acids therein;
(c) forming a first PCR reaction solution containing at least a portion of the solubilized nucleic acids from step (b), a first PCR primer set, a first mixture of nucleoside triphosphate monomers, and a first PCR polymerase in a first buffered solution, wherein the first primer set comprises a first pair of oligonucleotides as set forth in primer set 1, 3, 4, 5, 6, 7, 8, 9, 10, 11, 12, 63, 64, 65, 66 or 67 or fragments of said first pair of oligonucleotides that are at least 8 consecutive nucleotides in length;
(d) performing a first polymerase chain reaction on the first PCR reaction solution to amplify any MAP-specific nucleic acid which is specific for the first primer set used;
(e) forming a second PCR reaction solution containing at least a portion of the PCR-reacted first PCR reaction solution from step (d), a second PCR primer set, a second mixture of nucleoside triphosphate monomers, and a second PCR polymerase in a second buffered solution, wherein the second primer set comprises a second pair of oligonucleotides as set forth in primer set 2, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 68, 69, 70, 71 or 72 or fragments of said second pair of oligonucleotides that are at least 8 consecutive nucleotides in length;
(f) performing a second polymerase chain reaction on the second PCR reaction solution to amplify any MAP-specific nucleic acid which is specific for the second primer set used to a level sufficient for detection; and
(g) detecting the presence of amplified MAP-specific nucleic acid in the resulting solution from step (f) which specific for the second primer set; wherein the detection of the amplified MAP-specific nucleic acid which is specific for the second primer set indicates that MAP is present in the individual.

Embodiment 20. The method according to embodiment 19, wherein the sample is a fecal sample from said individual.

Embodiment 21. The method according to embodiment 20, wherein said individual is a bovine.

Embodiment 22. The method according to embodiment 19, wherein the detection in step (g) comprises gel electrophoresis of the amplified MAP-specific nucleic acid solution and staining of the resulting gel to visualize the MAP-specific nucleic acid on the gel.

Embodiment 23. The method according to embodiment 19, wherein either the primers, or one or more of the monomers, or both, employed in steps (c) and (e) contains a label whereby the amplified MAP-specific nucleic acid that results in step (f) contains the label, and the detection in step (g) comprises detecting the presence of the label.

Embodiment 24. The method according to embodiment 19, wherein said first primer set comprises the oligonucleotides of primer set 1 (SEQ ID NO: 1 and 2) or fragments of SEQ ID NO:1 and SEQ ID NO:2 that comprise at least 8 contiguous nucleotides of SEQ ID NOs:1 and 2.

Embodiment 25. The method according to embodiment 19, wherein said second primer set comprises the oligonucleotides of primer set 2 (SEQ ID NOs: 3 and 4) or fragments of SEQ ID NO:3 and SEQ ID NO:4 that comprise at least 8 contiguous nucleotides of SEQ ID NOs:3 and 4.

Embodiment 26. The method according to embodiment 19, wherein said first primer set comprises fragments of at least 8 consecutive nucleotides of SEQ ID NOs:1 and 2 and said second primer set comprises fragments of at least 8 consecutive nucleotides of SEQ ID NOs:3 and 4.

Embodiment 27. An improvement in a PCR-based method of detecting the presence of *Mycobacterium avium* subsp. *paratuberculosis* (MAP) in a sample from individual suspected of being infected with MAP, wherein the improvement comprises the use of a polynucleotide or primer set as set forth in embodiment 1.

Embodiment 28. A method of identifying animals having Johne's Disease comprising:
a) obtaining sera from an animal suspected of having Johne's disease;
b) contacting a crude soluble protoplasmic antigen of *M. avium* with sera from said animal (test sera) and a control sera; and
c) detecting the binding of antibodies to said crude protoplasmic antigen, wherein an animal having Johne's disease is identified when the amount of test sera antibody bound to the crude soluble antigen is greater than the amount of a control sera antibody bound to said crude soluble antigen.

Embodiment 29. The method according to embodiment 27, wherein the sera obtained from said animal has been pre-absorbed with *Mycobacterium pheli*.

Embodiment 30. The method according to embodiment 27 or 28, wherein said detecting comprises contacting the antibodies of said test sera and said control sera with a labeled antibody.

Embodiment 31. The method according to embodiment 29, wherein said antibody is labeled with an fluorophore, an enzyme, or a radiolabel.

Embodiment 32. The method according to any one of embodiments 6 through 27, further comprising the detection of amplified gene product with a probe.

Embodiment 33. The method according to embodiment 32, wherein said probe comprises a label that is a fluorescent dye or radiolabel.

Embodiment 34. The method according to embodiment 33, wherein said probe comprises a fluorescent dye and a quencher.

Embodiment 35. The method according to embodiment 34, wherein probe is 5'-/56-FAM/CAC ACT GTC GAC GAT CGC/31ABlkFQ/-3'.

Primers and combinations of primers that are suitable for use in the practice of the PCR based methods set forth herein are the various oligonucleotides identified as a "primer" in the tables that are set forth below.

| F Primers | Sequence | SEQ ID NO: | Possible Member of Primer Set No. |
|---|---|---|---|
| C:\Documents and Settings\ChrisE\Local Settings\Temporary Internet Files\OLK1\primer3_www_results_help.cgi -PRIMER_THREEPrimer F1 | gtcattcagaatcgctgcaa | 8 | 3 or 73 |
| Primer F2 | tggcgtcagctattggtgta | 9 | 3 or 73 |
| Probe F1F2 | aactcgaacacacctgggac | 10 | 3 or 73 |
| Primer F3 | tcctctccttcgtcaccaac | 11 | 4 or 74 |
| Primer F4 | atgaaatgggcgtctaccag | 12 | 4 or 74 |
| Probe F3F4 | gtcattcagaatcgctgcaa | 13 | 4 or 74 |
| Primer F5 | gtcattcagaatcgctgcaa | 14 | 5 or 75 |
| Primer F6 | cgtcagctattggtgtaccg | 15 | 5 or 75 |
| Probe F5F6 | aactcgaacacacctgggac | 16 | 5 or 75 |
| Primer F7 | cattcagaatcgctgcaatc | 17 | 6 or 76 |
| Primer F8 | tggcgtcagctattggtgta | 18 | 6 or 76 |
| Probe F7F8 | aactcgaacacacctgggac | 19 | 6 or 76 |
| Primer F9 | agaatcgctgcaatctcagg | 20 | 7 or 77 |
| Primer F10 | tggcgtcagctattggtgta | 21 | 7 or 77 |
| Probe F9F10 | aactcgaacacacctgggac | 22 | 7 or 77 |

| M primers | Sequence | SEQ ID NO: | Possible Member of Primer Set No. |
|---|---|---|---|
| Primer M1 | cgaatcgcgttacatcacag | 23 | 8 or 78 |
| Primer M2 | gaaaccacgttgcgagtacc | 24 | 8 or 78 |
| Probe M1M2 | taccgactgagctacctggc | 25 | 8 or 78 |
| Primer M3 | atcacaggtcttccggtcac | 26 | 9 or 79 |

| M primers | Sequence | SEQ ID NO: | Possible Member of Primer Set No. |
|---|---|---|---|
| Primer M4 | gaaaccacgttgcgagtacc | 27 | 9 or 79 |
| Probe M3M4 | taccgactgagctacctggc | 28 | 9 or 79 |
| Primer M5 | gacgaatcgcgttacatcac | 29 | 10 or 80 |
| Primer M6 | gaaaccacgttgcgagtacc | 30 | 10 or 80 |
| Probe M5M6 | taccgactgagctacctggc | 31 | 10 or 80 |
| Primer M7 | tcgcgttacatcacaggtct | 32 | 11 or 81 |
| Primer M8 | gaaaccacgttgcgagtacc | 33 | 11 or 81 |
| Probe M7M8 | taccgactgagctacctggc | 34 | 11 or 81 |
| Primer M9 | gaatcgcgttacatcacagg | 35 | 12 or 82 |
| Primer M10 | gaaaccacgttgcgagtacc | 36 | 12 or 82 |
| Probe M9M10 | taccgactgagctacctggc | 37 | 12 or 82 |

| Nested Primers for amplicon produced by F1 and F2 | Sequence | SEQ ID NO: | Possible Member of Primer Set No. |
|---|---|---|---|
| Primer F1F2N1 | gtcattcagaatcgctgcaa | 38 | 13 or 83 |
| Primer F1F2N2 | cgtggtctctgagtttgggta | 39 | 13 or 83 |
| Probe F1F2N1F1F2N2 | ctggtagacgcccatttcat | 40 | 13 or 83 |
| Primer F1F2N3 | gtcattcagaatcgctgcaa | 41 | 14 or 84 |
| Primer F1F2N4 | tatcgatgaaatgggcgtct | 42 | 14 or 84 |
| Probe F1F2N3F1F2N4 | cagctccagatcgtcattca | 43 | 14 or 84 |
| Primer F1F2N5 | gtcattcagaatcgctgcaa | 44 | 15 or 85 |
| Primer F1F2N6 | ccactcgtggtctctgagttt | 45 | 15 or 85 |
| Probe F1F2N5F1F2N6 | ctggtagacgcccatttcat | 46 | 15 or 85 |
| Primer F1F2N7 | gtcattcagaatcgctgcaa | 47 | 16 or 86 |
| Primer F1F2N8 | atcgatgaaatgggcgtcta | 48 | 16 or 86 |
| Probe F1F2N7F1F2N8 | cagctccagatcgtcattca | 49 | 16 or 86 |
| Primer F1F2N9 | gtcattcagaatcgctgcaa | 50 | 17 or 87 |
| Primer F1F2N10 | ctcgtgtctctgagtttgg | 51 | 17 or 87 |
| Probe F1F2N9F1F2N10 | ctggtagacgcccatttcat | 52 | 17 or 87 |

| Nested Primers for amplicon produced by F3 and F4 | Sequence | SEQ ID NO: | Possible Member of Primer Set No. |
|---|---|---|---|
| Primer F3F4N1 | gtcattcagaatcgctgcaa | 53 | 18 or 88 |
| Primer F3F4N2 | cgtggtctctgagtttgggta | 54 | 18 or 88 |
| Probe F3F4N1F3F4N2 | ctggtagacgcccatttcat | 55 | 18 or 88 |
| Primer F3F4N3 | gtcattcagaatcgctgcaa | 56 | 19 or 89 |
| Primer F3F4N4 | tatcgatgaaatgggcgtct | 57 | 19 or 89 |
| Probe F3F4N3F3F4N4 | cagctccagatcgtcattca | 58 | 19 or 89 |
| Primer F3F4N5 | gtcattcagaatcgctgcaa | 59 | 20 or 90 |
| Primer F3F4N6 | ccactcgtggtctctgagttt | 60 | 20 or 90 |
| Probe F3F4N5F3F4N6 | ctggtagacgcccatttcat | 61 | 20 or 90 |

-continued

| Nested Primers for amplicon produced by F3 and F4 | Sequence | SEQ ID NO: | Possible Member of Primer Set No. |
|---|---|---|---|
| Primer F3F4N7 | gtcattcagaatcgctgcaa | 62 | 21 or 91 |
| Primer F3F4N8 | atcgatgaaatgggcgtcta | 63 | 21 or 91 |
| Probe F3F4N7F3F4N8 | cagctccagatcgtcattca | 64 | 21 or 91 |
| Primer F3F4N9 | gtcattcagaatcgctgcaa | 65 | 22 or 92 |
| Primer F3F4N10 | ctcgtggtctctgagtttgg | 66 | 22 or 92 |
| Probe F3F4N9F3F4N10 | ctggtagacgcccatttcat | 67 | 22 or 92 |

| Nested Primers for amplicon produced by F5 and F6 | Sequence | SEQ ID NO: | Possible Member of Primer Set No. |
|---|---|---|---|
| Primer F5F6N1 | agaatcgctgcaatctcagg | 68 | 23 or 93 |
| Primer F5F6N2 | cgtggtctctgagtttgggta | 69 | 23 or 93 |
| Probe F5F6N1F5F6N2 | cgcttgaatggtcgtctgt | 70 | 23 or 93 |
| Primer F5F6N3 | agaatcgctgcaatctcagg | 71 | 24 or 94 |
| Primer F5F6N4 | cttagttcgccgcttgaatg | 72 | 24 or 94 |
| Probe F5F6N3F5F6N4 | ctggtagacgcccatttcat | 73 | 24 or 94 |
| Primer F5F6N5 | agaatcgctgcaatctcagg | 74 | 25 or 95 |
| Primer F5F6N6 | ccactcgtggtctctgagttt | 75 | 25 or 95 |
| Probe F5F6N5F5F6N6 | ctggtagacgcccatttcat | 76 | 25 or 95 |
| Primer F5F6N7 | ctgcaatctcaggcagctc | 77 | 26 or 96 |
| Primer F5F6N8 | cttagttcgccgcttgaatg | 78 | 26 or 96 |
| Probe F5F6N7F5F6N8 | ctggtagacgcccatttcat | 79 | 26 or 96 |
| Primer F5F6N9 | ctgcaatctcaggcagctc | 80 | 27 or 97 |
| Primer F5F6N10 | ttagttcgccgcttgaatg | 81 | 27 or 97 |
| Probe F5F6N9F5F6N10 | ctggtagacgcccatttcat | 82 | 27 or 97 |

| Nested Primers for amplicon produced by F7 and F8 | Sequence | SEQ ID NO: | Possible Member of Primer Set No. |
|---|---|---|---|
| Primer F7F8N1 | cagctccagatcgtcattca | 83 | 28 or 98 |
| Primer F7F8N2 | tgtcgatccgcttagttcg | 84 | 28 or 98 |
| Probe F7F8N1F7F8N2 | ctggtagacgcccatttcat | 85 | 28 or 98 |
| Primer F7F8N3 | gcattccaagtcctgaccac | 86 | 29 or 99 |
| Primer F7F8N4 | gtcccaggtgtgttcgagtt | 87 | 29 or 99 |
| Probe F7F8N3F7F8N4 | ctggtagacgcccatttcat | 88 | 29 or 99 |
| Primer F7F8N5 | cagctccagatgtcattca | 89 | 30 or 100 |
| Primer F7F8N6 | ttgtcgatccgcttagttcg | 90 | 30 or 100 |

-continued

| Nested Primers for amplicon produced by F7 and F8 | Sequence | SEQ ID NO: | Possible Member of Primer Set No. |
|---|---|---|---|
| Probe F7F8N5F7F8N6 | ctggtagacgcccatttcat | 91 | 30 or 100 |
| Primer F7F8N7 | agaatcgctgcaatctcagg | 92 | 31 or 101 |
| Primer F7F8N8 | cgcttgaatggtcgtctgt | 93 | 31 or 101 |
| Probe F7F8N7F7F8N8 | ctggtagacgcccatttcat | 94 | 31 or 101 |
| Primer F7F8N9 | agaatcgctgcaatctcagg | 95 | 32 or 102 |
| Primer F7F8N10 | cttagttcgccgcttgaatg | 96 | 32 or 102 |
| Probe F7F8N9F7F8N10 | ctggtagacgcccatttcat | 97 | 32 or 102 |

| Nested Primers for amplicon produced by F9 and F10 | Sequence | SEQ ID NO: | Possible Member of Primer Set No. |
|---|---|---|---|
| Primer F9F10N1 | cagctccagatcgtcattca | 98 | 33 or 103 |
| Primer F9F10N2 | tgtcgatccgcttagttcg | 99 | 33 or 103 |
| Probe F9F10N1F9F10N2 | ctggtagacgcccatttcat | 100 | 33 or 103 |
| Primer F9F10N3 | cagctccagatcgtcattca | 101 | 34 or 104 |
| Primer F9F10N4 | ttgtcgatccgcttagttcg | 102 | 34 or 104 |
| Probe F9F10N3F9F10N4 | ctggtagacgcccatttcat | 103 | 34 or 104 |
| Primer F9F10N5 | gcattccaagtcctgaccac | 104 | 35 or 105 |
| Primer F9F10N6 | caggtgtgttcgagttgcag | 105 | 35 or 105 |
| Probe F9F10N5F9F10N6 | ctggtagacgcccatttcat | 106 | 35 or 105 |
| Primer F9F10N7 | gcagctccagatcgtcattc | 107 | 36 or 106 |
| Primer F9F10N8 | tgtcgatccgcttagttcg | 108 | 36 or 106 |
| Probe F9F10N7F9F10N8 | ctggtagacgcccatttcat | 109 | 36 or 106 |
| Primer F9F10N9 | cagctccagatcgtcattca | 110 | 37 or 107 |
| Primer F9F10N10 | tgagaattgtcgatccgctta | 111 | 37 or 107 |
| Probe F9F10N9F9F10N10 | ctggtagacgcccatttcat | 112 | 37 or 107 |

| Nested Primers for amplicon produced by M1 and M2 | Sequence | SEQ ID NO: | Possible Member of Primer Set No. |
|---|---|---|---|
| Primer M1M2N1 | ggcagcatgctcaagtagc | 113 | 38 or 108 |
| Primer M1M2N2 | gggttcgaatcccgtagg | 114 | 38 or 108 |
| Probe M1M2N1M1M2N2 | taccgactgagctacctggc | 115 | 38 or 108 |
| Primer M1M2N3 | gcagcatgctcaagtagcc | 116 | 39 or 109 |
| Primer M1M2N4 | gggttcgaatcccgtagg | 117 | 39 or 109 |
| Probe M1M2N3M1M2N4 | taccgactgagctacctggc | 118 | 39 or 109 |
| Primer M1M2N5 | gcagcatgctcaagtagcc | 119 | 40 or 110 |

-continued

| Nested Primers for amplicon produced by M1 and M2 | Sequence | SEQ ID NO: | Possible Member of Primer Set No. |
|---|---|---|---|
| Primer M1M2N6 | ccctttcaaggcggtagc | 120 | 40 or 110 |
| Probe M1M2N5M1M2N6 | taccgactgagctacctggc | 121 | 40 or 110 |
| Primer M1M2N7 | gcagcatgctcaagtagcc | 122 | 41 or 111 |
| Primer M1M2N8 | gccctttcaaggcggtag | 123 | 41 or 111 |
| Probe M1M2N7M1M2N8 | taccgactgagctacctggc | 124 | 41 or 111 |
| Primer M1M2N9 | ggcagcatgctcaagtagc | 125 | 42 or 112 |
| Primer M1M2N10 | ccctttcaaggcggtagc | 126 | 42 or 112 |
| Probe M1M2N9M1M2N10 | taccgactgagctacctggc | 127 | 42 or 112 |

| Nested Primers for amplicon produced by M3 and M4 | Sequence | SEQ ID NO: | Possible Member of Primer Set No. |
|---|---|---|---|
| Primer M3M4N1 | ggcagcatgctcaagtagc | 128 | 43 or 113 |
| Primer M3M4N2 | gggttcgaatcccgtagg | 129 | 43 or 113 |
| Probe M3M4N1M3M4N2 | taccgactgagctacctggc | 130 | 43 or 113 |
| Primer M3M4N3 | gcagcatgctcaagtagcc | 131 | 44 or 114 |
| Primer M3M4N4 | gggttcgaatcccgtagg | 132 | 44 or 114 |
| Probe M3M4N3M3M4N4 | taccgactgagctacctggc | 133 | 44 or 114 |
| Primer M3M4N5 | gcagcatgctcaagtagcc | 134 | 45 or 115 |
| Primer M3M4N6 | ccctttcaaggcggtagc | 135 | 45 or 115 |
| Probe M3M4N5M3M4N6 | taccgactgagctacctggc | 136 | 45 or 115 |
| Primer M3M4N7 | gcagcatgctcaagtagcc | 137 | 46 or 116 |
| Primer M3M4N8 | gccctttcaaggcggtag | 138 | 46 or 116 |
| Probe M3M4N7M3M4N8 | taccgactgagctacctggc | 139 | 46 or 116 |
| Primer M3M4N9 | ggcagcatgctcaagtagc | 140 | 47 or 117 |
| Primer M3M4N10 | ccctttcaaggcggtagc | 141 | 47 or 117 |
| Probe M3M4N9M3M4N10 | taccgactgagctacctggc | 142 | 47 or 117 |

| Nested Primers for amplicon produced by M5 and M6 | Sequence | SEQ ID NO: | Possible Member of Primer Set No. |
|---|---|---|---|
| Primer M5M6N1 | ggcagcatgctcaagtagc | 143 | 48 or 118 |
| Primer M5M6N2 | ctgtggcgcagttggttag | 144 | 48 or 118 |
| Probe M5M6N1M5M6N2 | taccgactgagctacctggc | 145 | 48 or 118 |
| Primer M5M6N3 | gcagcatgctcaagtagcc | 146 | 49 or 119 |
| Primer M5M6N4 | ctgtggcgcagttggttag | 147 | 49 or 119 |
| Probe M5M6N3M5M6N4 | tacgactgagctacctggc | 148 | 49 or 119 |

-continued

| Nested Primers for amplicon produced by M5 and M6 | Sequence | SEQ ID NO: | Possible Member of Primer Set No. |
|---|---|---|---|
| Primer M5M6N5 | cggcagcatgctcaagtag | 149 | 50 or 120 |
| Primer M5M6N6 | ctgtggcgcagttggttag | 150 | 50 or 120 |
| Probe M5M6N5M5M6N6 | taccgactgagctacctggc | 151 | 50 or 120 |
| Primer M5M6N7 | cggcagcatgctcaagta | 152 | 51 or 121 |
| Primer M5M6N8 | ctgtggcgcagttggttag | 153 | 51 or 121 |
| Probe M5M6N7M5M6N8 | taccgactgagctacctggc | 154 | 51 or 121 |
| Primer M5M6N9 | ggcagcatgctcaagtagc | 155 | 52 or 122 |
| Primer M5M6N10 | gtggcgcagttggttagc | 156 | 52 or 122 |
| Probe M5M6N9M5M6N10 | taccgactgagctacctggc | 157 | 52 or 122 |

| Nested Primers for amplicon produced by M7 and M8 | Sequence | SEQ ID NO: | Possible Member of Primer Set No. |
|---|---|---|---|
| Primer M7M8N1 | ggcagcatgctcaagtagc | 158 | 53 or 123 |
| Primer M7M8N2 | gggttcgaatcccgtagg | 159 | 53 or 123 |
| Probe M7M8N1M7M8N2 | taccgactgagctacctggc | 160 | 53 or 123 |
| Primer M7M8N3 | gcagcatgctcaagtagcc | 161 | 54 or 124 |
| Primer M7M8N4 | gggttcgaatcccgtagg | 162 | 54 or 124 |
| Probe M7M8N3M7M8N4 | taccgactgagctacctggc | 163 | 54 or 124 |
| Primer M7M8N5 | gcagcatgctcaagtagcc | 164 | 55 or 125 |
| Primer M7M8N6 | ccctttcaaggcggtagc | 165 | 55 or 125 |
| Probe M7M8N5M7M8N6 | taccgactgagctacctggc | 166 | 55 or 125 |
| Primer M7M8N7 | gcagcatgctcaagtagcc | 167 | 56 or 126 |
| Primer M7M8N8 | gccctttcaaggcggtag | 168 | 56 or 126 |
| Probe M7M8N7M7M8N8 | taccgactgagctacctggc | 169 | 56 or 126 |
| Primer M7M8N9 | ggcagcatgctcaagtagc | 170 | 57 or 127 |
| Primer M7M8N10 | ccctttcaaggcggtagc | 171 | 57 or 127 |
| Probe M7M8N9M7M8N10 | taccgactgagctacctggc | 172 | 57 or 127 |

| Nested Primers for amplicon produced by M9 and M10 | Sequence | SEQ ID NO: | Possible Member of Primer Set No. |
|---|---|---|---|
| Primer M9M10N1 | gcagcatgctcaagtagcc | 173 | 58 or 128 |
| Primer M9M10N2 | aatcccgtaggggtacg | 174 | 58 or 128 |
| Probe M9M10N1M9M10N2 | taccgactgagctacctggc | 175 | 58 or 128 |
| Primer M9M10N3 | ggcagcatgctcaagtagc | 176 | 59 or 129 |
| Primer M9M10N4 | aatcccgtaggggtacg | 177 | 59 or 129 |

-continued

| Nested Primers for amplicon produced by M9 and M10 | Sequence | SEQ ID NO: | Possible Member of Primer Set No. |
|---|---|---|---|
| Probe M9M10N3M9M10N4 | taccgactgagctacctggc | 178 | 59 or 129 |
| Primer M9M10N5 | gcagcatgctcaagtagcc | 179 | 60 or 130 |
| Primer M9M10N6 | gaatcccgtaggggtacg | 180 | 60 or 130 |
| Probe M9M10N5M9M10N6 | taccgactgagctacctggc | 181 | 60 or 130 |
| Primer M9M10N7 | ggcagcatgctcaagtagc | 182 | 61 or 131 |
| Primer M9M10N8 | gaatcccgtaggggtacg | 183 | 61 or 131 |
| Probe M9M10N7M9M10N8 | taccgactgagctacctggc | 184 | 61 or 131 |
| Primer M9M10N9 | gcagcatgctcaagtagcc | 185 | 62 or 132 |
| Primer M9M10N10 | gggttcgaatcccgtagg | 186 | 62 or 132 |
| Probe M9M10N9M9M10N10 | taccgactgagctacctggc | 187 | 62 or 132 |

| P900 Series Primers | Sequence | SEQ ID NO: | Possible Member of Primer Set No. |
|---|---|---|---|
| Primer P901 | ggcacggctcttgttgtagt | 188 | 63 or 133 |
| Primer P902 | gcgctgctggagttgatt | 189 | 63 or 133 |
| Probe P901P902 | gaatataaagcagccgctgc | 190 | 63 or 133 |
| Primer P901A | cacggctcttgttgtagtcg | 191 | 64 or 134 |
| Primer P902A | gcgctgctggagttgatt | 192 | 64 or 134 |
| Probe P901AP902A | gaatataaagcagccgctgc | 193 | 64 or 134 |
| Primer P901B | cggctcttgttgtagtcgaa | 194 | 65 or 135 |
| Primer P902B | gcgctgctggagttgatt | 195 | 65 or 135 |
| Probe P901BP902B | gaatataaagcagccgctgc | 196 | 65 or 135 |
| Primer P901C | cggctcttgttgtagtcgaag | 197 | 66 or 136 |
| Primer P902C | gcgctgctggagttgatt | 198 | 66 or 136 |
| Probe P901CP902C | gaatataaagcagccgctgc | 199 | 66 or 136 |
| Primer P901D | acggctcttgttgtagtcgaa | 200 | 67 or 137 |
| Primer P902D | gcgctgctggagttgatt | 201 | 67 or 137 |
| Probe P901DP902D | gaatataaagcagccgctgc | 202 | 67 or 137 |

| Nested Primers for amplicon produced by P901 and 902 Series Primers | Sequence | SEQ ID NO: | Possible Member of Primer Set No. |
|---|---|---|---|
| Primer P901N | gttccagcgccgaaagtat | 203 | 63, 64, 65, 66, 67 or 68 |
| Primer P902N | caagaccgacgccaaagac | 204 | 63, 64, 65, 66, 67 or 68 |

-continued

| Nested Primers for amplicon produced by P901 and 902 Series Primers | Sequence | SEQ ID NO: | Possible Member of Primer Set No. |
|---|---|---|---|
| Primer P901AN | gttccagcgccgaaagtat | 205 | 63, 64, 65, 66, 67 or 69 |
| Primer P902AN | caagaccgacgccaaaga | 206 | 63, 64, 65, 66, 67 or 69 |
| Primer P901BN | gttccagcgccgaaagtatt | 207 | 63, 64, 65, 66, 67 or 70 |
| Primer P902BN | caagaccgacgccaaagac | 208 | 63, 64, 65, 66, 67 or 70 |
| Primer P901CN | agcgccgaaagtattccag | 209 | 63, 64, 65, 66, 67 or 71 |
| Primer P902CN | caagaccgacgccaaagac | 210 | 63, 64, 65, 66, 67 or 71 |
| Primer P901DN | gttccagcgccgaaagtatt | 211 | 63, 64, 65, 66, 67 or 72 |
| Primer P902DN | caagaccgacgccaaaga | 212 | 63, 64, 65, 66, 67 or 72 |

With respect to various nested PCR techniques for which the primers of the subject invention are useful, various combinations of "appropriate" primer sets are set forth in the following table. Primer sets identified as "Appropriate Second PCR Primer Sets" can be used to amplify the amplicon generated by the "First PCT Primer Set".

| First PCR Primer Set | Appropriate Second PCR Primer Sets |
|---|---|
| 1 | 2 |
| 3 | 13, 14, 15, 16 or 17 |
| 4 | 18, 19, 20, 21 or 22 |
| 5 | 23, 24, 25, 26 or 27 |
| 6 | 28, 29, 30, 31 or 32 |
| 7 | 33, 34, 35, 36 or 37 |
| 8 | 38, 39, 40, 41 or 42 |
| 9 | 43, 44, 45 46 or 47 |
| 10 | 48, 49, 50, 51 or 52 |
| 11 | 53, 54, 55, 56 or 57 |
| 12 | 58, 59, 60, 61 or 61 |
| 63 or 64 or 65 or 66 or 67 | 68 or 69 or 70 or 71 or 72 |

Further non-limiting embodiments provided by the subject invention include:

Embodiment 36 A method for herd management that stratifies the risk of bulk tank milk lots derived from diagnostic-tested subgroups potentially containing DNA from pathogenic *mycobacterium* comprising *Mycobacterium avium* subspecies *paratuberculosis* (Map), said method comprising:

(a) determining the level of a *Mycobacterium avium* subsp. *paratuberculosis*-specific antibodies in blood samples from individual milk-producing animals, wherein said determining comprises:
(i) conducting a first test that identifies if animals have had antigenic exposure to Map; and
(ii) conducting a second test that assesses the probability of active Map replication in the animals;
(b) categorizing the animals into a plurality of risk categories based, at least in part, on the results of the first and second tests; and
(c) detecting the presence of Map in a bulk milk sample obtained from a volume of milk from a plurality of animals in each category by determining the presence of the Map IS1311 insertion sequence (Genbank accession # U16276) in the bulk milk sample.

Embodiment 37. The method of embodiment 36, wherein the first test and/or the second test is an immunoassay, such as an enzyme-linked immunosorbent assay (ELISA).

Embodiment 38 The method of embodiment 36, wherein the first test is FUIDI #1 and/or the second test is FUIDI #2.

Embodiment 39 The method of embodiment 36, wherein said categorizing of (b) further comprises separating the animals of each category from animals of any other category.

Embodiment 40 The method of any one of embodiments 36 to 39, wherein the plurality of categories comprises:
(i) a first category of animals having no detectable Map-specific antibodies in the first and second tests;
(ii) a second category of animals having a low level of Map-specific antibodies in the first test and no detectable Map-specific antibodies in the second test;
(iii) a third category of animals having an intermediate level of Map-specific antibodies in the first test and no detectable Map-specific antibodies in the second test;
(iv) a fourth category of animals having a high level of Map-specific antibodies in the first test and no detectable Map-specific antibodies in the second test; and
(v) a fifth category of animals having a low, intermediate, or high level of Map-specific antibodies in the first test, and low or intermediate level of Map-specific antibodies in the second test.

Embodiment 41 The method of embodiment 40, further comprising, after determining the presence of the Map IS1311 insertion sequence in a bulk milk sample from the first, second, or third risk category of animals in accordance with (c), wherein the Map IS1311 insertion sequence is determined to be absent in the bulk milk sample of (c), repeating (a) and (c) annually to reassess the risk category.

Embodiment 42 The method of embodiment 40, further comprising, after determining the presence of the Map IS1311 insertion sequence in a bulk milk sample from the first, second, third, or fourth risk category of animals in accordance with (c), wherein the Map IS1311 insertion sequence is determined to be present in the bulk milk sample (c), repeating (c) one or more times to exclude incidental contamination.

Embodiment 43 The method of embodiment 42, further comprising, after repeating (c) one or more times to exclude incidental contamination, wherein the Map IS1311 insertion sequence is determined to be present in repeated (c) such that incidental contamination is excluded, determining the presence of the Map IS1311 insertion sequence in a milk sample of each individual animal in the risk category.

Embodiment 44 The method of embodiment 43, wherein the Map IS1311 insertion sequence is determined to be present in the milk sample of at least one individual animal, the method further comprising removing the at least one individual animal from milk production.

Embodiment 45 The method of embodiment 43, wherein the Map IS1311 insertion sequence is determined to be absent in the milk sample of at least one individual animal, the method further comprising repeating (a) and (c) annually to reassess the risk category.

Embodiment 46 The method of embodiment 40, further comprising, after determining the presence of the Map IS1311 insertion sequence in a bulk milk sample from the third risk category of animals in accordance with (c), wherein the Map IS1311 insertion sequence is determined to be absent in the bulk milk sample, repeating (a) and determine presence of the Map IS1311 in milk of each individual animal prior to calving and two months after calving.

Embodiment 47 The method of embodiment 40, further comprising, after determining the presence of the Map IS1311 insertion sequence in a bulk milk sample from the first or second risk category of animals in accordance with (c), wherein the Map IS1311 insertion sequence is determined to be present in the bulk milk sample of (c), repeating (c) one or more times to exclude incidental contamination, wherein the Map IS1311 insertion sequence is determined to be present in repeated (c) such that incidental contamination is excluded, determining the presence of the Map IS1311 insertion sequence in a milk sample of each individual animal in the risk category, and if absent, repeating (a) and (c) annually to reassess risk category.

Embodiment 48 The method of embodiment 40, further comprising, after determining the presence of the Map IS1311 insertion sequence in a bulk milk sample from the third or fourth risk category of animals in accordance with (c), wherein the Map IS1311 insertion sequence is determined to be present in the bulk milk sample of (c), repeating (c) one or more times to exclude incidental contamination, wherein the Map IS1311 insertion sequence is determined to be present in repeated (c) such that incidental contamination is excluded, determining the presence of the Map IS1311 insertion sequence in a milk sample of each individual animal in the risk category, and if absent, repeating (a) and determining the presence of Map IS1311 of each individual animal prior to calving and two months after calving.

Embodiment 49 The method of embodiment 40, further comprising, after determining the presence of the Map IS1311 insertion sequence in a bulk milk sample from the fourth risk category of animals in accordance with (c), wherein the Map IS1311 insertion sequence is determined to be absent in the bulk milk sample of (c), repeating (a) and determining the presence of Map IS1311 in milk of each individual animal prior to calving and two months after calving.

Embodiment 50 The method of embodiment 40, further comprising, after determining the presence of the Map IS1311 insertion sequence in the bulk milk sample from the fifth risk category of animals in accordance with (c), wherein the Map IS1311 insertion sequence is determined to be absent in the bulk milk sample of (c), determining the presence of Map IS1311 in a bulk sample of the fifth risk category of animals every two months.

Embodiment 51 The method of embodiment 50, further comprising, if the level of Map-specific antibody in the second test increases for an animal or animals, increasing the frequency of Map IS1311 determination in the milk sample of the individual animal or animals to monthly.

Embodiment 52 The method of embodiment 51, further comprising removing those animal or animals from milk production if Map IS1311 is determined to be present in milk of the individual animal or animals.

Embodiment 53 The method of embodiment 40, further comprising, after determining the presence of the Map IS1311 insertion sequence in a bulk milk sample from the fifth risk category of animals in accordance with (c), wherein the Map IS1311 insertion sequence is determined to be present in the bulk milk sample of (c), repeating (a) and determining the presence of Map IS1311 in milk of each animal of the fifth risk category immediately.

Embodiment 54 The method of embodiment 53, further comprising removing the animal of animals from milk production if Map IS1311 is determined to be present in milk of the individual animal or animals.

Embodiment 55 The method of any one of embodiments 36-54, wherein the animals are selected from among cows, sheep, goats, llamas, buffalo, camels, and yaks.

Embodiment 56 The method of any one of embodiments 36-54, wherein the determining of the presence of Map IS1311 insertion sequence in (c) comprises amplifying Map IS1311-specific nucleic acid in the bulk milk sample using polymerase chain reaction (PCR); and detecting the IS1311 insertion sequence shared by *Mycobacterium avium* subspecies *avium, Mycobacterium avium* subspecies *paratuberculosis, Mycobacterium hominissuis*, and *Mycobacterium avium* complex (MAC).

Embodiment 57 The method of embodiment 56, wherein the amplifying comprises contacting the bulk milk sample with a primer set that amplifies a nucleic acid sequence within the Map 1311 insertion sequence.

Embodiment 58 The method of embodiment 56, wherein the amplifying comprises contacting the bulk milk sample with a primer set comprising a first primer pair and a second primer pair, wherein the first primer pair is designed to amplify the 242 base pair IS1311 sequence, and wherein the second primer pair is designed to span a region within the IS1311 sequence.

Embodiment 59 The method of embodiment 56, wherein said determining comprises the steps of:
  (a) treating the bulk milk sample to solubilize the nucleic acids therein;
  (b) forming a polymerase chain reaction (PCR) solution comprising:
    (i) at least a portion of the solubilized nucleic acids from step (a);
    (ii) a PCR primer set that amplifies a nucleic acid sequence within the Map IS1311 insertion sequence;
    (iii) a mixture of nucleoside triphosphate monomers; and
    (iv) a PCR polymerase in a buffered solution;

(c) carrying out a PCR on the PCR solution to amplify any Map IS1311-specific nucleic acid which is specific for the particular primer set used to a level sufficient for detection; and (d) detecting the presence of amplified MAP IS1311-specific nucleic acid in the resulting solution which is specific for the particular primer set used; wherein the detection of the amplified Map IS1311-specific nucleic acid which is specific for the particular primer set used indicates that Map is present in the bulk milk sample.

Embodiment 59 The method of embodiment 58, wherein the primer set comprises direct and nested primer sets comprising: IS1 (SEQ ID NO: 1), IS2 (SEQ ID NO: 2), IS3 (SEQ ID NO: 3), and IS4 (SEQ ID NO: 4), or a fragment comprising at least 8 contiguous nucleotides thereof Embodiment 60 The method of embodiment 56, wherein the detection of the presence of amplified Map IS1311-specific nucleic acid comprises gel electrophoresis of the amplified Map IS1311-specific nucleic acid solution and staining of the resulting gel to visualize the band of the MAP IS1311-specific nucleic acid specific for the particular primer set used.

Embodiment 61 The method of embodiment 58, wherein at least one of the oligonucleotides in the primer set or at least one of the nucleoside triphosphate monomers contains a label which will be incorporated into the amplified Map IS1311-specific nucleic acid and can be used for the detection of the amplified Map IS1311-specific nucleic acid.

Embodiment 62 The method of any one of embodiments 36-61, wherein said determining of (c) uses a nested polymerase chain reaction (PCR) procedure comprising the steps of:

(a) treating the bulk milk sample to solubilize the nucleic acids therein;

(b) forming a first PCR solution containing at least a portion of the solubilized nucleic acids from step (a), a first PCR primer set, a first mixture of nucleoside triphosphate monomers, and a first PCR polymerase in a first buffered solution, wherein the first primer set comprises a first pair of oligonucleotides as set forth in primer set 1, 3, 4, 5, 6, 7, 8, 9, 10, 11, 12, 63, 64, 65, 66 or 67 or fragments of the first pair of oligonucleotides that are at least 8 consecutive nucleotides in length;

(c) performing a first polymerase chain reaction on the first PCR solution to amplify any IS1311-specific nucleic acid which is specific for the first primer set used;

(d) forming a second PCR solution containing at least a portion of the PCR-reacted first PCR solution from step (c), a second PCR primer set, a second mixture of nucleoside triphosphate monomers, and a second PCR polymerase in a second buffered solution, wherein the second primer set comprises a second pair of oligonucleotides as set forth in primer set 2, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 68, 69, 70, 71 or 72 or fragments of the second pair of oligonucleotides that are at least 8 consecutive nucleotides in length;

(e) performing a second polymerase chain reaction on the second PCR reaction solution to amplify any Map IS1311-specific nucleic acid which is specific for the second primer set used to a level sufficient for detection; and (f) detecting the presence of amplified Map IS1311-specific nucleic acid in the resulting solution from step (e) which is specific for the second primer set; wherein the detection of the amplified Map IS1311-specific nucleic acid which is specific for the second primer set indicates that Map is present in the bulk milk sample.

Embodiment 63 The method of embodiment 62, wherein the detection in step (f) comprises gel electrophoresis of the amplified Map IS1311-specific nucleic acid solution and staining of the resulting gel to visualize the Map IS1311-specific nucleic acid on the gel.

Embodiment 64 The method of embodiment 63, wherein either the primers, or one or more of the monomers, or both, employed in steps (b) and (d) contains a label whereby the amplified Map IS1311-specific nucleic acid that results in step (e) contains the label, and the detection in step (f) comprises detecting the presence of the label.

Embodiment 65 A method of detecting the presence of pathogenic *mycobacterium* comprising *Mycobacterium avium* subsp. *paratuberculosis* (Map) and other pathogenic *mycobacterium* in a bulk milk sample obtained from a volume of milk from a plurality of milk-producing animals, comprising determining the presence of the Map IS1311 insertion sequence (Genbank accession # U16276) in the bulk milk sample.

Embodiment 66 The method of embodiment 65, wherein the determining of the presence of Map IS1311 insertion sequence comprises amplifying Map IS1311-specific nucleic acid in the bulk milk sample using polymerase chain reaction (PCR); and detecting the IS1311 insertion sequence shared by *Mycobacterium avium* subspecies *avium, Mycobacterium avium* subspecies *paratuberculosis, Mycobacterium hominissuis,* and *Mycobacterium avium* complex (MAC).

Embodiment 67 The method of embodiment 66, wherein the amplifying comprises contacting the bulk milk sample with a primer set that amplifies a nucleic acid sequence within the Map 1311 insertion sequence.

Embodiment 68 The method of embodiment 66, wherein the amplifying comprises contacting the bulk milk sample with a primer set comprising a first primer pair and a second primer pair, wherein the first primer pair is designed to amplify the 242 base pair IS1311 sequence, and wherein the second primer pair is designed to span a region within the IS1311 sequence.

Embodiment 69 The method of embodiment 65, wherein said determining comprises the steps of:

(a) treating the bulk milk sample to solubilize the nucleic acids therein;

(b) forming a polymerase chain reaction (PCR) solution comprising:
  (i) at least a portion of the solubilized nucleic acids from step (a);
  (ii) a PCR primer set that amplifies a nucleic acid sequence within the Map IS1311 insertion sequence;
  (iii) a mixture of nucleoside triphosphate monomers; and
  (iv) a PCR polymerase in a buffered solution;

(c) carrying out a PCR on the PCR solution to amplify any Map IS1311-specific nucleic acid which is specific for the particular primer set used to a level sufficient for detection; and (d) detecting the presence of amplified MAP IS1311-specific nucleic acid in the resulting solution which is specific for the particular primer set used; wherein the detection of the amplified Map IS1311-specific nucleic acid which is specific for the particular primer set used indicates that Map is present in the bulk milk sample.

Embodiment 70 The method of any one of embodiments 65-69, wherein the animals are selected from among cows, sheep, goats, llamas, buffalo, camels, and yaks.

Embodiment 71 The method of embodiment 70, wherein the primer set comprises direct and nested primer sets comprising: IS1 (SEQ ID NO: 1), IS2 (SEQ ID NO: 2), IS3 (SEQ ID NO: 3), and IS4 (SEQ ID NO: 4), or a fragment comprising at least 8 contiguous nucleotides thereof.

Embodiment 72 The method of embodiment 68, wherein the detection of the presence of amplified Map IS1311-specific nucleic acid comprises gel electrophoresis of the amplified Map IS1311-specific nucleic acid solution and staining of the resulting gel to visualize the band of the MAP IS1311-specific nucleic acid specific for the particular primer set used.

Embodiment 73 The method of embodiment 69, wherein at least one of the oligonucleotides in the primer set or at least one of the nucleoside triphosphate monomers contains a label which will be incorporated into the amplified Map IS1311-specific nucleic acid and can be used for the detection of the amplified Map IS1311-specific nucleic acid.

Embodiment 74 The method of embodiment 66, wherein said determining uses a nested polymerase chain reaction (PCR) procedure comprising the steps of:
  (a) treating the bulk milk sample to solubilize the nucleic acids therein;
  (b) forming a first PCR solution containing at least a portion of the solubilized nucleic acids from step (a), a first PCR primer set, a first mixture of nucleoside triphosphate monomers, and a first PCR polymerase in a first buffered solution, wherein the first primer set comprises a first pair of oligonucleotides as set forth in primer set 1, 3, 4, 5, 6, 7, 8, 9, 10, 11, 12, 63, 64, 65, 66 or 67 or fragments of the first pair of oligonucleotides that are at least 8 consecutive nucleotides in length;
  (c) performing a first polymerase chain reaction on the first PCR solution to amplify any IS1311-specific nucleic acid which is specific for the first primer set used;
  (d) forming a second PCR solution containing at least a portion of the PCR-reacted first PCR solution from step (c), a second PCR primer set, a second mixture of nucleoside triphosphate monomers, and a second PCR polymerase in a second buffered solution, wherein the second primer set comprises a second pair of oligonucleotides as set forth in primer set 2, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 68, 69, 70, 71 or 72 or fragments of the second pair of oligonucleotides that are at least 8 consecutive nucleotides in length;
  (e) performing a second polymerase chain reaction on the second PCR reaction solution to amplify any Map IS1311-specific nucleic acid which is specific for the second primer set used to a level sufficient for detection; and
  (f) detecting the presence of amplified Map IS1311-specific nucleic acid in the resulting solution from step (e) which is specific for the second primer set; wherein the detection of the amplified Map IS1311-specific nucleic acid which is specific for the second primer set indicates that Map is present in the bulk milk sample.

Embodiment 75 The method of embodiment 66, wherein the detection in step (f) comprises gel electrophoresis of the amplified Map IS1311-specific nucleic acid solution and staining of the resulting gel to visualize the Map IS1311-specific nucleic acid on the gel.

Embodiment 76 The method of embodiment 74, wherein either the primers, or one or more of the monomers, or both, employed in steps (b) and (d) contains a label whereby the amplified Map IS1311-specific nucleic acid that results in step (e) contains the label, and the detection in step (f) comprises detecting the presence of the label.

Embodiment 77 A method to strengthen the ability of milk-producing animals to resist environmental challenges by pathogenic *mycobacterium* comprising *Mycobacterium avium* subspecies *paratuberculosis* (Map), said method comprising:
  (a) identifying milk-producing animals that have a low antibody level to Map (anti-Map antibody level);
  (b) serially monitoring the level of anti-Map antibodies in the identified animals;
  (c) retaining female animals that maintain a low anti-Map antibody level; and
  (d) incorporating female animals into a herd as replacement animals to replace female animals taken out of milk production, wherein the incorporated female animals are progeny of animals that maintain a low-anti-Map antibody level.

Embodiment 78 The method of embodiment 77, wherein individual animals identified by their prior exposure, magnitude of immune stimulation, and status of the infection, allow identification of animals that have effectively contained environmental challenges by pathogenic *mycobacterium*, specifically *Mycobacterium avium* subspecies *paratuberculosis*.

Embodiment 79 The method of embodiment 77, wherein female progeny from animals whose mother do exhibit the continued ability to effectively handle environmental challenges by pathogenic *mycobacterium* comprising *Mycobacterium avium* subspecies *paratuberculosis* constitute prime replacement animals.

Embodiment 80 The method of embodiment 77, wherein herd replacements are drawn from animals with documented ability to tolerate environmental challenges by pathogenic *mycobacterium* in order to enhance overall herd immunity to Map and other intra-cellular pathogens.

Embodiment 81 The method of any one of embodiments 77-80, wherein the animals are selected from among cows, sheep, goats, llamas, buffalo, camels, and yaks.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLES

Example 1

Materials and Methods

Sample Handling and Nested PCR Protocol.

Samples may have the consistency of wet grass to a sticky paste that can be molded, to a semi-liquid, making it a challenge to weigh efficiently. Samples that are liquid to a semi-liquid can be measured using disposable transfer pipette. For really viscous samples, cut the tip from the pipette to increase the diameter of the bore and this will aid in sampling. When using a pipette to measure, it is preferable to use between 250 and 300 ul of sample, to avoid over-load of the bead sample tube.

Performing PCR (Amplifying the IS1311 Sequence)

| Master Mix: | 20 ul | Master Mix (supplied with kit) |
|---|---|---|
| | 19 ul | PCR Quality Water (supplied with kit) |
| | 0.5 ul | Primer #1 (supplied with kit) |
| | 0.5 ul | Primer #2 (supplied with kit) |
| | 40.0 ul | |
| | 10.0 ul | Processed fecal sample |
| | 50.0 ul | |

The following primers were used for Standard PCR:

```
IS1 5'-CGA TTT ATC AGG CAC TCA TCG-3' (SEQ ID NO: 1)

IS2 5'-CAA ATA GGC CTC CAT CAC CA-3' (SEQ ID NO: 2)
IS2 & IS2 produce a product of 242 base pairs
```

Amplifications:
Standard PCR
2 min @ 94C
30 cycles of: 30 sec @ 94C
15 sec @ 58C
60 sec @ 72C
Hold @ 4C
The following primers were used for Nested PCR:

```
IS3  5'-ATG AAC GGA GCG CAT CAC-3' (SEQ ID NO: 3)

IS4  5'-CGA CCG AAG CTT GGG AAT-3' (SEQ ID NO: 4)
IS3 & IS4 produce a product of 104 base pairs
```

Amplifications:
Nested PCR
Master Mix is the same as Standard PCR with the exception that the volume of water is increased from 19 ul to 28 ul and a 1.0 ul sample of the Standard PCR reaction is used instead of 10 ul as in the fecal processing sample.
2 min @ 94C
30 cycles of: 30 sec @ 94C
15 sec @ 63C
60 sec @ 72C
Hold @ 4C
Samples from USDA Johne's Fecal Check Test (KIT #105 from USDA)
Using PowerSoil DNA Kit (MO BIO) previous to PCR

| USDA # | USDA key | Colonies/tube | P90-P91 | J1-J2 | IS1-IS2 | IS3-IS4 |
|---|---|---|---|---|---|---|
| 1 | + | 15 | − | + | − | + |
| 2 | + | TNTC | + | + | + | + |
| 3 | − | 0 | − | − | − | − |
| 4 | + | ? | + | + | + | + |
| 5 | − | 0 | − | − | − | − |
| 6 | + | 9 | − | + | − | + |
| 7 | − | 0 | − | − | − | − |
| 8 | + | TNTC | − | + | − | + |
| 9 | + | 5 | − | + | − | + |
| 10 | + | TNTC | − | + | − | + |
| 11 | + | 4 | − | + | − | + |
| 12 | + | 14 | + | + | + | + |
| 13 | − | 0 | − | − | − | − |
| 14 | + | TNTC | + | + | − | + |
| 15 | + | 1 | + | + | + | + |
| 16 | + | 15 | + | + | + | + |
| 17 | − | 0 | − | − | − | − |
| 18 | + | 1 | + | + | + | + |
| 19 | + | 1 | + | + | + | + |
| 20 | − | 0 | − | − | − | − |
| 21 | + | 1 | + | + | + | + |
| 22 | + | 6 | − | + | − | + |
| 23 | + | 9 | + | + | + | + |
| 24 | − | 0 | − | − | − | − |
| 25 | + | 1 | + | + | + | + |
| 26 | + | TNTC | + | + | + | + |

P90-P91 flanking primers for IS900;
J1-J2 nested PCR primers for P90-P91 amplicon IS1-IS2 flanking primers for IS1311;
IS3-IS4 nested PCR primers for IS1-IS2 amplicon Twenty six (26) fecal samples were provided by APHIS/USDA with known MAP infection status. However, the status (+/−) of these blinded samples was unknown until after results of the PCR assays were communicated to USDA. As indicated in the Table, the IS3 and IS4 primers identified each of the samples known to be derived from MAP infected animals. Based on these results, the laboratory met the qualification requirements of the USDA as a diagnostic center for MAP.

Samples from USDA Johne's Fecal Check Test (Kit #F1)
Using DNA purification Kit (patent pending) previous to PCR

| USDA # | USDA Key | P90-P91 | J1-J2 | P901-P902 | P903-P904 | IS1-IS2 | IS3-IS4 |
|---|---|---|---|---|---|---|---|
| 1 | − | − | − | − | − | − | − |
| 2 | + | − | + | − | + | − | + |
| 3 | + | − | + | − | + | − | + |
| 4 | + | − | − | − | − | − | − |
| 5 | + | − | + | − | + | − | + |
| 6 | + | − | + | − | + | − | + |
| 7 | + | − | − | − | + | − | + |
| 8 | − | − | − | − | − | − | − |
| 9 | + | − | + | − | + | − | + |
| 10 | + | − | + | − | + | − | + |
| 11 | − | − | − | − | − | − | − |
| 12 | + | − | + | − | + | − | + |
| 13 | − | − | − | − | − | − | − |
| 14 | + | − | + | − | + | − | + |
| 15 | + | − | + | − | + | − | + |
| 16 | + | − | + | − | + | − | + |
| 17 | + | − | + | − | + | − | + |
| 18 | − | − | − | − | − | − | − |
| 19 | + | − | + | + | + | − | + |
| 20 | + | − | + | + | + | − | + |
| 21 | − | − | − | − | − | − | − |

| USDA # | USDA Key | P90-P91 | J1-J2 | P901-P902 | P903-P904 | IS1-IS2 | IS3-IS4 |
|---|---|---|---|---|---|---|---|
| 22 | + | − | + | − | + | − | + |
| 23 | + | − | − | − | − | − | − |
| 24 | − | − | − | − | − | − | − |
| 25 | + | − | + | − | + | − | + |

Fecal samples were provided by USDA with known MAP infection status. However, the status (+/−) of these samples was unknown until after results of the PCR assays had been communicated to USDA. As indicated in the Table, the IS3 and IS4 primers, the P902 and P903 primers and the J1 and J2 primers identified each of the samples known to be derived from MAP infected animals.

Statistical comparison of P90-P91/J1-J2 versus IS1-IS2/IS3-IS4 primers on three USDA laboratory certification kit fecal specimens

|  | P90-P91/J1-J2 | IS1-IS2/IS3-IS4 |
|---|---|---|
| Sensitivity | 89.3% | 96.5% |
| Specificity | 90.5% | 95.2% |
| Kappa Coefficient | 0.753 | 0.903 |
| Interpretation | Good agreement | Very good agreement |

Comparison of primers P90-P91, IS1-IS2, P90-P91/J1-J2 and IS1-IS2/IS3-IS4 false positive and false negative observed on three USDA certification kit fecal specimens Primers

|  | P90-P91 | IS1-IS2 | P90-P91/J1-J2 | IS1-IS2/IS3-IS4 |
|---|---|---|---|---|
| False Positive | 20 | 26 | 2 | 1* |
| False Negative | 81 | 75 | 6 | 2 |

*Specimen heavily spiked with M. avium

Example 2

ELISA Testing

The example is directed to comparative ability of a commercially available, USDA certified, Map ELISA test and a University of Florida College of Veterinary Medicine (UFCVM) Map ELISA test to diagnose Johne's disease in sera of cows with prior necropsy status confirmation.

Within the state of Florida, herds are screened using the Map Paracheck ELISA assay (Biocor, Omaha, Nebr.). A preliminary effort to assess comparative test sensitivity between the ELISA tests systems employed at the Florida' State Diagnostic Laboratory at Live Oak and the UFCVM identified initial concerns, relative to the sensitivity of the respective tests. Forty sera had been independently tested using the Paracheck test at the state's Map diagnostic facility and then forwarded to UFCVM. The Paracheck ELISA data identified 6 of the 40 specimens tested as having significant ELISA titer: 1 inconclusive, 1 positive, and 5 strong positives. The UFCVM ELISA test results done on the same sera revealed 4 sera as being suspicious, 2 as positive, and 8 as strong-positive.

To assess the validity of the data reported from the respective institutions, necropsy files at the University of Florida College of Veterinary Medicine were reviewed in order to identify cows with well documented Johne's disease on gross and microscopic examination. The material available on each cow was then reviewed in order to identify the availability of feces and serum.

Study Population: The pathology reports from 2002-2005 were reviewed to identify dairy cows with necropsy confirmed Johne's disease for whom sera and fecal samples still existed. Nine animals meet the study entry criteria. In each case, an ELISA titer from the day of necropsy existed. The residual sera were divided into two aliquots, coded, and sent to the respective testing facilities. The previous UFCVM ELISA titers were used as a quality control check.

State of Florida Diagnostic Laboratory at Live Oak: The ParaCheck ELISA assays (Biocor, Omaha, Nebr.) were done in accordance with manufacturers' instruction and interpreted as prescribed by the kit insert. ELISA score of 0.00 to 0.49 is deemed negative; a score of 0.50 to 0.99 is deemed suspicious/inconclusive; and a score of 1.00 to 3.49 is deemed positive. A strong positive is any ELISA score of 3.50 or greater.

University of Florida College of Veterinary Medicine's Preabsorbed ELISA Test: The in-house ELISA test was performed using a crude soluble protoplasmic antigen of *M. avium* (Allied Monitor, Missouri). Test sera were preabsorbed with *Mycobacterium pheli*. ELISA results were calculated from absorbance at OD 405 nm. All readings less than 1.6 optical density (OD) are deemed negative; readings between 1.6 and 1.99 were deemed suspicious/inconclusive. Readings of 2.0 to 2.5 were called positive. A strong positive was deemed any reading of above 2.5. All ELISA tests done at UFCVM were run in triplicate.

Results:

The comparative ELISA tests results are listed in table provided below. The Paracheck ELISA test identified one of the 9 Johne's disease cows. Another cow was deemed inconclusive. The in-house ELISA test correctly identified 6 of the nine animals. All three sera negative (range 0.49, 0.82, and 1.43) in UFCVM test were negative in the Paracheck test. Three cows (33%) with well documented Johne's disease were not identified by either ELISA test.

| Cow # | Paracheck Score | Paracheck Interpretation | UF Map ELISA Score | UF Interpretation |
|---|---|---|---|---|
| 4371 | 0.00 | negative | 1.42 | negative |
| 3594 | 0.00 | negative | 0.49 | negative |
| 2894 | 0.00 | negative | 0.82 | negative |
| 3302 | 0.00 | negative | 2.13 | positive |
| 3036 | 0.06 | negative | 2.00 | positive |
| 3306 | 0.00 | negative | 2.00 | positive |
| 3147 | 0.34 | negative | 2.81 | strong positive |
| 205 | 0.87 | inconclusive | 2.53 | strong positive |
| 4496 | 5.44 | strong positive | 2.50 | positive |

Example 3

Quantitative PCR for Identification of Johne's Disease

| Map Std 3 USDA kit 76 PAP1 10 pmol IS1311 (IS1&IS2) | | | | | | | | | | | |
|---|---|---|---|---|---|---|---|---|---|---|---|
| 1 | 2 | 3 | 4 | 5 | 6 | | | | 10 | 11 | 12 |
| Map Std $10^6$ | Map Std $10^5$ | Map Std $10^4$ | Map Std $10^6$ | Map Std $10^2$ | Map Std $10^1$ | 7 | 8 | 9 | Pos 0.33 ug/ul | Pos 0.33 ug/ul | Pos 0.33 ug/ul |
| 22.0 | 25.0 | 30.0 | 36.0 | 0.0 | 0.0 | | | | 19.4 | 18.9 | 18.2 |
| 76-1 | 76-1 | 76-2 | 76-2 | 76-3 | 76-3 | 76-4 | 76-4 | 76-6 | 76-6 | 76-7 | 76-7 |
| L | L | L | L | TNTC | TNTC | 0 | 0 | L | L | TNTC | TNTC |
| 30.1 | 27.5 | 30.3 | 28 | 32.1 | 29.5 | 0 | 0 | 35.7 | 33.6 | 29 | 26.7 |
| 76-8 | | 76-9 | 76-9 | 76-10 | 76-10 | 76-11 | 76-11 | 76-12 | 76-12 | 76-13 | 76-13 |
| 0 | 0 | + | + | M | M | fM | M | Mav | Mav | 0 | 0 |
| 0.0 | 0.0 | 30.4 | 30.9 | 35.7 | 34.2 | 29.1 | 27.1 | 23.5 | 22.6 | 0 | 0 |
| 76-14 | 76-14 | 76-15 | 76-15 | 76-16 | 76-16 | 76-17 | 76-17 | 76-18 | 76-18 | 76-19 | 76-19 |
| 0 | 0 | TNTC | TNTC | L | L | 0 | 0 | TNTC | TNTC | M | M |
| 0 | 0 | 30.7 | 29.3 | 29.2 | 29.2 | 0 | 0 | 33.2 | .30.9 | 38.5 | 35.4 |
| 76-20 | 76-20 | 76-21 | 76-21 | 76-22 | 76-22 | 76-23 | 76-23 | 76-24 | 76-24 | | |
| M | M | M | M | L | L | M | M | Mav | Mav | | |
| 31.6 | 30 | 33 | 31.6 | 31.1 | 28.6 | 36.2 | 0 | 24.9 | 23.8 | | |
| 76-25 | 76-25 | 76-26 | 76-26 | | | | | | | | |
| M | M | TNTC | TNTC | | | | | | | | |
| 29.1 | 28.1 | 30.2. | 28.6 | | | | | | | | |

The much referenced IS900 sequence (deemed specific to Map) provides diagnostic testing which identifies *Mycobacterium avium* subspecies *paratuberculosis* (Map). Another sequence, IS1311 offers the advantage of identifying both *Mycobacterium avium* subspecies *paratuberculosis* and *Mycobacterium avium* subspecies *avium* in one amplification, thereby reducing the time and expense of performing two separate test. The IS1311 sequence is basic to many mycobacteria. IS1/IS2 primers appear to identify pathogenic polymorphic mutation between Map and *M. avium* subspecies *avium* not detected by tests based upon the IS900 insertion sequence. The IS3/IS4 nested primers increase the sensitivity of the Map detection by primers based upon the IS1311 insertion sequence. The primers IS1/IS2 were therefore developed to meet our criteria of efficiency over culture analysis (seven hours vs. 42 days and extend the spectrum of organism identification. Standard direct PCR is not as efficient as real-time PCR. We have developed a labeled probe to function with our IS1/IS2 primers which enabled us to do real-time analysis which captures the stated diagnostic advantages stated above.

Example 4

ELISA Testing of Milk

This example identifies the correlation of Map DNA in milk based upon the J1J2 nested Map PCR technology and its correlation with its corresponding serum Map ELISA titer.

Materials and Methods:

Study Population: Blood and milk samples were obtained from 81 Holstein dairy cows in a dairy research unit (DRU)'s Holstein herd.

Sample Handling:

Raw Milk: Thirty-five to forty ml of milk was collected in a sterile 50 ml centrifuge tube from a randomly selected quarter by hand milking. Before collection, the teats were cleansed with alcohol. The first 10-15 ml of milk was discarded. The milk samples were centrifuged at 1000 g for 15 minutes and the supernatant discarded. The samples were washed three times using PBS (NaCL 43.3, Na2HPO4 11.4 g, KH2PO4 1.33 g, pH 7.3) and centrifuged at 500 g for 15 minutes. The pellet was re-suspended in 1 ml of PBS for cell counting, again centrifuged and re-suspended in 100 ul of 0.2 NaOH, boiled at 110 degrees Centigrade for 20 minutes to extract DNA, and centrifuged at 400 g for three minutes. Milk samples were collected over an approximately two and a half year period. For four cows, serial milk samples were collected over varying periods of time and analyzed using nested Map chain polymerase reaction test.

Blood Samples: After cleansing with alcohol, 7-10 ml of blood was collected from the coccygeal vein into Vacutainer tubes (R) containing EDTA. Three ml of whole blood was added to 4 ml of Ficoll-Isopaque™ Plus Gradient (Amersham Pharmacia, density 1.078 g/ml) and centrifuged for 30 to 40 minutes at 400 g at 18 degrees Centigrade. The buffy layer was removed. The cells were then washed twice in PBS, and centrifuged at 500 g for 15 minutes. Cells were counted with a hemocytometer, re-suspended in 100 ul of 0.2 NaOH, boiled at 110 degrees Centigrade for 20 minutes to extract DNA, and centrifuged at 400 g for 3 minutes. Neutralization was not attempted Agar Immunodiffusion Test (AGID): Petri dishes were poured with 1% agrose prepared in 0.1 M Tris-HCL buffer at pH 10. Well distances were 8 mm Well sizes were 4 mm for the six peripheral wells and 3 mm for the central well. The peripheral well received 45 ul of the test serum. The central well was inoculated with 35 ul of a crude protoplasmic antigen (Allied Monitor, Missouri). Serum from a cow with documented Johne's disease constituted the positive control. Final analytical readings were done at 24 and 48 hours. The appearance of one or more clearly definable precipitation lines before or at 48 hours constituted a positive result. Absence of any precipitation lines constituted a negative result.

Preabsorbed ELISA Test: The ELISA tests were performed using a crude soluble protoplasmic antigen (Allied Monitor, Missouri). Test sera were Preabsorbed with *Mycobacterium phlei*. ELISA results were calculated from absorbance at OD 405 nm. All readings less than 1.6 optical density (OD) had been deemed negative; readings between 1.5 and 1.99 OD were deemed suspicious/inconclusive; and readings above 2.0 to 2.5 OD were called low positive. A high positive was deemed any reading 2.51 OD or above.

Map Nesting (Polymerase Chain Reaction (PCR)):

Samples were probed with primers P90P91 which recognized a 413 bp sequence of *Mycobacterium avium* subspecies *paratuberculosis* followed by a second set of primers J1J2 which overlapped and spanned a 333 base pair region within the insertion sequence. Primer exactness was checked using two sets of primers. Additional primer exactness was tested by submitting original samples to a set of P1P2 primers, recognizing a 427 bp sequence (IS1245) of *Mycobacterium avium* subspecies *paratuberculosis* (Map) and a third set of primers, DD2, DD3, probing for insertion sequence IS1311 which identifies a 180 bp sequence shared by Map. PCR products were sequenced (ICBR, University of Florida) for nucleotide homology using GenBank as the database. Homologies of 100% were obtained (Buergelt and Williams, 2004, Australian Vet. J. 82:497-503).

Results:

Prevalence of Map in Milk Based on Single Specimen Analysis: Of the 81 dairy cows sampled with J1J2 nested PCR technology, 19 cows had Map DNA detected in the milk. The individual milk samples were compared with corresponding ELISA titers (Table 2). ELISA titers determined to be negative suspicious, positive and strong positive resulted in 4 (20%), 2 (15.4%), 2 (11.8%), and 9 (29%) milk samples being positive for Map DNA. The number of ELISA titers which tested negative for Map DNA in milk was 20, 13, 17 and 31, respectively. The best correlation between Map DNA in milk and corresponding serum ELISA titer on a single milk sample existed for samples with strong positive serum ELISA titers.

Observations of Map DNA in Milk Based upon Serial Specimens: Multiple milk samples were available on 81 dairy cows. In each case, Map was identified in two milk samples collected on separate dates. Four cows had greater than four specimens available for analysis (Tables 2, 3, and 4). Cow 3900 was monitored from July 2002 into November 2004. In those 45 months, Map was identified in its milk on four separate occasions.

Map Shedding From Individual Teats: Cow #6142 milk samples were obtained from its individual teats on six separate days (Table 5). While overall shedding was constant over 133 days, individual teats were negative on sampling. During the observation period, the ELISA titers varied between a high of 2.97 and 1.5.

Correlation Between Map DNA in Milk and Necropsy Pathology:

Nine dairy cows which had Map identified in one or more milk samples came to necropsy. Johne's disease was documented in all 9 cases.

Discussion: ELISA testing has been advocated as a voluntary herd management tool upon which individual producers could make decisions. An arbitrary absorbance value is thought to determine which animals are at greatest risk to the herd. The commercially licensed Map ELISA tests are used as herd management tools. Collins et al. have proposed that Map ELISA testing be used to remove the cows which are most infectious and not likely to survive another lactation (Collins, 2005, Clin. Diagn. Immunol. 12: 685-692). The underlying premise to this approach is that by removing the sickest animal, intra-herd dissemination of Map will be retarded. Fecal direct and nest polymerase chain reaction (PCR), fecal culture, and serological tests identify dairy cows which are infected with Map. Given the widespread prevalence of Map infection in large dairy herds and the potential from environmental re-introduction of Map into newly created dairy herds render total elimination of all infected animal as a short-term difficult goal.

If selected emphasis is to be given to testing, a primary focus may be to eliminate those infected animal with subclinical disease which, in theory, constitute the greatest potential to introduce Map into the human food chain as well as enhance environmental contamination and intra-herd dissemination of Map. Cows with Map demonstrable in their milk constitute such animals.

From the data presented, a given ELISA titer has limited relevance as to whether or not a given cow is shedding Map into its milk. Based upon necropsy confirmation of established Johne's disease, the presence of Map antigen in milk appears to document prior spread of Map from the gastrointestinal tract. All nine cows for which subsequent necropsy reports became available demonstrated disseminated disease. Additionally, Map shedding into milk cannot be ascertained from a single milk sample. Map shedding can be irregular over an extended period of monitoring. A single negative nested Map PCR test does not rule out subsequent Map shedding into milk. To enhance a correct assessment as to the presence or absence of Map within milk from a given dairy cow requires multiple, individual milk sample, obtained at different dates being tested.

Another factor apparently affecting the presence or absence of Map in milk is the means by which a given sample is obtained. For a milk sample to be deemed adequate for analysis, the milk should be obtained from all four teats (pooled samples) and concentrated to increase the chances of detecting infected milk samples.

The observation of periods of Map shedding into milk, interspersed with periods of non-shedding, strongly suggests the importance of such factors as diet and/or environmental stress in governing a cow's ability to deal effectively with Map.

TABLE 2

Correlation of Serum Map ELISA Titers and Detection of Map DNA in Individual Milk Samples

| ELISA Titer Serum | Nested PCR | | |
|---|---|---|---|
| | Number of Negative Tests | Number of Positive Tests | Percentage |
| less than 1.6 (negative) | 20 | 4 | 20% |
| 1.6-1.99 (suspicious) | 13 | 2 | 15.4% |
| 2.0-2.5 (positive) | 17 | 2 | 11.8% |
| greater than 2.51 (strong positive) | 31 | 9 | 29% |

TABLE 3

Longitudinal Observations of Map DNA in Milk

| Cow #3900 | Specimen Date | ELISA Titer | Nesting Milk PCR | AGID |
|---|---|---|---|---|
| | Jul. 23, 2002** | 3.1 | negative | negative |
| | Apr. 01, 2003** | 2.7 | negative | negative |
| | Apr. 28, 2003 | 6.1 | positive | negative |
| | Jun. 2, 2003 | 3.1 | negative | negative |
| | Jul. 1, 2003 | 3.7 | negative | negative |
| | Jul. 22, 2003 | 3.0 | negative | negative |
| | Feb. 17, 2004 | 2.76 | negative | negative |
| | Mar. 8, 2004** | 1.59 | positive | negative |
| | Mar. 22, 2004 | 2.85 | positive | negative |

TABLE 3-continued

Longitudinal Observations of Map DNA in Milk

| Cow #3900 Specimen Date | ELISA Titer | Nesting Milk PCR | AGID |
|---|---|---|---|
| Apr. 20, 2004 | 2.68 | negative | negative |
| Jul. 1, 2004 | 3.55 | negative | negative |
| Aug. 3, 2004** | 3.98 | negative | positive |
| Aug. 25, 2004 | 5.54 | positive | positive |
| Oct. 13, 2004 | 2.4 | negative | positive |

*Johne's disease documented at necropsy
**Map DNA identified within white blood cells by nested J1J2 PCR

TABLE 4

Serial Observations of Map DNA in Milk

| Cow Number | Date | Serum ELISA Titer | Nested Milk PCR | AGID |
|---|---|---|---|---|
| #3763* | Sep. 10, 2003 | 1.8*** | positive | negative |
|  | Sep. 12, 2003 | 1.5** | positive | negative |
|  | Sep. 15, 2003 | 1.3** | positive | negative |
|  | Sep. 16, 2003 | less than control | positive | negative |
|  | Sep. 17, 2003 | 1.45** | negative | negative |
|  | Sep. 18, 2003 | 1.66*** | positive | negative |
| #3485* | Sep. 25, 2003 | 1.68*** | negative | negative |
|  | Sep. 26, 2003 | 1.85*** | positive | negative |
|  | Sep. 29, 2003 | 1.5** | positive | negative |
|  | Sep. 30, 2003 | 1.84*** | negative | negative |
|  | Oct. 1, 2003 | 1.9*** | negative | negative |
|  | Oct. 2, 2003 | 1.6*** | negative | negative |
| #3838* | Oct. 15, 2003 | 5.6**** | positive | positive |
|  | Oct. 16, 2003 | 5.8**** | negative | positive |
|  | Oct. 17, 2003 | 4.4**** | negative | positive |
|  | Oct. 21, 2003 | 4.4**** | negative | positive |
|  | Oct. 22, 2003 | 4.9**** | positive | positive |
|  | Oct. 23, 2003 | 4.9**** | negative | positive |
|  | Oct. 24, 2003 | 4.9**** | negative | positive |

Johne's disease confirmed at necropsy
**ELISA titer deemed negative (0-1.5)
***ELISA titer deemed suspicious (1.6-1.99)
****ELISA tier deemed strongly positive (greater than 2.51)

TABLE 5

Identification of Map DNA in Milk by Nested PCR From Individual Teats Cow # 6142

| Date | Nested PCR | | | | ELISA | |
|---|---|---|---|---|---|---|
|  | RF | LF | LR | RR | Titer | AGID |
| Sep. 24, 2002 | + | + | − | + | 2.97**** | + |
| Dec. 10, 2002 | − | + | − | − | 1.5** | + |
| Dec. 30, 2002 | + | + | − | + | 2.0** | + |
| Jan. 21, 2003 | + | + | + | + | 2.68**** | − |
| Jan. 28, 2003 | + | + | + | + | 2.5***** | − |
| Feb. 4, 2003 | nt | − | − | − | 2.3***** | − |

RF = right front teat;
LF = left front teat;
LR = left rear teat;
RR = right rear teat
nt = not tested
+ = positive
− = negative
*Johne's disease documented at necropsy
**ELISA titer deemed negative (O-1.5)
***ELISA titer deemed suspicious (1.6-1.99)
****ELISA tier deemed strong positive (greater than 2.51)
*****ELISA titer deemed positive (2.0-2.5)

Example 5

Comparison of Two Direct Nested PCR Tests for the Detection of *Mycobacterium Avium* Subspecies *Paratuberculosis* in Bovine Feces Material and Methods:

Samples Analyzed: Four separate USDA Certification Kits, containing bovine fecal samples were analyzed. Kit number #1 (#F1—25 samples) was specifically created by USDA for the University of Florida College of Veterinary Medicine (UFCVM). Kits number #2 (#101—26 samples), and kit number #3 (#105—26 samples) were sent to a second UFCVM laboratory where they were tested for the presence of Map DNA by direct nested PCR. For the three sets of samples the investigators were blinded to the as to the code in each study.

DNA Extraction and PCR Procedure: All fecal extractions were done according to instructions from Mo Bio Laboratory Products Carlsbad, Calif.). Fecal samples were subjected to beating followed by a series of solutions for cell lysis, organic and inorganic precipitation. Binding of the DNA was achieved using a silica membrane with a high salt solution. DNA was then washed with an ethanol solution and eluded with an elution buffer. Samples were probed with two pairs P90-P91 with nested primers J1-J2 and IS1-IS2 with nested primers IS3-IS4, U.S. Published Application No. US-2010-0021897 (published on Jan. 28, 2010).

Primers: Primers P90-P91 specifically recognize a 413 base pair sequence of Map IS900. Primers J1-J2 overlap and span a 333 base pair region within the insertion sequence. Primers IS1-IS2 recognize a 242 base pair sequence of Map IS1311 and primers IS3-IS4 overlap and span a 104 base pair region within the insertion sequence. Positive and negative controls were used in each of the reactions.

Statistical Analysis: Kappa coefficient was used as a measure of agreement between direct fecal nested Map PCR test results and kits keys provided by USDA. For this study, the test results provided by USDA were considered as "true" state of infection. The following categories were used for kappa test interpretation: poor agreement: less than 0.20; fair agreement: 0.21 to 0.40; moderate agreement: 0.41 to 0.60; good agreement: 0.61 to 0.80; very good agreement: 0.80 to 1.00. Fisher's Exact Test was used to test whether there was any non-random association between both variables of the two direct fecal nested Map PCR test results and provided culture results. This test was chosen because in all the cases the tables were highly imbalanced (low values in the cell for both variables). The right-sided probability value was used considering the alternative hypothesis of a positive association between both results (observations tending to lie in upper and lower right cells of the 2×2 contingency table). Data were analyzed using SAS statistical package for Windows (Version 9.00) using the PROC FREQ procedure. Values of P less than 0.05 were considered significant for all tests.

In the analysis, sensitivity and specificity of direct fecal nested Map PCR tests were estimated as a gold standard, the kit key for each specimen as negative as negative or to positive to infection. Kappa coefficient, sensitivity and specificity were estimated using Win Episcope 2.0 software (Win Episcope 2.0). Ninety-five percent confidence intervals (CI) were constructed for all estimates.

Results:

Estimation of sensitivity and specificity and kappa coefficients for the samples from kits 1 to 3 for the two direct fecal nested Map PCR test results with keys provided by USDA are presented in Table 6.

Fisher's Exact Test used to test the null hypothesis of no association between nested PCR tests (J1-J2 and IS3-IS4) and origin laboratory key in p-values less than 0.0001 for both cases. The data indicates that in two cases there was sufficient evidence to reject the null hypothesis (i.e., there was significant statistical association between results of nested PCR tests and origin laboratory key). The agreement between FecaMap test results and fecal culture provided by USDA was good for both sets of primers.

Table 7 defines the comparison sensitivity data presented in terms of false positive and false negative results observed in the three USDA laboratory certification kits. Table 8 reports the approximate time requirement for removal of the PCR inhibitors in feces and PCR testing achieved using the FecaMap™ system in doing ten fecal specimens.

Discussion: The U.S herd management response to combat Johne's disease has been to advocate a voluntary policy of selective herd testing. The commercially licensed Map ELISA test are not diagnostic tests, but rather herd management tests. In theory, their function is to contribute to overall herd welfare. Additionally, it has been proposed that Map ELISA testing be used to remove the cows which are most infectious and not likely to survive another lactation. The underlying premise to this approach is that by removing the sickest animal, over time, natural selection would take over.

The ELISA tests currently available lack acceptable sensitivity. In an evaluation of five antibody detection tests for the diagnosis of bovine *paratuberculosis* using serum samples from 359 dairy cattle in seven *paratuberculosis*-free herds and 2,094 cattle in seven Map-infected dairy herds, it was determined that the antibody tests lacked acceptable sensitivity (Collins et al., 2005, Clin. Diagn. Immunol. 12:685-692). Both the ParaCheck (Biocor, Omaha, Nebr.) and HerdCheck (IDEXX Laboratories Inc. Westbrook, Me.) ELISA tests done in accordance with manufacturers' instruction and interpreted as prescribed by the kit insert, identified less than 29% of fecal culture positive cows. Diagnostic specificity among the five ELISA tests evaluate ranged from 84.7% to 86.5%. Linear regression analysis of quantitative results showed a low correlation co-efficiency. A more positive relationship could be shown between the number of *mycobacterium* in feces and ELISA positivity. With low number of Map in their feces, a mean of 13.3% of infected cows were ELISA positive. At progressively higher fecal culture scores, the mean percentage of positive antibody assays were 27.3% 54.9% and 78.4% respectively.

A variable affecting statistical analysis was the inclusion in the USDA fecal samples of a specimen heavily spiked with *M. avium* which was detected by both nested J1-J2 and IS3-IS4 but not P90-P91. Comparable results were achieved with another set of base and nested IS900 primers under development in our laboratory. Despite the inclusion of the *M. avium* spiked sample, the P90-P91/J1-J2 combination's sensitivity were 89.3% and 90.5% whereas those of the IS1-IS2/IS3-IS4 combination were 96.4% and 95.2% respectively with a fecal culture vs. PCR Kappa value of 0.903.

A potential drawback to the utilization of the nested J1-J2, or IS3-IS4) which are based upon the IS 900 and IS1311 sequence respectively is that all nested primers tested in-house to date have identified *M. avium*, when the organism is spiked into diagnostic fecal specimens.

The FecaMap™ sets of primers are based on the IS1311 sequence. Nevertheless, the IS1452 primers show a demonstrable superiority in comparison to the IS900 P90-P91 pairing. The IS1311 primer pairs identify only 6-8 copies whereas primers based upon the IS900 sequence identify 14-18 copies. A case can be argued USDA's insistence on near absolute specificity for Map has resulted in development of specificity for Map refined done at the expense of sensitivity.

The current study indicates that selective strains of Map may have genetic constituency not adequately identified by IS900 sequence based primers. Herman-Taylor's theory that the incorporation of foreign DNA into *M. avium* lead to ultimate evolution of the Map phenotype appears to have a real foundation based upon the comparison of the base primers studied. Primers which identified both Map and *M. avium* identified more positive USDA fecal samples than did those based foreign DNA encompassed in the IS 900 sequence into background *M. avium* species led to the development of current Map phenotype. The *M. avium* based test produced a statistically significant rate of correspondence in sera from necropsy documented cows (67%). The Paracheck Map ELISA test identified only 11% of the diseased animals.

With respect to limitation of Map intra-herd dissemination or protection of a nation's food supply, there is no effective herd management schema in place. The development of direct fecal nested PCR tests and possibly the EVELISA test provide a potential foundation for development of herd management schema which are applicable to these two, under-addressed issues. The direct fecal nested Map PCR test process, FecaMap™, produces results in seven hours or less. With conversion of the test to automation, the time required can be significantly reduced.

TABLE 6

Statistical comparison of P90-P91/J1-J2 versus IS1-IS2/IS3-IS4 primers on three USDA laboratory certification kit fecal specimens

| | P90-P91/J1-J2 | IS1-IS2/IS3-IS4 |
|---|---|---|
| Sensitivity | 89.3% | 96.5% |
| Specificity | 90.5% | 95.2% |
| Kappa Coefficient | 0.753 | 0.903 |
| Interpretation | Good agreement | Very good agreement |

TABLE 7

Comparison of primers P90-P91, IS1-IS2, P90-P91/J1-J2 and IS1-IS2/IS3-IS4 false positive and false negative observed on three USDA certification kit fecal specimens

| | Primers | | | |
|---|---|---|---|---|
| | P90-P91 | IS1-IS2 | P90-P91/J1-J2 | IS1-IS2/IS3-IS4 |
| False Positive | 20 | 26 | 2 | 1* |
| False Negative | 81 | 75 | 6 | 2 |

*Specimen heavily spiked with *M. avium*

TABLE 8

Time requirement for removal of fecal PCR inhibitors and PCR testing (n = 10).

| Procedure | Time Required |
|---|---|
| 1. Decontamination | 90 minutes |
| 2. PCR | 120 minutes |
| 3. Nested PCR* | 120 minutes |
| 4. Gel for nesting | See above |
| Approximate Total Time To Results | 7 hours |

*(including concomitant gel preparation)

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 6

FUIDI Data Hypothesis

Current USDA sanctioned tests identify a titer of Map antibody chosen to protect the manufacturers from a false-positive test result. However, neither the Map ELISA manufacturers nor USDA have publically defined the significance of a "negative" Map test.

The natural history of Map infection has been constructed on limited serological data and relatively insensitive *mycobacterium* culture isolation technology. The present invention is based, at least in part, upon the FUIDI Map ELISA tests and the resultant application in an epidemiological field trial.

One thousand, one hundred and thirteen dairy cows within USDA's Florida Dairy Herd Demonstration Project were analyzed using the FUIDI #2 ELISA test component of the FUIDI Herd Management Schema (U.S. Pat. No. 8,143,012 (Monif) and U.S. Pat. No. 8,008,033 (Monif), which are incorporated herein by reference in their entirety). The FUIDI #2 test identified 110 animals as having some level of either ongoing or very recent Map replication. Of these 110 cows, 9 cows were designated as having significant ongoing infection and 6 cows were designated as being suspicious for having significant infection by the FUIDI #2 test.

Fourteen months later, 661 of the original 1,113 cows were available for re-analysis. Of the 91 cows previously identified by the FUIDI #2 test as having low or non-diagnostic evidence of significant infection 54 were available for re-evaluation. Of these 54 cows, 45 (83%) had lost all evidence indicative of active infection; 8 (14.8%) exhibited evidence of continuing low level active infection; and 2 (3.7%) attained evidence indicative of significant active infection.

Of the 13 cows initially identified by the FUIDI #2 test as being suspicious of or having significant active infection 6 cows had been retained in the herd for production purposes. Fourteen months later, all 6 cows ceased to have evidence of ongoing Map replication in the FUIDI #2 test.

Of the remaining 540 cows that had previously tested negative, 18.9% developed evidence of active infection.
The FUIDI study data demonstrated that:

1) transient infection occurs commonly within a large dairy herd;
2) over time, the prevalence of infection of previous uninfected animals is progressive;
3) the vast majority of herbivores ingesting pathogenic *mycobacterium* from the environment or from their food source achieve immune governance over the organism in a manner similar to the human model system with *M. tuberculosis*; and
4) the characterization of Johne's disease as being a chronic progressive disease has eclipsed perception that, like in human model system with *Mycobacterium tuberculosis* infection, the majority of infected hosts are able to attain non-eradication immune governance over Map. As with humans, reactivation of infection can occur if the animal's immune system is compromised. Parturitions coupled with environmental stress and/or nutritional deficiencies are potential triggers in dairy cattle for reactivation or conversion from subclinical active disease to its overt diarrhea syndrome.

The FUIDI data hypothesis is the basis for using the extension of the FUIDI Herd Management Schema beyond a schema that primarily benefits the producers of milk and milk products to one that better serves the public health interest of the consumers of milk and milk products.

Example 7

Map is Required, but not Sufficient, for Enteric Disease in Cows

In the USDA's mycobacterium isolates achieved from 2009-2010, thirty-six isolates from cows: 10 *M. hominissuis*: 2 Map, 5 *M. avium, and the rest undetermined, of which at least* 7 appear to be within the Mycobacterium avium complex (Mac) grouping. The samples are likely tissue or biological fluids. If the source had been fecal, the unknowns would have been discarded as such. Of the 18 isolates known to have been from tissue of diseased animals, the breakdown is as follows: Map 2 with another called possible even thought it was not identified by IS900 primers, 10 undetermined, and 5 *M. hominissuis*.

Any way the data is interpreted, it is clear that Map is a cause of enteric disease, but is not the cause of enteric disease in cows. This is why testing of bulk milk with IS1311 primers is extremely useful and an important component of the methods of the invention. The methods of the invention address the producer's desire to minimize the adverse economic consequences at the herd level, and also diminish the public health risk and producer's potential liability.

TABLE 9

USDA MYCOBACTERIUM ISOLATIONS FROM COWS AS COMPUTED BY INFECTIOUS DISEASES, INCORPORATED (IDI)
Years: 2009-2010

| | Specimen # | Source | Isolate | Map02 | IS900 |
|---|---|---|---|---|---|
| #1 | 09 4622 | Bakersfield CA | 99% *M. intercellulaire* | neg | neg |
| #2 | 09 8165 | MI | Map | POS | POS |
| #3 | 09 5732 | Floresville TX | undetermined | neg | neg |
| #4 | 09 6206 | CARGILL (Wyalusing PA) | Map | POS | POS |
| #5 | 09 10305 | Bill Owen Livestock, Mountainair NM | ?? *M. para* | neg | neg |
| #6 | 09 4418 | PA | *M. avium* | POS | neg |
| #7 | 09 4786 | Franklin Meats Franklin WI | undetermined | POS | neg |
| #8 | 09 5433 | TX | *M. avium* | neg | neg |
| #9 | 09 5433 | TX | 99% *M. intercellulaire* | neg | neg |
| #11 | 09 5894 | TX | *M. hominissuis* | POS | neg |
| #12 | 095909 | TX | undetermined (99% *M. chimaera*) | neg | neg |

TABLE 9-continued

USDA MYCOBACTERIUM ISOLATIONS FROM COWS AS COMPUTED BY
INFECTIOUS DISEASES, INCORPORATED (IDI)
Years: 2009-2010

| | Specimen # | Source | Isolate | Map02 | IS900 |
|---|---|---|---|---|---|
| #13 | 09 8126 | Florida Beef Inc. Zolfo Springs FL | undetermined (99% *M. intercellulaire*) | neg | neg |
| #14 | 09 8223 | Texas A&M TX | undetermined | neg | neg |
| #15 | 10 0204 | Ferndale CA | *M. hominissuis* | neg | neg |
| #16 | 10 0824 | MO | *M avium* | POS | neg |
| #17 | 10 1068 | St. Paul MN | *M. hominissuis* | neg | neg |
| #18 | 10 1112 | Fayetteville AK | *M. hominissuis* | POS | neg |
| #19 | 10 1137 | CARGILL Wyalusing PA | *M. hominissuis* | POS | neg |
| #20 | 10-1316 | undetermined | (995 *M. intercellulaire*) | neg | neg |
| #21 | 10-1377 | London KY? | *M. avium* | POS | neg |
| #22 | 10-1708 | CA | *M. hominissuis* | POS | neg |
| #23 | 10 1725 | JBS Packerland Souderton PA | M/*hominissuis* | neg | neg |
| #24 | 10-1737 | CARGILL Milwaukee WI | undetermined (99% *M. intercellulaire*) | neg | neg |
| #25 | 102173 | Pigeon MI | *M. hominissuis* | POS | neg |
| #26 | 10 3208 | La Junta CA | undetermined (99% *M. intercellulaire*) | neg | neg |
| #27 | 10 3369 | CO | *M. hominissuis* | neg | neg |
| #28 | 10 3409 | Dimmitt TX | undetermined (99% *M. intercellulaire*) | neg | neg |
| #29 | 10 3425 | Harrisburg MS | *M. hominissuis* | neg | neg |
| #30 | 10 3770 | JBS Packerland Souderton PA | undetermined | neg | neg |
| #31 | 10 4377 | L & H Packing San Antonio TX | undetermined | neg | neg |
| #32 | 10 4743 | CARGILL Taylor Beef Wyalusing PA | undetermined | neg | neg |
| #33 | 10 4912 | MO | *M. hominissuis* | POS | neg |
| #34 | 10 5027 | CARGILL Taylor Beef Wyalusing PA | undetermined | neg | neg |
| #35 | 10-5432 | Alberta Canada | *M. hominissuis* | neg | neg |
| #36 | 09 4604 | ID | *M. avium* | POS | neg |

BLAST = MAC/MEGA = *M. hominissuis*
BLAST = MAC/MEGA = *M. avium*
BLAST = MAC/MEGA = Map

TABLE 10

Documented Necropsy Source USDA Isolation Data 2009-2010

| Case# | Location | Organism |
|---|---|---|
| #16 | Cargill Taylor Beef Wyalusing PA | Map |
| #18 | Sioux Falls Regional Livestock Worthington SD | *M. hominissuis* |
| #23 | Zumbrota Sale Barn Zumbrota MN | *M. hominissuis* |
| #25 | Cargill Taylor Beef, Wyalusing PA | undetermined |
| #26 | Packerland Souderton PA | undetermined |
| #27 | Bill Owen Livestock Mountainair NM | ? Map but neg IS900 |
| #34 | JBS Packerland Souderton PA | undetermined but positive IS900 |
| #46 | Florida Beef Inc. Zolfo Fl | undetermined |
| #47 | Texas A7 M | undetermined |
| #64 | Cargill Taylor Beef Wyalusing PA | *M. hominissuis* |
| #71 | Feeders Rio Grande City TX | *M. hominissuis* |
| #72 | JBS Packerland Souderton PA | *M. hominissuis* |
| #73 | Cargill Milwaukee Wi | uncut/undetermined |
| #83 | JBS Packerland Souderton PA | undetermined |
| #87 | FPL Food LLC Augusta GA | undetermined |
| #88 | L & H Packing San Antonio TX | undetermined |
| (#91 | Taylor Beef Wyalusing PA | not a *mycobacterium*) |
| #93 | Taylor Beef Wyalusing PA | undetermined |

*Mycobacterium* Isolated from 17 Necropsy samples from Diseased Cows
Map 2 (one not confirmed by IS900)
Undetermined 10
*M. avium* 0
*M. hominissuis* 5
Single Source of Specimen with Disease Identified at Necropsy
Cargill—Taylor Beef Wyalusing Pa.
Map
Undetermined
*M. hominissuis*
Undetermined Example 8

Evaluation of USDA-Certified Diagnostic Map Tests

The 2008 National Johne's Disease Control Program Strategic Plan identified three specific goals:

1. Reduce the prevalence of Map/Johne's disease in the national herd
2. Reduce the impact of Johne's disease on individual herds
3. Reduce the risk of introducing Johne's Disease to uninfected herds (Schwartz A.: *National Johne's Disease Control Program Strategic Plan*. Oct. 23, 2008. Page 1). The National Johne's Disease Control Program has failed in meeting two of the three of its stated goal objectives.

The current commercial Map ELISA tests certified by the United States Department of Agriculture (USDA) measure anti-Map antibodies; however, the interpretation of a positive test is predicated on the identification of a level of antibody that predicts a high probability of a progression of Map infection to clinically overt enteritis or confirmation of its presence. A negative commercial Map ELISA test does not address the issue of whether or not a given animal has ever been infected by Map. The decision by USDA to have the Map ELISA tests represent a statement of probability rather than a valid measurement of the amount of antibody present permitted infected cows to be transported across state lines and national borders. The net result was not only the introduction of infected animal into uninfected herds, but an increased prevalence of Map infection in the national herds. In 2007, USDA acknowledged that an estimated 70% of U.S. dairy herds contained one or more infected animals (USDA-APHIS Johne's Disease in U.S. Dairies 1991-2007. USDA Animal and Plant Health Inspection Service website).

Central in the herd monitoring schema proposed by the National Johne's Disease Control Program for Johne's disease was identification and removal of infected animals from the herd. When producers truly participated in a herd monitoring schema, the incidence of Johne's disease was effectively reduced; however, once federal funding for Map testing was withdrawn, continued participation all but collapse.

Educationally, any basic knowledge disseminated among producers as to Map's negative impact on milk production, reproductive outcomes, and enhancement of slaughter weight has not been effectively translated into significant modification of existing herd management schema. To achieve the benefits of a herd monitoring schema, a producer now has to spend the farm's money upfront. Without a national stated policy, the Map test data potentially exposes producers to potential liability when it comes to the quality of farm's milk and the slaughter value of cows being removed from the herd.

Reducing the introduction of Map infection and potentially Johne's disease into uninfected herds is largely contingent upon the buyer having the proper information to go along with eyeball analysis of the animal's body condition score. Effective national standards for bovine product warranty are not in place. Quality of merchandise is theoretically addressed through the animal's health certificate. On the federal level, revision to part 71 and 80 of the Code of Federal Regulations (CFR) is supposed to restrict the interstate movement of Map-infected animals except to recognized slaughter establishments (United States Department of Agriculture Animal Plant Health Inspection Service. 9, Parts 71 and 80.2000. *Johne's disease in domestic animals: interstate movement*. Federal register 65.18875-188879). With an artificially constitute threshold for a positive test, the pertinent CFR regulations do not truly address the quality of merchandise issue. Too often on the state level, state animal health certificates merely require that the certificate be signed by a veterinarian attesting to the apparent absence of any contagious or otherwise transmissible disease. The language in many state health certificates tends to minimize any requirement that the animal be free of underlying infectious diseases. The principle exception is the Wisconsin Implied Warranty law that stipulates that cattle to be sold are guaranteed to be Map-free unless sellers provide a written retraction of this guarantee at the time of the sale (Sockett D. C.: *Johne's disease eradication and control: regulatory implications*. 1996. *Vet. Clin. North Am. Food Anim. Pract.* 12:431-440).

By not stipulating on the animal's certificate of health, its Map status in a manner comparable to *Mycobacterium bovis*, animals with subclinical disease animal are and have been transported interstate and national boundaries. The decision by USDA not to require a statement as to an animal's Map status has been a prime factor that undermined its avowed intent to prevent dissemination of Map into uninfected herds. Infected animals with subclinical infection are shipped across state lines with relative impunity.

The Japanese perception that Map constitutes a potential public health hazard has engendered a different schema (Eiichi M. 2012. *Epidemiological situation and control strategies for paratuberculosis in Japan. Japanese J. Vit. Res.* 60:19s-29s). In accordance with the Act on Domestic Animal Infectious Disease Control, after 1998, every Japanese dairy farm is examined for Map every five years. Imported cattle are subjected to quarantine in which they are screened using Map ELISA, fecal bacterial culture, analysis of feces for Map DNA and Johnin skin test. If a new cow is to be introduced into a herd, the recommended procedure is that the cow should be negative in more than two ELISA tests within three-month interval during the last six months, negative at least once in culture for Map, and kept in quarantine until proven non-infectious. Fifty-four percent of diseased animal detected by the Japanese Animal Quarantine Service came from the United States. Owing to the high antibody threshold for a positive test of the current Map ELISA tests, the real number of infected cows from the United States escaping detection is open to speculation.

Once Map is introduced into the pasture/production environment, its elimination is extraordinarily difficult (Eisenber S. W. F., Nielsen M., Santema W. Houwers D. L., Heederik D., Koets A. P.: *Detection of spatial and temporal spread of Mycobacterium avium subsp. paratuberculosis in the environment of a cattle farm through bio-aerosols. Vet. Microbiol.* 2010; 143:284-292). Even if elimination of Map could be achieved, the ultimate reservoir of infection cannot be eradicated. What has now been shown is that *Mycobacterium avium* subspecies *paratuberculosis* infection in dairy herds acts much like *Mycobacterium tuberculosis* in human: Disease is a small percentage of infection (Monif G. R. G., Williams J. E.: *The natural history of Mycobacterium avium subspecies paratuberculosis as interpreted by the FUIDI #2Map test. Proceedings of* 10*th ICP.* 2009; p. 164). Once a resident animal within a confined herd develops Johne's disease, the FUIDI #1 Map ELISA test can demonstrate that a significant number of animals within the herd have had antigenic exposure to Map. Quantitative determination of the amount of anti-Map antibodies by the FUIDI #1 Map ELISA test is, at best, a poor indicator of whether an animal is infectious, rather than having been infected. A positive PPD does not mean that an individual has active tuberculosis. An indication of relative infectiousness can be derived from concomitant test using the FUIDI #2.

The European Union, the European national authorities, if not the world are significantly influenced by the USDA edits as they relate to testing for *Mycobacterium avium* subspecies *paratuberculosis*. USDA's certification of Map diagnostic tests is presumed to be based on conclusive scientific data. The presumed hypothesis embedded in Map diagnostic tests has been that they identify the pathogenic mycobacteria that cause Johne's infect/disease in herbivores.

Published data has demonstrated a positive correlation between a positive HerdChek® and ParaChek® in cows and clinically overt or necropsy documented Johne's disease. A number of unanswered questions exist:

1. Why the poor correlation between clinical status and serological Map tests? McKenna et al. tested sera collected from dairy cows at slaughter using three commercial Map ELISA tests that included HerdChek® and ParaChek®. They found overall poor agreement between the three ELISA tests and slaughter status (McKenna S. L. B., Backema H. W., Keefe G. P., Sockett D. C.: *Agreement between three ELISA tests for Mycobacterium avium subspecies paratuberculosis in cattle. Vet. Microbiol.* 2006; 31:285-291). Collins et al. evaluated five Map antibody tests using serum samples from 359 dairy cattle in Sven reputed *paratuberculosis*-free herd and 2. dairy cattle in Seven Map-infected herds. ParaChek® and HerdChek® identified less than 29% of culture positive cows (Collins M. T., Wells S. J., Petrini K. R., Collins J. E., Schultz R. D., Whitlock R. H.: *Evaluation of five antibody detection tests for the diagnosis of bovine paratuberculosis. Clin. Diagn. Immunol.* 2005; 31:285-291). Sweeney et al. suggested that commercial Map ELIDA sensitivity might be lower than 13.5% (Sweeney R. W., Whitlock R. H., McAdams S., Fyock T.: *Longitudinal study of ELISA seroreactivity to Mycobacterium avium subspecies paratuberculosis in infected cattle and culture-negative herd mates. J. Vet. Diagn. Invest* 2006; 18:2-6).
2. If *Mycobacterium avium* subspecies *paratuberculosis* (Map) is the cause of chronic granulomatous enteritis (Johne's disease) in herbivores, why are occasional tissue *mycobacterium* isolates from diseased cows not identified by primer based on the IS900 insertion sequence disregarded as pathogens? The first corollary of the scientific method is that a scientific truth must encompass all exceptions.

Experiment # I: Evaluation of USDA Certified Map ELISA Tests

The current commercial Map ELISA tests certified by the United States Department of Agriculture (USDA) measure anti-Map antibodies, but the interpretation of a positive test is predicated on the identification of a level of antibody that predicts a high probability of a progression of Map infection to clinically overt enteritis or confirmation of disease.

Problem: A negative commercial Map ELISA test does not address the issue of whether or not a given animal has ever been infected by Map.

Embedded in earlier studies is the hypothesis that the current commercial Map ELISA tests' threshold for positivity precludes these tests from being used to state whether a given animal has been infected by Map.

The experiment design used to challenge the hypothesis was that of a comparative analysis between Prionic's ParaChek® and IDI's pre-FUIDI #1 Map ELISA tests done on the same serum sample. The pre-FUIDI #1 test was done at the University of Florida College of Veterinary Medicine, The ParaChek® testing was done at the State of Florida; Veterinary Diagnostic Laboratory in accordance to the manufacturer's instructions. Both laboratories were blinded as to the other's results. The pre-FUIDI#1 Map ELISA test's accuracy had been confirmed by USDA's 2007 and 2008 Laboratory Certification t for Map Serology. In 2009, the FUIDI#1 Map ELISA test had a perfect score on USDA's test.

The study population was drawn from sera drawn from two adjacent dairies in South Florida. Dairy #1 herd had aggressively managed using USDA's policy of test-and-cull and was considered to be Map free, Dairy #2 herd was known to have had Johne's diseased cows in recent past. The test sera were first sent to the State of Florida Veterinary Diagnostic Laboratory in Live Oak, Fla. and subsequently rerouted to Veterinary Diagnostic Laboratory at the University of Florida College of Veterinary Medicine.

All 26 sera from Dairy #1 herd tested negative in the ParaChek® Map ELISA test. Ten of these 26 sera had a significant antibody titer that was categorized as being positive by the pre-FUIDI #1. An additional three sera had anti-Map antibodies below the pre-FUIDI arbitrary cut off point for positive levels derived from serial testing of animals that developed necropsy confirmed Johne's disease.

Of the 22 sera from Dairy #2, the ParaChek® test identified two as being positive and an additional 10 as suspicious. The pre-FUIDI test identified 16 as positive and an additional 3 as having anti-Map antibodies.

Sixty-three additional sera obtained directly from Dairy #2 were used to compare three Map ELISA tests: HerdChek®, ParaChek®, and pre-FUIDI #1. All testing was done at the Veterinary Diagnostic Laboratory at the University of Florida College of Veterinary Medicine.

The IDEXX and Prionic tests each identified six sera as attaining positive status. Each test failed to identify one positive that the other did not. The pre-FUIDI #1 test identified all seven positive sera. The pre-FUIDI #1 test identified 12 other sera as a positive Map titer, Another 6 sera had evidence of antigenic exposure to Map.

Current commercial Map ELISA test results certified by USDA should not be used to determine whether a given animal has ever been infected by Map.

Experiment # IIa: *Mycobacterium* Spectrum within Chronic Granulomatous Enteritis in Herbivores USDA made three key decisions in developing its National Johne's Diseases Control Program; 1) Map was the only cause of Johne's disease; 2) that the IS900 insertion sequence identified all pathogenic mycobacteria that cause Johne's disease; and 3) *Mycobacterium avium* subspecies *avium*, *Mycobacterium avium* complex mycobacteria, and *Mycobacterium hominissuis* were environmental nonpathogenic contaminants. The Map diagnostic tests conformed to the mandate for identification specificity.

The hypothesis embedded in IDI's second set of studies is that the current commercial Map ELISA tests based upon the IS900 insertion sequence prototype organism do not identify all mycobacteria that cause Johne's disease in herbivores The experimental design is a retrospective identification of a study population upon which is imposed parallel comparative testing. The study population was derived from histologically confirmed cases of Johne's disease in the files of the University of Florida College of Veterinary Medicine for which both fecal and sera still existed, Immunological confirmation of the causative agent was achieved using direct and nested primers based upon the IS1311 insertion sequence on the stored feces. Serum samples were equally divided and sent to the State of Florida Veterinary Diagnostic Laboratory in Live Oak, Fla. (ParaChek®) and to Veterinary Diagnostic Laboratory at the University of Florida College of Veterinary Medicine pre-FUIDI).

Of the nine diseased cows, the ParaChek® identified one as being positive and one as being suspicious. The pre-FUIDI #1 test identified six as have a diagnostic Map antibody titer.

Neither Map ELISA tests whose antigenic arrays are derived from an IS900 standard identified all nine diseased animals.

Experiment #IIb: Pathogenic *Mycobacterium* Spectrum within Chronic Granulomatous Enteritis in Herbivores The IS900 insertion sequence is deemed to be the definitive specific marker for *Mycobacterium avium* subspecies *paratuberculosis*. It is argued that the IS900 insertion sequence is a single vertical cut through a horizontal evolutionary process emanating from *Mycobacterium avium* subspecies *avium* or *Mycobacterium hominissuis* in which exist other polymorphic variants of these species that can cause Johne's disease in herbivores and omnivores (Frothingham R.: *Evolutionary bottlenecks in the agents of tuberculosis, leprosy, and paratuberculosis. Med. Hypothesis* 1999; 52:95-99). The veterinary literature documents that. In horses, pigs, and dogs, Ma and *Mycobacterium avium* complex (Mac) causative agents for the induction of Johne's disease.

The inventor developed Map identification primers (disclosed herein) based upon the IS1311 insertion sequence. These primers will identify *Mycobacterium avium* subspecies *avium* (Maa), selected *Mycobacterium avium* complex (Mac), and *Mycobacterium hominissuis*. USDA have deemed fecal isolates of Maa to be environmental contaminates and not a potentially pathogenic *mycobacterium*. The experimental design was a prospective comparative study analyzing to what extend IS1311 primers would identify a non-Map fecal isolate, not substantiated by fecal culture or real-time PCR using hspX.

Three hundred sixty-eight dairy cows within the Florida Johne's Disease Dairy Herd Demonstration Project constituted the study population. Fecal cultures and real time Map PCR testing were done at Animal Disease Diagnostic Laboratory, School of Veterinary Medicine, Purdue University using the Trek® Map Culture System and using Tetracore® Map Extraction and DNA test kit in accordance with the manufacturer's instructions.

The direct fecal nested Map PCR tests were done at University of Florida College of Veterinary Medicine using the FecaMap® system in accordance with the manufacturer's instructions. The FecaMap® direct primers recognize a 242 base pair sequence of Map IS1311 and its nested primers overlap and span a 104 base pair region within the insertion sequence. Both testing facilities independently forwarded tests results to USDA.

Three hundred sixty-eight fecal samples from the Florida Johne's Disease Dairy Herd Demonstration Project had been analyzed using fecal culture, real-time PCR and nested PCR for the detection of Map. Forty-one fecal specimens tested positive by the direct fecal nested Map PCR test (FecaMap®). In 34 of the cases, the corresponding real time PCR test for Map was also positive. *Mycobacterium* isolates were achieved by fecal culture in 21 of the 41 cases. In 20 of the 21 cases of culture recovery of a *mycobacterium*, Map was confirmed by IS900-based primers. In the remaining case, fecal culture demonstrated case heavy growth and the corresponding hspX real time PCR were both positive. The animal was culled for clinical reasons before the need to retest was identified. In the remaining 6 direct nested PCR tests, no evidence of *mycobacterium* growth was present. Seven fecal samples by identified real-time PCR were not substantiated by either culture or nested PCR. The fecal identification of a non-IS900 *mycobacterium* was 1.1%. The non-correlation of *mycobacterium* identified by IS1311 primers with results using real-time hspX PCR or culture in seven cases

TABLE 11

Analysis of dairy cows in the Florida Johne's Disease Prevention Dairy Herd Demonstration Project for prevalence of Map/Ma DNA in fecal samples as determined by the FecaMap ® direct nest fecal Map PCR test.

| # of fecal specimens | # culture positive/ # nested positive | # RT PCR positive/ nested positive | # non-Map positive cultures/RT & nested positive |
|---|---|---|---|
| 368 | 20/41 | 34/41 | 1/1 |

In contrast to the significance of the demonstration of a non-IS900 *mycobacterium* in milk or tissue, the identification by IS1311 based primers of a *mycobacterium*, not corroborated by real-time PCR or culture, must be considered speculative.

The nested Map PCR identified a non-IS900 *mycobacterium* whose test profile was that of being a heavy shedder in the Trek® culture system and of testing positive in the Tetracore® PCR system. These observations coupled with early culling makes it, more likely than not, that this animal had a significant *mycobacterium* infection. To what degree other non-IS900 potentially pathogenic mycobacteria have been dismissed as being environmental contaminants is undetermined.

Experiment # IIc: Pathogenic *Mycobacterium* Spectrum of Chronic Granulomatous Enteritis in Herbivores

*Mycobacterium* isolates from slaughter houses and other entities are periodically sent to USDA's diagnostic laboratory in Ames Iowa. IDI obtained from USDA its list of mycobacteria derived from any source from 2009-2010 and then refined the list to isolates obtained from cows Forty-three presumed *mycobacterium* isolates derived from cows were forward to Ames, Iowa for identification. The vast majority came from slaughter houses or diagnostic test facilities. Of the 43 isolates, only three were identified as Map. The remaining 41 isolates were: *Mycobacterium hominissuis*, 16, probable *Mycobacterium avium* complex 7, *Mycobacterium avium* subspecies *avium* 5, *Mycobacterium avium* subspecies *paratuberculosis* 3, and misc. 6. These mycobacteria contain the IS1311 insertion sequence.

Organism identification of mycobacteria from milk, white blood cells, or tissues using PCR primers based on the IS900 insertion sequence is inadequate.

Experiment # III; Comparison of IS900 and IS1311 in Identifying Map

A major premise in the development of IDI's diagnostic technology is that Map emerged through an evolutionary bottleneck and that between *M. avium* and Map exist a significant degree of genomic polymorphism among mycobacteria that can induce Johne's disease. Presuming the correctness of that assumption, the IS1311 should have greater representation in Map than its unique IS900 insertion sequence.

To test this hypothesis, direct and nested primers, based upon the IS900 and IS1311 insertion sequences, were tested in parallel in four USDA Map Laboratory Certification Tests. The test results are assessed as to their correctness by USDA which then notifies the submitting institution of the results. The sensitivity of the direct IS1311 and IS900 primers were 55.6% and 21.7% respectively; those for the nested IS1311 and IS900 primers were 85.15% and 74.6%.

Given that the IS1311 direct primers identify only 6-8 copies whereas the IS900 primers identify 14-18 copies, the most probable explanation for the IS1311 primers testing superiority is the sequences being identified has greater representation within the Map genome.

In summary, decisions to have Map ELISA test be indicative of the presence or absence of anti-Map antibodies masks the true prevalence of Map infection in animals and humans. The use of but IS900 based primers to identify pathogenic mycobacteria in milk or tissue is based upon flawed reasoning; Map is a cause of Johne's disease but not the cause of Johne's disease in animals.

REFERENCES

1. Millar D., Ford J., Sanderson J., Withey S., Tizard M., Doran T., Hermond-Taylor J: IS900 PCR to detect *Mycobacterium avium* subspecies *paratuberculosis* in retail supplies of whole pasteurized milk in England and Wales. *Appl. Environ. Microbiol.* 1996; 62:3446-52.
2. Grant I. R., Ball H. J., Rowe M. T.: incidence of *Mycobacterium paratuberculosis* in bulk raw and commercially pasteurized milk from approved dairy processing establishment in the United Kingdom. *Appl. Environ. Microbiol.* 2002; 68:2428-2435.
3. Clark D. L. Jr., Anderson J. L., Kozickowski J. J., Ellingson J. L. E.: Detection of *Mycobacterium avium* subspecies *paratuberculosis* in cheese curds purchased in Wisconsin and Minnesota. *Molecular Cell. Probes* 2006; 20:197-202.
4. Hruska K., Kralik P., Pavlik I.: *Mycobacterium avium* subspecies *paratuberculosis* in powder milk: F57 competitive real time PCR. *Veterinarni Medicina* 2011; 56:226-230.
5. Ikonomoplus J., Pavilk I., Bartos M., et al: Detection of in retail cheese from Greece and Czech Republic. *Appl. Environ Microbiol.* 2005; 71:8935-9036.
6. Pinedo P. J., Williams J. E., Monif, G. R. G. et al: *Mycobacterium avium* subspecies *paratuberculosis* shedding into milk: association of ELISA seroreactivity with DNA detection in milk. *Intern. J. Appl. Res. Vet. Med.* 2008; 6:137-144.
7. Wisziewska-Laszcych A., Szteyn L., Smolinska A." Analysis of correlation between the occurrence of anti-Map antibodies in blood serum and the presence of DNA-Map in milk. *Polish J. Vet. Sci.* 2009; 233:379-383.
8. Rubery E.: A review of the evidence for a link between *Mycobacterium paratuberculosis* (MAP) and Crohn's disease (CD) in humans: A report for the Food Standard Agency, Jun. 1 2001.
8. Nacy C. Buckley M.: *Mycobacterium avium paratuberculosis*: Infrequent human pathogen or public health threat? Report from the American Academy of Microbiology 2008. p. 1-37.
9. Bull T. L., McMinn E. J., Sidi-Boumedine K. et al.; Detection and verification of *Mycobacterium avium* subspecies *paratuberculosis* in fresh ileocolonic mucosal biopsies from individuals with and without Crohn's disease. *J. Clin. Microbiol.* 2003; 41:2915-2923.
10. Scanu A. M., Bull T. J., Cannas C. et al.: *Mycobacterium avium* subspecies *paratuberculosis* infection of irritable bowel syndrome and comparison with Crohn's disease and Johne's disease: common neural and immune pathogenicities. *J. Clin. Microbiol.*
11. Naser S. A., Schwartz D., Shafran I.: Isolation of *Mycobacterium avium* subspecies *paratuberculosis* (MAP) from breast milk of patients with Crohn's disease. *Am. J. Gastroenterol* 2000; 95:1094-1095.
12. Naser S. A., Ghobrial G., Romero C., Valentine J. F.: Culture of *Mycobacterium avium* subspecies *paratuberculosis* (MAP) from the blood of Crohn's disease patients. *Lancet* 2004; 364:1039-1044.
13. Sechi L. A., Scanu A. M., Molicotti P., Molicotti P., Cannes S., Mura M., Dettori G., Fadda G., Zanetti S.: Detection and isolation of *Mycobacterium avium* subspecies *paratuberculosis* from intestinal biopsies of patients with and without Crohn's disease in Sardinia. *Am. J Gastroenteriol.* 2005; 100:1529-1534.
14. Autschback F., Eisold S., Hinz U.: High prevalence of *Mycobacterium avium* subspecies *paratuberculosis* IS900 DNA in gut tissue from individuals with Crohn's disease. *Gut* 2005; 54:944-949.
15. Ghadiali A. H., Strother M., Naser S. A. et al.: *Mycobacterium avium* subsp. *paratuberculosis* strains isolated from Crohn's disease patients and animal species exhibit similar polymorphic locus patterns. *J. Clin. Microbiol.* 2004; 42:5345-5348.
16. Naser S. A., Collins M. T., Crawford J. T., Valentine J. F.: Culture of *Mycobacterium avium* subspecies *paratuberculosis* (MAP) from the blood of patients with Crohn's disease: A follow-up blind multi-center investigation. *The Open Inflam.* 1 2009; 2:22-23.
17. Harris N. B., Barletta R. G.: 2001 *Mycobacterium avium* subsp. *paratuberculosis* in veterinary medicine. *Clin. Microbiol. Rev.* 14:489-512;
18. Turenne C. Y., Wallace R., Behr M. A.: 2007. *Mycobacterium avium* in the postgenomic era. *Clin. Microbiol. Review* 20:205-229.
19. Frothingham R.: 1999. Evolutionary bottlenecks in the agents of tuberculosis, leprosy and *paratuberculosis*. *Med. Hypothesis* 52:95-99.
20. Harris N. B., Bartlett R. G.: 2001. *Mycobacterium avium* subsp. *paratuberculosis* in *Veterinary Medicine. Clin. Microbiol. Reviews* 14:489-512.
21. Thotel M. F. Krichevisky M., Levy-Frebault V. V.: 1990. Numerical taxonomy of mycobactin-dependent *mycobacterium* amended description of *Mycobacterium avium* description of *Mycobacterium avium* subsp. *avium*, subsp. *nova*, *Mycobacterium avium* subsp. *paratuberculosis* subsp. *nova*, and *Mycobacterium avium* subsp. *salvaticum* subsp. *nova*. *Int. J. Syst. Bacteriol.* 40:254-260.
22. Cousins D. V., Whittington R., Marsh I. Masters R. J., Evans R. J., Kluver P.: 1999. Mycobacteria distinct from *Mycobacterium avium* subspecies *paratuberculosis* isolated from feces of ruminants possess IS900-like sequences detectable by polymerase chain reaction: implications for diagnosis. *Mol. Cell. Probes* 14:431-442.
23. Bolski G, Johansson K-F: 2002. An IS900-like sequence found in a *Mycobacterium* sp. other than *Mycobacterium avium* subspecies *paratuberculosis*. *FEMS Microbiol. Lett.* 209:267-271.
24. England S., Bolske G., Johansson: 2002. An IS900-like sequence found in *Mycobacterium* sp. other than *Mycobacterium avium* subspecies *paratuberculosis*. *FEMS Microbiol. Lett.* 34:734-737.
25. Whittington R., Marsh I., Chow E., Cousins D.: 1998. Polymorphism in IS1311, an insertion sequence common to *Mycobacterium avium* subsp. *paratuberculosis*, can be used to distinguish between and within these species. *Mol. Cell. Probes* 12:349-358.
26. Darcel C. Logen-Handsame B.: ELISA testing for antibodies for *Mycobacterium paratuberculosis*. *Can. Vet. J.* 1998; 39:335-336.
27. Nielsen S. S., et al., "Time to occurrence of a decline in milk production in cows with various *paratuberculosis* antibody profiles", *J. Diary Sci.* 2009; 92; 149-155).

What is claimed is:

1. A method for herd management that stratifies the risk of bulk tank milk lots derived from diagnostic-tested subgroups potentially containing DNA from pathogenic mycobacterium comprising *Mycobacterium avium* subspecies *paratuberculosis* (Map), said method comprising:

(a) determining the level of a Map-specific antibodies in blood samples from individual milk-producing animals, wherein said determining comprises:

(i) conducting a first test that identifies if the animals have had antigenic exposure to Map, wherein the first test is an immunoassay comprising contacting a plasma or a serum from an animal with FUIDI antigen deposited as ATCC PTA-11837 and detecting the binding of antibodies to said FUIDI antigen; and (ii) conducting a second test that assesses active Map replication in the animals, wherein the second is an immunoassay comprising contacting a plasma or serum from said animals with Map lipoarabinomannan polysaccharides (LAM) and/or membrane lipoproteins and detecting the binding of antibodies to said Map LAM and/or membrane lipoproteins, and wherein the presence of antibodies against Map LAM and/or membrane lipoproteins indicates active Map replication;
(b) categorizing the animals into a plurality of risk categories based on the results of the first and second tests; the risk categories comprising:
(i) a first category of animals having no detectable Map-specific antibodies in the first and second tests;
(ii) a second category of animals having a low level of Map-specific antibodies in the first test and no detectable Map-specific antibodies in the second test;
(iii) a third category of animals having an intermediate level of Map-specific antibodies in the first test and no detectable Map-specific antibodies in the second test;
(iv) a fourth category of animals having a high level of Map-specific antibodies in the first test and no detectable Map-specific antibodies in the second test; and
(v) a fifth category of animals having a low, intermediate. or high level of Map-specific antibodies in the first test, and low or intermediate level of Map-specific antibodies in the second test;
and
(c) detecting the presence of Map in a bulk milk sample obtained from a volume of milk from a plurality of animals in each category by determining the presence of a nucleic acid encoding SEQ ID NO: 6 in the bulk milk sample.

2. The method of claim 1, wherein the first test and/or the second test is an enzyme-linked immunosorbent assay (ELISA).

3. The method of claim 1, wherein said categorizing of (b) further comprises separating the animals of each category from animals of any other category.

4. The method of claim 1, further comprising, after determining the presence of the nucleic acid encoding SEQ ID NO: 6 in a bulk milk sample from the first, second, or third risk category of animals in accordance with (c), wherein the nucleic acid encoding SEQ ID NO: 6 is determined to be absent in the bulk milk sample of (c), repeating (a) and (c) annually to reassess the risk category.

5. The method of claim 1, further comprising, after determining the presence of the nucleic acid encoding SEQ ID NO: 6 in a bulk milk sample from the first, second, third, or fourth risk category of animals in accordance with (c), wherein the nucleic acid encoding SEQ ID NO: 6 is determined to be present in the bulk milk sample (c), repeating (c) one or more times to exclude incidental contamination.

6. The method of claim 5, further comprising, after repeating (c) one or more times to exclude incidental contamination and excluding incidental contamination, determining the presence of the nucleic acid encoding SEQ ID NO: 6 in a milk sample of each individual animal in the risk category.

7. The method of claim 6, wherein the nucleic acid encoding SEQ ID NO: 6 is determined to be present in the milk sample of at least one individual animal, the method further comprising removing the at least one individual animal from milk production.

8. The method of claim 6, wherein the nucleic acid encoding SEQ ID NO: 6 is determined to be absent in the milk sample of at least one individual animal, the method further comprising repeating (a) and (c) annually to reassess the risk category of the individual animal.

9. The method of claim 1, further comprising, after determining the presence of the nucleic acid encoding SEQ ID NO: 6 in a bulk milk sample from the third risk category of animals in accordance with (c) and determining the nucleic acid encoding SEQ ID NO: 6 to be absent in the bulk milk sample, repeating (a) and determine presence of the nucleic acid encoding SEQ ID NO: 6 in milk of each individual animal prior to calving and two months after calving.

10. The method of claim 1, further comprising, after determining the presence of the nucleic acid encoding SEQ ID NO: 6 in a bulk milk sample from the first or second risk category of animals in accordance with (c), wherein the nucleic acid encoding SEQ ID NO: 6 is determined to be present in the bulk milk sample of (c), repeating (c) one or more times to exclude incidental contamination and when the nucleic acid encoding SEQ ID NO: 6 is determined to be present in repeated (c) such that incidental contamination is excluded, determining the presence of the nucleic acid encoding SEQ ID NO: 6 in a milk sample of each individual animal in the risk category, and if absent, repeating (a) and (c) annually to reassess risk category.

11. The method of claim 1, further comprising, after determining the presence of the nucleic acid encoding SEQ ID NO: 6 in a bulk milk sample from the third or fourth risk category of animals in accordance with (c), wherein the nucleic acid encoding SEQ ID NO: 6 is determined to be present in the bulk milk sample of (c), repeating (c) one or more times to exclude incidental contamination and when the nucleic acid encoding SEQ ID NO: 6 is determined to be present in repeated (c) such that incidental contamination is excluded, determining the presence of the nucleic acid encoding SEQ ID NO: 6 in a milk sample of each individual animal in the risk category, and if absent, repeating (a) and determining the presence of the nucleic acid encoding SEQ ID NO: 6 of each individual animal prior to calving and two months after calving.

12. The method of claim 1, further comprising, after determining the presence of the nucleic acid encoding SEQ ID NO: 6 in a bulk milk sample from the fourth risk category of animals in accordance with (c), wherein the nucleic acid encoding SEQ ID NO: 6 is determined to be absent in the bulk milk sample of (c), repeating (a) and determining the presence of the nucleic acid encoding SEQ ID NO: 6 in milk of each individual animal prior to calving and two months after calving.

13. The method of claim 1, further comprising, after determining the presence of the nucleic acid encoding SEQ ID NO: 6 in the bulk milk sample from the fifth risk category of animals in accordance with (c), wherein the nucleic acid encoding SEQ ID NO: 6 is determined to be absent in the bulk milk sample of (c), determining the presence of the nucleic acid encoding SEQ ID NO: 6 in bulk sample of the fifth risk category of animals every two months.

14. The method of claim 13, further comprising, if the level of Map-specific antibody in the second test increases for an animal or animals, increasing the frequency of determining the presence of the nucleic acid encoding SEQ ID NO: 6 in the milk sample of the individual animal or animals to monthly.

15. The method of claim 14, further comprising removing the animal or animals from milk production if the nucleic acid encoding SEQ ID NO: 6 is determined to be present in milk of the individual animal or animals.

16. The method of claim 1, further comprising, after determining the presence of the nucleic acid encoding SEQ ID NO: 6 in a bulk milk sample from the fifth risk category of animals in accordance with (c), wherein the nucleic acid encoding SEQ ID NO: 6 is determined to be present in the bulk milk sample of (c), repeating (a) and determining the presence of the nucleic acid encoding SEQ ID NO: 6 in milk of each animal of the fifth risk category.

17. The method of claim 16, further comprising removing the animal or animals from milk production if the nucleic acid encoding SEQ ID NO: 6 is determined to be present in milk of the individual animal or animals.

18. The method of claim 1, wherein the animals are selected from among cows, sheep, goats, llamas, buffalo, camels, and yaks.

19. The method of claim 1, wherein the presence of a nucleic acid encoding SEQ ID NO: 6 is determined by PCR amplification of said nucleic acid.

20. The method according to claim 1, wherein the nucleic acid encoding SEQ ID NO: 6 comprises SEQ ID NO: 214.

* * * * *

UNITED STATES PATENT AND TRADEMARK OFFICE
CERTIFICATE OF CORRECTION

| | | |
|---|---|---|
| PATENT NO. | : 9,128,098 B2 | Page 1 of 1 |
| APPLICATION NO. | : 13/690530 | |
| DATED | : September 8, 2015 | |
| INVENTOR(S) | : Gilles R. G. Monif | |

It is certified that error appears in the above-identified patent and that said Letters Patent is hereby corrected as shown below:

In the Claims

Column 163,
Lines 18-19, "intermediate. or" should read --intermediate, or--.

Column 164,
Line 47, "in bulk" should read --in a bulk--.

Signed and Sealed this
Seventh Day of June, 2016

Michelle K. Lee
*Director of the United States Patent and Trademark Office*

SEQUENCE LISTING

<160> NUMBER OF SEQ ID NOS: 214

<210> SEQ ID NO 1
<211> LENGTH: 21
<212> TYPE: DNA
<213> ORGANISM: Artificial sequence
<220> FEATURE:
<223> OTHER INFORMATION: PCR primer

<400> SEQUENCE: 1
cgatttatca ggcactcatc g                                          21

<210> SEQ ID NO 2
<211> LENGTH: 20
<212> TYPE: DNA
<213> ORGANISM: Artificial sequence
<220> FEATURE:
<223> OTHER INFORMATION: PCR primer

<400> SEQUENCE: 2
caaataggcc tccatcacca                                            20

<210> SEQ ID NO 3
<211> LENGTH: 18
<212> TYPE: DNA
<213> ORGANISM: Artificial sequence
<220> FEATURE:
<223> OTHER INFORMATION: PCR primer

<400> SEQUENCE: 3
atgaacggag cgcatcac                                              18

<210> SEQ ID NO 4
<211> LENGTH: 18
<212> TYPE: DNA
<213> ORGANISM: Artificial sequence
<220> FEATURE:
<223> OTHER INFORMATION: PCR primer

<400> SEQUENCE: 4
cgaccgaagc ttgggaat                                              18

<210> SEQ ID NO 5
<211> LENGTH: 1317
<212> TYPE: DNA
<213> ORGANISM: Mycobacterium avium
<220> FEATURE:
<221> NAME/KEY: CDS
<222> LOCATION: (57)..(1292)

<400> SEQUENCE: 5

```
tcgcgtgagg ctctgtggtg aaacgaccaa ggatcactac cgagaggaac atcgcg atg      59
                                                              Met
                                                              1 gcc ctg gat cag tct gcc ttg ctg gag gtg ctg gac gca tta cgc aat        107
Ala Leu Asp Gln Ser Ala Leu Leu Glu Val Leu Asp Ala Leu Arg Asn
            5                  10                  15 gcc gat gcc gct gat cgg atc aag cag gcc gcc gag acg att tat cag        155
Ala Asp Ala Ala Asp Arg Ile Lys Gln Ala Ala Glu Thr Ile Tyr Gln
         20                  25                  30 gca ctc atc gat gcg gag ctg acg gcg gtg atc ggc gcc ggt ccg cat        203
Ala Leu Ile Asp Ala Glu Leu Thr Ala Val Ile Gly Ala Gly Pro His
     35                  40                  45 gaa cgg agc gca tca cga acc aac cag cgc aat ggg tct cgg ccg cgc        251
Glu Arg Ser Ala Ser Arg Thr Asn Gln Arg Asn Gly Ser Arg Pro Arg
```

```
           50                  55                  60                  65
aca ctg tcg acg atc gct ggc gat ttg gag ttg cgg att ccc aag ctt        299
Thr Leu Ser Thr Ile Ala Gly Asp Leu Glu Leu Arg Ile Pro Lys Leu
                    70                  75                  80 cgg tcg ggc tcg ttc ttc ccg gcg ctg ctg gag cgg cgc cgc cgg gtc        347
Arg Ser Gly Ser Phe Phe Pro Ala Leu Leu Glu Arg Arg Arg Arg Val
                85                  90                  95 gat cag tgc ttg ttc gcg gtg gtg atg gag gcc tat ttg cac ggc acc        395
Asp Gln Cys Leu Phe Ala Val Val Met Glu Ala Tyr Leu His Gly Thr
            100                 105                 110 tcc acc cgc aaa gtc gac gat ttg gtt aaa gcc ctc ggc gcg gac gcc        443
Ser Thr Arg Lys Val Asp Asp Leu Val Lys Ala Leu Gly Ala Asp Ala
115                 120                 125 ggc atc tcc aaa agc gag gtc tcc cgg att tgc gcc gat ctg gac acc        491
Gly Ile Ser Lys Ser Glu Val Ser Arg Ile Cys Ala Asp Leu Asp Thr
130                 135                 140                 145 gag gta ggc gcc ttt cgg gac cgg cct cta tcc gag cag cac ttc ccg        539
Glu Val Gly Ala Phe Arg Asp Arg Pro Leu Ser Glu Gln His Phe Pro
                150                 155                 160 tat gtg ttc ctc gac gcc act tac tgc aag gct cgg gtc aac cat cgg        587
Tyr Val Phe Leu Asp Ala Thr Tyr Cys Lys Ala Arg Val Asn His Arg
            165                 170                 175 gtg gtc tcc caa gcg gtc gtc atc gcc acc ggt gtc gcg gtt gac gga        635
Val Val Ser Gln Ala Val Val Ile Ala Thr Gly Val Ala Val Asp Gly
        180                 185                 190 cgc cgt gaa gtg ctc ggc ttc gac gtc ggt gac tcc gag gac ggc gcg        683
Arg Arg Glu Val Leu Gly Phe Asp Val Gly Asp Ser Glu Asp Gly Ala
    195                 200                 205 ttt tgg acg gcg ttt ctg cgc tca ctg aaa acc cgc ggc ctg tcc ggg        731
Phe Trp Thr Ala Phe Leu Arg Ser Leu Lys Thr Arg Gly Leu Ser Gly
210                 215                 220                 225 gtg cag ctg gtg atc tct gat gcc cac acc ggg ttg cgc agc gcc atc        779
Val Gln Leu Val Ile Ser Asp Ala His Thr Gly Leu Arg Ser Ala Ile
                230                 235                 240 gag gcc atc ctc atc ggc gca tct tgg caa cga tgc cgg gtg cac ttc        827
Glu Ala Ile Leu Ile Gly Ala Ser Trp Gln Arg Cys Arg Val His Phe
            245                 250                 255 ctg cgc aac gtg ctc gcc cag gtg ccc aag gga tca gcc gag atg gtc        875
Leu Arg Asn Val Leu Ala Gln Val Pro Lys Gly Ser Ala Glu Met Val
        260                 265                 270 gcc gca gcg atc cgc acc atc ttc gcc caa ccc gac gcc gaa cat gtg        923
Ala Ala Ala Ile Arg Thr Ile Phe Ala Gln Pro Asp Ala Glu His Val
    275                 280                 285 cga gag caa ctc gac acc atc gcc ggc atg ctc ggc cgc caa ctg ccc        971
Arg Glu Gln Leu Asp Thr Ile Ala Gly Met Leu Gly Arg Gln Leu Pro
290                 295                 300                 305 aag gtc gaa acg atg ctg cgc gag gcc gcc gac gac atc acc gca ttc        1019
Lys Val Glu Thr Met Leu Arg Glu Ala Ala Asp Asp Ile Thr Ala Phe
                310                 315                 320 gcc gat ttc cct gtc ctg cac tgg aaa aag atc tgg agc acc aac ccc        1067
Ala Asp Phe Pro Val Leu His Trp Lys Lys Ile Trp Ser Thr Asn Pro
            325                 330                 335 ctc gaa cga ctc aac aag gag atc aaa cgc cgc acc gac gtc gtc ggc        1115
Leu Glu Arg Leu Asn Lys Glu Ile Lys Arg Arg Thr Asp Val Val Gly
        340                 345                 350 gtc ttc ccc aac ccc gcc gcg ctg cta cgg ctg gcc ggc tcc gtt ctc        1163
Val Phe Pro Asn Pro Ala Ala Leu Leu Arg Leu Ala Gly Ser Val Leu
    355                 360                 365 gtc gaa gcc cac gac gaa tgg caa gtc gcc gaa aag cgc tat ctc tcc        1211
```

```
Val Glu Ala His Asp Glu Trp Gln Val Ala Glu Lys Arg Tyr Leu Ser
370                 375                 380                 385 gag acc acc ctg gcc cta tta cat ccc cgc tcc gat tca gcc gac caa    1259
Glu Thr Thr Leu Ala Leu Leu His Pro Arg Ser Asp Ser Ala Asp Gln
                    390                 395                 400 tcc gtt gcc gtc ccc gcc gcc atc acg gca tag tggaaactcg cagagcctca  1312
Ser Val Ala Val Pro Ala Ala Ile Thr Ala
                405                 410 ggcga                                                              1317

<210> SEQ ID NO 6
<211> LENGTH: 411
<212> TYPE: PRT
<213> ORGANISM: Mycobacterium avium

<400> SEQUENCE: 6

Met Ala Leu Asp Gln Ser Ala Leu Leu Glu Val Leu Asp Ala Leu Arg
1               5                   10                  15

Asn Ala Asp Ala Ala Asp Arg Ile Lys Gln Ala Ala Glu Thr Ile Tyr
                20                  25                  30

Gln Ala Leu Ile Asp Ala Glu Leu Thr Ala Val Ile Gly Ala Gly Pro
            35                  40                  45

His Glu Arg Ser Ala Ser Arg Thr Asn Gln Arg Asn Gly Ser Arg Pro
        50                  55                  60

Arg Thr Leu Ser Thr Ile Ala Gly Asp Leu Glu Leu Arg Ile Pro Lys
65                  70                  75                  80

Leu Arg Ser Gly Ser Phe Phe Pro Ala Leu Leu Glu Arg Arg Arg
                    85                  90                  95

Val Asp Gln Cys Leu Phe Ala Val Val Met Glu Ala Tyr Leu His Gly
                100                 105                 110

Thr Ser Thr Arg Lys Val Asp Asp Leu Val Lys Ala Leu Gly Ala Asp
            115                 120                 125

Ala Gly Ile Ser Lys Ser Glu Val Ser Arg Ile Cys Ala Asp Leu Asp
        130                 135                 140

Thr Glu Val Gly Ala Phe Arg Asp Arg Pro Leu Ser Glu Gln His Phe
145                 150                 155                 160

Pro Tyr Val Phe Leu Asp Ala Thr Tyr Cys Lys Ala Arg Val Asn His
                165                 170                 175

Arg Val Val Ser Gln Ala Val Val Ile Ala Thr Gly Val Ala Val Asp
                180                 185                 190

Gly Arg Arg Glu Val Leu Gly Phe Asp Val Gly Asp Ser Glu Asp Gly
            195                 200                 205

Ala Phe Trp Thr Ala Phe Leu Arg Ser Leu Lys Thr Arg Gly Leu Ser
        210                 215                 220

Gly Val Gln Leu Val Ile Ser Asp Ala His Thr Gly Leu Arg Ser Ala
225                 230                 235                 240

Ile Glu Ala Ile Leu Ile Gly Ala Ser Trp Gln Arg Cys Arg Val His
                245                 250                 255

Phe Leu Arg Asn Val Leu Ala Gln Val Pro Lys Gly Ser Ala Glu Met
                260                 265                 270

Val Ala Ala Ala Ile Arg Thr Ile Phe Ala Gln Pro Asp Ala Glu His
            275                 280                 285

Val Arg Glu Gln Leu Asp Thr Ile Ala Gly Met Leu Gly Arg Gln Leu
        290                 295                 300

Pro Lys Val Glu Thr Met Leu Arg Glu Ala Ala Asp Asp Ile Thr Ala
```

```
                305                 310                 315                 320
        Phe Ala Asp Phe Pro Val Leu His Trp Lys Lys Ile Trp Ser Thr Asn
                        325                 330                 335

Pro Leu Glu Arg Leu Asn Lys Glu Ile Lys Arg Arg Thr Asp Val Val
                        340                 345                 350

Gly Val Phe Pro Asn Pro Ala Ala Leu Leu Arg Leu Ala Gly Ser Val
                        355                 360                 365

Leu Val Glu Ala His Asp Glu Trp Gln Val Ala Glu Lys Arg Tyr Leu
                370                 375                 380

Ser Glu Thr Thr Leu Ala Leu Leu His Pro Arg Ser Asp Ser Ala Asp
        385                 390                 395                 400

Gln Ser Val Ala Val Pro Ala Ala Ile Thr Ala
                        405                 410

<210> SEQ ID NO 7
<211> LENGTH: 2263
<212> TYPE: DNA
<213> ORGANISM: Mycobacterium avium
<220> FEATURE:
<221> NAME/KEY: misc_feature
<222> LOCATION: (1)..(2263)
<223> OTHER INFORMATION: Mycobacterium avium subspecies paratuberculosis
      insertion sequence ISMav2

<400> SEQUENCE: 7
gagctcggcc agcacttcat ccgggtgaat tccgtgcacc ccaccaacgt gaacacaccg        60
atgttcatga acgaggggac gatgaggctg ttccggccgg acctgaagaa ccccggcccg       120
gacgacctga aggtcgccgc gcagttcatg catgtgctgc cggtcggctg ggtggagccg       180
gtggacatca gcaacgccgt gctgttcctg gcctccgacg aatcgcgtta catcacaggt       240
cttccggtca ccctcgacgc cggcagcatg ctcaagtagc cgcgccggca tctcgctcac       300
cggcggtgag gatcatcccg gtggccaggg gcgggatcga accgccgacc ttccgctttt       360
caggcggacg ctcgtaccga ctgagctacc tggccggaag gcagcgagtg gctcgccgcg       420
ctggcgaccc tgacgggact cgaacccgcg acctccgccg tgacaggcg gcgcgctaac        480 caactgcgcc acagggcctt gctgctgctc gcgtcgccg cgttgcgtac ccctacggg         540 attcgaaccc gcgctaccgc cttgaaaggg cggcgtccta ggccgctaga cgaaggggc        600 cagaaccgaa tctctccggg gtactcgcaa cgtggtttcg ttgggagcca cgtcagctta       660
ggtcaccgtg ggcccaatcc tcaaacgagc ccggttttgg gtccaagtat cctgaaactc       720
cgcggcccct atagctcagt ggtagagct acggactttt aatccgcagg tcctaggttc        780
gagtcctagt gggggcacca gatgtatgta tgacgtcggc tgatgtgtga cgttttgtct       840
tcggttgatg tgtgacggtg tttcggttga tgcgtgacag ttgtttcggc tgatcggtga       900
cactccctag atgagggagt taagtgtggc tgagcagcgg tatcaggccg tgatggcggt       960
aatcagtgac gggttgtcgg tgtcgcaggc gcagagaag ttcggggtgg cgcgtcagac       1020
gctgcaccga tggctggccc ggtatgaagc gcgggcctg aagggctgg tggatcggtc       1080 gcatcggccg gtgagttgtc cgcatcagat gctggcggta gtggaggcgg cggtgttgga      1140
gttgcgccgc tcgcggccct attggggcc gggcggttg tgttcgagt tggccaagcg         1200 aggtgtccat ccggtgccgt cggagtcgcc ggtgtatcga gcgctggtgc gggccggtct      1260
gatcgacccc gcgatgcgag atcgacggtc gcgcaaatgg aagcgctggg agcgcggggc      1320
gccgatggag ttgtggcagc tcgacatcgt cggcgggttc ccgctggccg atgggaccag      1380
```

-continued

```
cgccaaagcc ctgaccggca tcgatgatca ttcccggatg tgtgtgtgcg ccaagctgat    1440
ggcccgtgag cgcacccgcg cggtctgcga cggattacgg gcggcgctgg ccgcttacgg    1500
ggtgcctgag cagatcttga ccgataacgg caaggtgttc accgagcggt tttgtcatcc    1560
accggtcgag gtgctctttg atgcgatctg ccgcgagcac ggcatcgaac atctgttgac    1620
ccagccgcgc agcccgacca cgaccggcaa aatcgagcag tttcaccgca gtctgcgcgc    1680
tgagttcctt agcggccgtg agcctttcac caacctcaag gtcgctcagc aggcgctcga    1740
tgagtgggtc gaggactaca acaccacccg gccgcaccaa gccctaaaga tgatcacacc    1800
ggctcaacgg tttcacgccg gtgcgccggc atcaccaccg tcgaactcgt gtgcccgaca    1860
cgtcgaccgc agtggtgatg actgggtgag tcggcgggtg tgctccaacg gcatcgtgtg    1920
cgtgtcctgg cagcaggtct gtatcggcgc ccactatgcc ggcgcccgct gcgatgtcca    1980
cgtcgatggg gacctgctga ggttttgggt cggcgacaat ctggtcaaaa ccgccgcgcg    2040
caccagccgc ggcgaggtac gaaacaaaca ggccctgcgc accaacgcac cggcctaaaa    2100
cacaacccag agtgtcaccg atcaaccgac atagaaatgt caccgagcaa ccgaccctga    2160 acagggcac cagagagcag ccccgcccgc tcaggtggtc gacgatgtgg ctgcgctcgc     2220
cgtggtagac caggtcattg aaatcgacct cgaacccgag ctc                      2263
```

```
<210> SEQ ID NO 8
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1

<400> SEQUENCE: 8
gtcattcaga atcgctgcaa                                                  20

<210> SEQ ID NO 9
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F2

<400> SEQUENCE: 9
tggcgtcagc tattggtgta                                                  20

<210> SEQ ID NO 10
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F1F2

<400> SEQUENCE: 10
aactcgaaca cacctgggac                                                  20

<210> SEQ ID NO 11
<211> LENGTH: 20
<212> TYPE: DNA
<213> ORGANISM: Mycobacterium avium
<220> FEATURE:
<221> NAME/KEY: misc_feature
```

<222> LOCATION: (1)..(20)
<223> OTHER INFORMATION: Primer F3

<400> SEQUENCE: 11
tcctctcctt cgtcaccaac                                                 20

<210> SEQ ID NO 12
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F4

<400> SEQUENCE: 12
atgaaatggg cgtctaccag                                                 20

<210> SEQ ID NO 13
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F3F4

<400> SEQUENCE: 13
gtcattcaga atcgctgcaa                                                 20

<210> SEQ ID NO 14
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F5

<400> SEQUENCE: 14
gtcattcaga atcgctgcaa                                                 20

<210> SEQ ID NO 15
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F6

<400> SEQUENCE: 15
cgtcagctat tggtgtaccg                                                 20

<210> SEQ ID NO 16
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F5F6

<400> SEQUENCE: 16
aactcgaaca cacctgggac                                                 20

<210> SEQ ID NO 17

```
<210> SEQ ID NO 17
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F7

<400> SEQUENCE: 17
cattcagaat cgctgcaatc                                              20

<210> SEQ ID NO 18
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F8

<400> SEQUENCE: 18
tggcgtcagc tattggtgta                                              20

<210> SEQ ID NO 19
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F7F8

<400> SEQUENCE: 19
aactcgaaca cacctgggac                                              20

<210> SEQ ID NO 20
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F9

<400> SEQUENCE: 20
agaatcgctg caatctcagg                                              20

<210> SEQ ID NO 21
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F10

<400> SEQUENCE: 21
tggcgtcagc tattggtgta                                              20

<210> SEQ ID NO 22
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F9F10

<400> SEQUENCE: 22
```
aactcgaaca cacctgggac                                          20

<210> SEQ ID NO 23
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M1

<400> SEQUENCE: 23
cgaatcgcgt tacatcacag                                          20

<210> SEQ ID NO 24
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M2

<400> SEQUENCE: 24
gaaaccacgt tgcgagtacc                                          20

<210> SEQ ID NO 25
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M1M2

<400> SEQUENCE: 25
taccgactga gctacctggc                                          20

<210> SEQ ID NO 26
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M3

<400> SEQUENCE: 26
atcacaggtc ttccggtcac                                          20

<210> SEQ ID NO 27
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M4

<400> SEQUENCE: 27
gaaaccacgt tgcgagtacc                                          20

<210> SEQ ID NO 28
<211> LENGTH: 20
<212> TYPE: DNA
<213> ORGANISM: Mycobacterium avium
<220> FEATURE:

```
<221> NAME/KEY: misc_feature
<222> LOCATION: (1)..(20)
<223> OTHER INFORMATION: Probe M3M4

<400> SEQUENCE: 28
taccgactga gctacctggc                                                   20

<210> SEQ ID NO 29
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M5

<400> SEQUENCE: 29
gacgaatcgc gttacatcac                                                   20

<210> SEQ ID NO 30
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M6

<400> SEQUENCE: 30
gaaaccacgt tgcgagtacc                                                   20

<210> SEQ ID NO 31
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M5M6

<400> SEQUENCE: 31
taccgactga gctacctggc                                                   20

<210> SEQ ID NO 32
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M7

<400> SEQUENCE: 32
tcgcgttaca tcacaggtct                                                   20

<210> SEQ ID NO 33
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M8

<400> SEQUENCE: 33
gaaaccacgt tgcgagtacc                                                   20
```

```
<210> SEQ ID NO 34
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M7M8

<400> SEQUENCE: 34
taccgactga gctacctggc                                              20

<210> SEQ ID NO 35
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M9

<400> SEQUENCE: 35
gaatcgcgtt acatcacagg                                              20

<210> SEQ ID NO 36
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer M10

<400> SEQUENCE: 36
gaaaccacgt tgcgagtacc                                              20

<210> SEQ ID NO 37
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M9M10

<400> SEQUENCE: 37
taccgactga gctacctggc                                              20

<210> SEQ ID NO 38
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1F2N1

<400> SEQUENCE: 38
gtcattcaga atcgctgcaa                                              20

<210> SEQ ID NO 39
<211> LENGTH: 21
<212> TYPE: DNA
<213> ORGANISM: Mycobacterium avium
<220> FEATURE:
<221> NAME/KEY: misc_feature
<222> LOCATION: (1)..(21)
<223> OTHER INFORMATION: Primer F1F2N2
```

<400> SEQUENCE: 39
cgtggtctct gagtttgggt a                                    21

<210> SEQ ID NO 40
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F1F2N1F1F2N2

<400> SEQUENCE: 40
ctggtagacg cccatttcat                                      20

<210> SEQ ID NO 41
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1F2N3

<400> SEQUENCE: 41
gtcattcaga atcgctgcaa                                      20

<210> SEQ ID NO 42
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1F2N4

<400> SEQUENCE: 42
tatcgatgaa atgggcgtct                                      20

<210> SEQ ID NO 43
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F1F2N3F1F2N4

<400> SEQUENCE: 43
cagctccaga tcgtcattca                                      20

<210> SEQ ID NO 44
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1F2N5

<400> SEQUENCE: 44
gtcattcaga atcgctgcaa                                      20

<210> SEQ ID NO 45
<211> LENGTH: 21
<212> TYPE: DNA
<213> ORGANISM: Mycobacterium avium

```
<220> FEATURE:
<221> NAME/KEY: misc_feature
<222> LOCATION: (1)..(21)
<223> OTHER INFORMATION: Primer F1F2N6

<400> SEQUENCE: 45
ccactcgtgg tctctgagtt t                                              21

<210> SEQ ID NO 46
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F1F2N5F1F2N6

<400> SEQUENCE: 46
ctggtagacg cccatttcat                                                20

<210> SEQ ID NO 47
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1F2N7

<400> SEQUENCE: 47
gtcattcaga atcgctgcaa                                                20

<210> SEQ ID NO 48
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1F2N8

<400> SEQUENCE: 48
atcgatgaaa tgggcgtcta                                                20

<210> SEQ ID NO 49
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F1F2N7F1F2N8

<400> SEQUENCE: 49
cagctccaga tcgtcattca                                                20

<210> SEQ ID NO 50
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1F2N9

<400> SEQUENCE: 50
gtcattcaga atcgctgcaa                                                20
```

<210> SEQ ID NO 51
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F1F2N10

<400> SEQUENCE: 51
ctcgtggtct ctgagtttgg                                      20

<210> SEQ ID NO 52
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F1F2N9F1F2N10

<400> SEQUENCE: 52
ctggtagacg cccatttcat                                      20

<210> SEQ ID NO 53
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F3F4N1

<400> SEQUENCE: 53
gtcattcaga atcgctgcaa                                      20

<210> SEQ ID NO 54
<211> LENGTH: 21
<212> TYPE: DNA
<213> ORGANISM: Mycobacterium avium
<220> FEATURE:
<221> NAME/KEY: misc_feature
<222> LOCATION: (1)..(21)
<223> OTHER INFORMATION: Primer F3F4N2

<400> SEQUENCE: 54
cgtggtctct gagtttgggt a                                    21

<210> SEQ ID NO 55
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F3F4N1F3F4N2

<400> SEQUENCE: 55
ctggtagacg cccatttcat                                      20

<210> SEQ ID NO 56
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F3F4N3

<400> SEQUENCE: 56
gtcattcaga atcgctgcaa                                       20

<210> SEQ ID NO 57
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F3F4N4

<400> SEQUENCE: 57
tatcgatgaa atgggcgtct                                       20

<210> SEQ ID NO 58
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F3F4N3F3F4N4

<400> SEQUENCE: 58
cagctccaga tcgtcattca                                       20

<210> SEQ ID NO 59
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F3F4N5

<400> SEQUENCE: 59
gtcattcaga atcgctgcaa                                       20

<210> SEQ ID NO 60
<211> LENGTH: 21
<212> TYPE: DNA
<213> ORGANISM: Mycobacterium avium
<220> FEATURE:
<221> NAME/KEY: misc_feature
<222> LOCATION: (1)..(21)
<223> OTHER INFORMATION: Primer F3F4N6

<400> SEQUENCE: 60
ccactcgtgg tctctgagtt t                                     21

<210> SEQ ID NO 61
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F3F4N5F3F4N6

<400> SEQUENCE: 61
ctggtagacg cccatttcat                                       20

<210> SEQ ID NO 62
<211> LENGTH: 20
<212> TYPE: DNA

```
<213> ORGANISM: Mycobacterium avium
<220> FEATURE:
<221> NAME/KEY: misc_feature
<222> LOCATION: (1)..(20)
<223> OTHER INFORMATION: Primer F3F4N7

<400> SEQUENCE: 62
gtcattcaga atcgctgcaa                                              20

<210> SEQ ID NO 63
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F3F4N8

<400> SEQUENCE: 63
atcgatgaaa tgggcgtcta                                              20

<210> SEQ ID NO 64
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F3F4N7F3F4N8

<400> SEQUENCE: 64
cagctccaga tcgtcattca                                              20

<210> SEQ ID NO 65
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F3F4N9

<400> SEQUENCE: 65
gtcattcaga atcgctgcaa                                              20

<210> SEQ ID NO 66
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F3F4N10

<400> SEQUENCE: 66
ctcgtggtct ctgagtttgg                                              20

<210> SEQ ID NO 67
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F3F4N9F3F4N10

<400> SEQUENCE: 67
ctggtagacg cccatttcat                                              20
```

<210> SEQ ID NO 68
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F5F6N1

<400> SEQUENCE: 68
agaatcgctg caatctcagg                                              20

<210> SEQ ID NO 69
<211> LENGTH: 21
<212> TYPE: DNA
<213> ORGANISM: Mycobacterium avium
<220> FEATURE:
<221> NAME/KEY: misc_feature
<222> LOCATION: (1)..(21)
<223> OTHER INFORMATION: Primer F5F6N2

<400> SEQUENCE: 69
cgtggtctct gagtttgggt a                                            21

<210> SEQ ID NO 70
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Probe F5F6N1F5F6N2

<400> SEQUENCE: 70
cgcttgaatg gtcgtctgt                                               19

<210> SEQ ID NO 71
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F5F6N3

<400> SEQUENCE: 71
agaatcgctg caatctcagg                                              20

<210> SEQ ID NO 72
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F5F6N4

<400> SEQUENCE: 72
cttagttcgc cgcttgaatg                                              20

<210> SEQ ID NO 73
<211> LENGTH: 20
<212> TYPE: DNA
<213> ORGANISM: Mycobacterium avium
<220> FEATURE:
<221> NAME/KEY: misc_feature
<222> LOCATION: (1)..(20)

```
<223> OTHER INFORMATION: Probe F5F6N3F5F6N4

<400> SEQUENCE: 73
ctggtagacg cccatttcat                                          20

<210> SEQ ID NO 74
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F5F6N5

<400> SEQUENCE: 74
agaatcgctg caatctcagg                                          20

<210> SEQ ID NO 75
<211> LENGTH: 21
<212> TYPE: DNA
<213> ORGANISM: Mycobacterium avium
<220> FEATURE:
<221> NAME/KEY: misc_feature
<222> LOCATION: (1)..(21)
<223> OTHER INFORMATION: Primer F5F6N6

<400> SEQUENCE: 75
ccactcgtgg tctctgagtt t                                        21

<210> SEQ ID NO 76
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F5F6N5F5F6N6

<400> SEQUENCE: 76
ctggtagacg cccatttcat                                          20

<210> SEQ ID NO 77
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer F5F6N7

<400> SEQUENCE: 77
ctgcaatctc aggcagctc                                           19

<210> SEQ ID NO 78
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F5F6N8

<400> SEQUENCE: 78
cttagttcgc cgcttgaatg                                          20

<210> SEQ ID NO 79
<211> LENGTH: 20
```

```
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F5F6N7F5F6N8

<400> SEQUENCE: 79
ctggtagacg cccatttcat                                                    20

<210> SEQ ID NO 80
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer F5F6N9

<400> SEQUENCE: 80
ctgcaatctc aggcagctc                                                     19

<210> SEQ ID NO 81
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer F5F6N10

<400> SEQUENCE: 81
ttagttcgcc gcttgaatg                                                     19

<210> SEQ ID NO 82
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F5F6N9F5F6N10

<400> SEQUENCE: 82
ctggtagacg cccatttcat                                                    20

<210> SEQ ID NO 83
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F7F8N1

<400> SEQUENCE: 83
cagctccaga tcgtcattca                                                    20

<210> SEQ ID NO 84
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer F7F8N2

<400> SEQUENCE: 84
```
tgtcgatccg cttagttcg                                              19

<210> SEQ ID NO 85
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F7F8N1F7F8N2

<400> SEQUENCE: 85
ctggtagacg cccatttcat                                             20

<210> SEQ ID NO 86
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F7F8N3

<400> SEQUENCE: 86
gcattccaag tcctgaccac                                             20

<210> SEQ ID NO 87
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F7F8N4

<400> SEQUENCE: 87
gtcccaggtg tgttcgagtt                                             20

<210> SEQ ID NO 88
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F7F8N3F7F8N4

<400> SEQUENCE: 88
ctggtagacg cccatttcat                                             20

<210> SEQ ID NO 89
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F7F8N5

<400> SEQUENCE: 89
cagctccaga tcgtcattca                                             20

<210> SEQ ID NO 90
<211> LENGTH: 20
<212> TYPE: DNA
<213> ORGANISM: Mycobacterium avium
<220> FEATURE:
<221> NAME/KEY: misc_feature

```
<222> LOCATION: (1)..(20)
<223> OTHER INFORMATION: Primer F7F8N6

<400> SEQUENCE: 90
ttgtcgatcc gcttagttcg                                               20

<210> SEQ ID NO 91
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F7F8N5F7F8N6

<400> SEQUENCE: 91
ctggtagacg cccatttcat                                               20

<210> SEQ ID NO 92
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F7F8N7

<400> SEQUENCE: 92
agaatcgctg caatctcagg                                               20

<210> SEQ ID NO 93
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer F7F8N8

<400> SEQUENCE: 93
cgcttgaatg gtcgtctgt                                                19

<210> SEQ ID NO 94
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F7F8N7F7F8N8

<400> SEQUENCE: 94
ctggtagacg cccatttcat                                               20

<210> SEQ ID NO 95
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F7F8N9

<400> SEQUENCE: 95
agaatcgctg caatctcagg                                               20

<210> SEQ ID NO 96
```

```
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F7F8N10

<400> SEQUENCE: 96
cttagttcgc cgcttgaatg                                              20

<210> SEQ ID NO 97
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F7F8N9F7F8N10

<400> SEQUENCE: 97
ctggtagacg cccatttcat                                              20

<210> SEQ ID NO 98
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F9F10N1

<400> SEQUENCE: 98
cagctccaga tcgtcattca                                              20

<210> SEQ ID NO 99
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer F9F10N2

<400> SEQUENCE: 99
tgtcgatccg cttagttcg                                               19

<210> SEQ ID NO 100
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F9F10N1F9F10N2

<400> SEQUENCE: 100
ctggtagacg cccatttcat                                              20

<210> SEQ ID NO 101
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F9F10N3

<400> SEQUENCE: 101
```

```
cagctccaga tcgtcattca                                              20
```

<210> SEQ ID NO 102
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F9F10N4

<400> SEQUENCE: 102

```
ttgtcgatcc gcttagttcg                                              20
```

<210> SEQ ID NO 103
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F9F10N3F9F10N4

<400> SEQUENCE: 103

```
ctggtagacg cccatttcat                                              20
```

<210> SEQ ID NO 104
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F9F10N5

<400> SEQUENCE: 104

```
gcattccaag tcctgaccac                                              20
```

<210> SEQ ID NO 105
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F9F10N6

<400> SEQUENCE: 105

```
caggtgtgtt cgagttgcag                                              20
```

<210> SEQ ID NO 106
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F9F10N5F9F10N6

<400> SEQUENCE: 106

```
ctggtagacg cccatttcat                                              20
```

<210> SEQ ID NO 107
<211> LENGTH: 20
<212> TYPE: DNA
<213> ORGANISM: Mycobacterium avium
<220> FEATURE:

-continued

```
<221> NAME/KEY: misc_feature
<222> LOCATION: (1)..(20)
<223> OTHER INFORMATION: Primer F9F10N7

<400> SEQUENCE: 107
gcagctccag atcgtcattc                                                  20

<210> SEQ ID NO 108
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer F9F10N8

<400> SEQUENCE: 108
tgtcgatccg cttagttcg                                                   19

<210> SEQ ID NO 109
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F9F10N7F9F10N8

<400> SEQUENCE: 109
ctggtagacg cccatttcat                                                  20

<210> SEQ ID NO 110
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer F9F10N9

<400> SEQUENCE: 110
cagctccaga tcgtcattca                                                  20

<210> SEQ ID NO 111
<211> LENGTH: 21
<212> TYPE: DNA
<213> ORGANISM: Mycobacterium avium
<220> FEATURE:
<221> NAME/KEY: misc_feature
<222> LOCATION: (1)..(21)
<223> OTHER INFORMATION: Primer F9F10N10

<400> SEQUENCE: 111
tgagaattgt cgatccgctt a                                                21

<210> SEQ ID NO 112
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe F9F10N9F9F10N10

<400> SEQUENCE: 112
ctggtagacg cccatttcat                                                  20
```

```
<210> SEQ ID NO 113
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M1M2N1

<400> SEQUENCE: 113
ggcagcatgc tcaagtagc                                             19

<210> SEQ ID NO 114
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M1M2N2

<400> SEQUENCE: 114
gggttcgaat cccgtagg                                              18

<210> SEQ ID NO 115
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M1M2N1M1M2N2

<400> SEQUENCE: 115
taccgactga gctacctggc                                            20

<210> SEQ ID NO 116
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M1M2N3

<400> SEQUENCE: 116
gcagcatgct caagtagcc                                             19

<210> SEQ ID NO 117
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M1M2N4

<400> SEQUENCE: 117
gggttcgaat cccgtagg                                              18

<210> SEQ ID NO 118
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M1M2N3M1M2N4
```

<400> SEQUENCE: 118
taccgactga gctacctggc                                               20

<210> SEQ ID NO 119
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M1M2N5

<400> SEQUENCE: 119
gcagcatgct caagtagcc                                                19

<210> SEQ ID NO 120
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M1M2N6

<400> SEQUENCE: 120
ccctttcaag gcggtagc                                                 18

<210> SEQ ID NO 121
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M1M2N5M1M2N6

<400> SEQUENCE: 121
taccgactga gctacctggc                                               20

<210> SEQ ID NO 122
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M1M2N7

<400> SEQUENCE: 122
gcagcatgct caagtagcc                                                19

<210> SEQ ID NO 123
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M1M2N8

<400> SEQUENCE: 123
gccctttcaa ggcggtag                                                 18

<210> SEQ ID NO 124
<211> LENGTH: 20
<212> TYPE: DNA
<213> ORGANISM: Mycobacterium avium

```
<220> FEATURE:
<221> NAME/KEY: misc_feature
<222> LOCATION: (1)..(20)
<223> OTHER INFORMATION: Probe M1M2N7M1M2N8

<400> SEQUENCE: 124
taccgactga gctacctggc                                                    20

<210> SEQ ID NO 125
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M1M2N9

<400> SEQUENCE: 125
ggcagcatgc tcaagtagc                                                     19

<210> SEQ ID NO 126
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M1M2N10

<400> SEQUENCE: 126
ccctttcaag gcggtagc                                                      18

<210> SEQ ID NO 127
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M1M2N9M1M2N10

<400> SEQUENCE: 127
taccgactga gctacctggc                                                    20

<210> SEQ ID NO 128
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M3M4N1

<400> SEQUENCE: 128
ggcagcatgc tcaagtagc                                                     19

<210> SEQ ID NO 129
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M3M4N2

<400> SEQUENCE: 129
gggttcgaat cccgtagg                                                      18
```

```
<210> SEQ ID NO 130
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M3M4N1M3M4N2

<400> SEQUENCE: 130
taccgactga gctacctggc                                               20

<210> SEQ ID NO 131
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M3M4N3

<400> SEQUENCE: 131
gcagcatgct caagtagcc                                                19

<210> SEQ ID NO 132
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M3M4N4

<400> SEQUENCE: 132
gggttcgaat cccgtagg                                                 18

<210> SEQ ID NO 133
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M3M4N3M3M4N4

<400> SEQUENCE: 133
taccgactga gctacctggc                                               20

<210> SEQ ID NO 134
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M3M4N5

<400> SEQUENCE: 134
gcagcatgct caagtagcc                                                19

<210> SEQ ID NO 135
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M3M4N6
```

<400> SEQUENCE: 135
ccctttcaag gcggtagc                                                    18

<210> SEQ ID NO 136
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M3M4N5M3M4N6

<400> SEQUENCE: 136
taccgactga gctacctggc                                                  20

<210> SEQ ID NO 137
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M3M4N7

<400> SEQUENCE: 137
gcagcatgct caagtagcc                                                   19

<210> SEQ ID NO 138
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M3M4N8

<400> SEQUENCE: 138
gccctttcaa ggcggtag                                                    18

<210> SEQ ID NO 139
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M3M4N7M3M4N8

<400> SEQUENCE: 139
taccgactga gctacctggc                                                  20

<210> SEQ ID NO 140
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M3M4N9

<400> SEQUENCE: 140
ggcagcatgc tcaagtagc                                                   19

<210> SEQ ID NO 141
<211> LENGTH: 18
<212> TYPE: DNA

```
<213> ORGANISM: Mycobacterium avium
<220> FEATURE:
<221> NAME/KEY: misc_feature
<222> LOCATION: (1)..(18)
<223> OTHER INFORMATION: Primer M3M4N10

<400> SEQUENCE: 141
ccctttcaag gcggtagc                                                 18

<210> SEQ ID NO 142
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M3M4N9M3M4N10

<400> SEQUENCE: 142
taccgactga gctacctggc                                               20

<210> SEQ ID NO 143
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M5M6N1

<400> SEQUENCE: 143
ggcagcatgc tcaagtagc                                                19

<210> SEQ ID NO 144
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M5M6N2

<400> SEQUENCE: 144
ctgtggcgca gttggttag                                                19

<210> SEQ ID NO 145
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M5M6N1M5M6N2

<400> SEQUENCE: 145
taccgactga gctacctggc                                               20

<210> SEQ ID NO 146
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M5M6N3

<400> SEQUENCE: 146
gcagcatgct caagtagcc                                                19
```

<210> SEQ ID NO 147
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M5M6N4

<400> SEQUENCE: 147
ctgtggcgca gttggttag 19

<210> SEQ ID NO 148
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M5M6N3M5M6N4

<400> SEQUENCE: 148
taccgactga gctacctggc 20

<210> SEQ ID NO 149
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M5M6N5

<400> SEQUENCE: 149
cggcagcatg ctcaagtag 19

<210> SEQ ID NO 150
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M5M6N6

<400> SEQUENCE: 150
ctgtggcgca gttggttag 19

<210> SEQ ID NO 151
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M5M6N5M5M6N6

<400> SEQUENCE: 151
taccgactga gctacctggc 20

<210> SEQ ID NO 152
<211> LENGTH: 18
<212> TYPE: DNA
<213> ORGANISM: Mycobacterium avium
<220> FEATURE:
<221> NAME/KEY: misc_feature
<222> LOCATION: (1)..(18)

<223> OTHER INFORMATION: Primer M5M6N7

<400> SEQUENCE: 152
cggcagcatg ctcaagta                                                     18

<210> SEQ ID NO 153
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M5M6N8

<400> SEQUENCE: 153
ctgtggcgca gttggttag                                                    19

<210> SEQ ID NO 154
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M5M6N7M5M6N8

<400> SEQUENCE: 154
taccgactga gctacctggc                                                   20

<210> SEQ ID NO 155
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M5M6N9

<400> SEQUENCE: 155
ggcagcatgc tcaagtagc                                                    19

<210> SEQ ID NO 156
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M5M6N10

<400> SEQUENCE: 156
gtggcgcagt tggttagc                                                     18

<210> SEQ ID NO 157
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M5M6N9M5M6N10

<400> SEQUENCE: 157
taccgactga gctacctggc                                                   20

<210> SEQ ID NO 158
<211> LENGTH: 19

```
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M7M8N1

<400> SEQUENCE: 158
ggcagcatgc tcaagtagc                                              19

<210> SEQ ID NO 159
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M7M8N2

<400> SEQUENCE: 159
gggttcgaat cccgtagg                                               18

<210> SEQ ID NO 160
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M7M8N1M7M8N2

<400> SEQUENCE: 160
taccgactga gctacctggc                                             20

<210> SEQ ID NO 161
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M7M8N3

<400> SEQUENCE: 161
gcagcatgct caagtagcc                                              19

<210> SEQ ID NO 162
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M7M8N4

<400> SEQUENCE: 162
gggttcgaat cccgtagg                                               18

<210> SEQ ID NO 163
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M7M8N3M7M8N4

<400> SEQUENCE: 163
```
taccgactga gctacctggc                                              20

<210> SEQ ID NO 164
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M7M8N5

<400> SEQUENCE: 164
gcagcatgct caagtagcc                                               19

<210> SEQ ID NO 165
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M7M8N6

<400> SEQUENCE: 165
ccctttcaag gcggtagc                                                18

<210> SEQ ID NO 166
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M7M8N5M7M8N6

<400> SEQUENCE: 166
taccgactga gctacctggc                                              20

<210> SEQ ID NO 167
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M7M8N7

<400> SEQUENCE: 167
gcagcatgct caagtagcc                                               19

<210> SEQ ID NO 168
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M7M8N8

<400> SEQUENCE: 168
gccctttcaa ggcggtag                                                18

<210> SEQ ID NO 169
<211> LENGTH: 20
<212> TYPE: DNA
<213> ORGANISM: Mycobacterium avium
<220> FEATURE:
<221> NAME/KEY: misc_feature

```
<222> LOCATION: (1)..(20)
<223> OTHER INFORMATION: Probe M7M8N7M7M8N8

<400> SEQUENCE: 169
taccgactga gctacctggc                                                 20

<210> SEQ ID NO 170
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M7M8N9

<400> SEQUENCE: 170
ggcagcatgc tcaagtagc                                                  19

<210> SEQ ID NO 171
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M7M8N10

<400> SEQUENCE: 171
ccctttcaag gcggtagc                                                   18

<210> SEQ ID NO 172
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M7M8N9M7M8N10

<400> SEQUENCE: 172
taccgactga gctacctggc                                                 20

<210> SEQ ID NO 173
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M9M10N1

<400> SEQUENCE: 173
gcagcatgct caagtagcc                                                  19

<210> SEQ ID NO 174
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M9M10N2

<400> SEQUENCE: 174
aatcccgtag ggggtacg                                                   18

<210> SEQ ID NO 175
```

```
<210> SEQ ID NO 175
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M9M10N1M9M10N2

<400> SEQUENCE: 175
taccgactga gctacctggc                                                 20

<210> SEQ ID NO 176
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M9M10N3

<400> SEQUENCE: 176
ggcagcatgc tcaagtagc                                                  19

<210> SEQ ID NO 177
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer M9M10N4

<400> SEQUENCE: 177
aatcccgtag ggggtacg                                                   18

<210> SEQ ID NO 178
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M9M10N3M9M10N4

<400> SEQUENCE: 178
taccgactga gctacctggc                                                 20

<210> SEQ ID NO 179
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M9M10N5

<400> SEQUENCE: 179
gcagcatgct caagtagcc                                                  19

<210> SEQ ID NO 180
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M9M10N6

<400> SEQUENCE: 180
```

```
gaatcccgta gggggtacg                                                  19

<210> SEQ ID NO 181
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M9M10N5M9M10N6

<400> SEQUENCE: 181
taccgactga gctacctggc                                                 20

<210> SEQ ID NO 182
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M9M10N7

<400> SEQUENCE: 182
ggcagcatgc tcaagtagc                                                  19

<210> SEQ ID NO 183
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M9M10N8

<400> SEQUENCE: 183
gaatcccgta gggggtacg                                                  19

<210> SEQ ID NO 184
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M9M10N7M9M10N8

<400> SEQUENCE: 184
taccgactga gctacctggc                                                 20

<210> SEQ ID NO 185
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer M9M10N9

<400> SEQUENCE: 185
gcagcatgct caagtagcc                                                  19

<210> SEQ ID NO 186
<211> LENGTH: 18
<212> TYPE: DNA
<213> ORGANISM: Mycobacterium avium
<220> FEATURE:
```

```
<221> NAME/KEY: misc_feature
<222> LOCATION: (1)..(18)
<223> OTHER INFORMATION: Primer M9M10N10

<400> SEQUENCE: 186 ggggttcgaat cccgtagg                                                  18

<210> SEQ ID NO 187
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe M9M10N9M9M10N10

<400> SEQUENCE: 187
taccgactga gctacctggc                                                 20

<210> SEQ ID NO 188
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer P901

<400> SEQUENCE: 188
ggcacggctc ttgttgtagt                                                 20

<210> SEQ ID NO 189
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer P902

<400> SEQUENCE: 189
gcgctgctgg agttgatt                                                   18

<210> SEQ ID NO 190
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe P901P902

<400> SEQUENCE: 190
gaatataaag cagccgctgc                                                 20

<210> SEQ ID NO 191
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer P901A

<400> SEQUENCE: 191
cacggctctt gttgtagtcg                                                 20
```

```
<210> SEQ ID NO 192
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer P902A

<400> SEQUENCE: 192
gcgctgctgg agttgatt                                                 18

<210> SEQ ID NO 193
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe P901AP902A

<400> SEQUENCE: 193
gaatataaag cagccgctgc                                               20

<210> SEQ ID NO 194
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer P901B

<400> SEQUENCE: 194
cggctcttgt tgtagtcgaa                                               20

<210> SEQ ID NO 195
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer P902B

<400> SEQUENCE: 195
gcgctgctgg agttgatt                                                 18

<210> SEQ ID NO 196
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe P901BP902B

<400> SEQUENCE: 196
gaatataaag cagccgctgc                                               20

<210> SEQ ID NO 197
<211> LENGTH: 21
<212> TYPE: DNA
<213> ORGANISM: Mycobacterium avium
<220> FEATURE:
<221> NAME/KEY: misc_feature
<222> LOCATION: (1)..(21)
<223> OTHER INFORMATION: Primer P901C
```

<400> SEQUENCE: 197
cggctcttgt tgtagtcgaa g                                              21

<210> SEQ ID NO 198
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer P902C

<400> SEQUENCE: 198
gcgctgctgg agttgatt                                                  18

<210> SEQ ID NO 199
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe P901CP902C

<400> SEQUENCE: 199
gaatataaag cagccgctgc                                                20

<210> SEQ ID NO 200
<211> LENGTH: 21
<212> TYPE: DNA
<213> ORGANISM: Mycobacterium avium
<220> FEATURE:
<221> NAME/KEY: misc_feature
<222> LOCATION: (1)..(21)
<223> OTHER INFORMATION: Primer P901D

<400> SEQUENCE: 200
acggctcttg ttgtagtcga a                                              21

<210> SEQ ID NO 201
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer P902D

<400> SEQUENCE: 201
gcgctgctgg agttgatt                                                  18

<210> SEQ ID NO 202
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Probe P901DP902D

<400> SEQUENCE: 202
gaatataaag cagccgctgc                                                20

<210> SEQ ID NO 203
<211> LENGTH: 19
<212> TYPE: DNA
<213> ORGANISM: Mycobacterium avium

```
<220> FEATURE:
<221> NAME/KEY: misc_feature
<222> LOCATION: (1)..(19)
<223> OTHER INFORMATION: Primer P901N

<400> SEQUENCE: 203
gttccagcgc cgaaagtat                                                19

<210> SEQ ID NO 204
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer P902N

<400> SEQUENCE: 204
caagaccgac gccaaagac                                                19

<210> SEQ ID NO 205
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer P901AN

<400> SEQUENCE: 205
gttccagcgc cgaaagtat                                                19

<210> SEQ ID NO 206
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer P902AN

<400> SEQUENCE: 206
caagaccgac gccaaaga                                                 18

<210> SEQ ID NO 207
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer P901BN

<400> SEQUENCE: 207
gttccagcgc cgaaagtatt                                               20

<210> SEQ ID NO 208
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer P902BN

<400> SEQUENCE: 208
caagaccgac gccaaagac                                                19
```

<210> SEQ ID NO 209
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer P901CN

<400> SEQUENCE: 209
agcgccgaaa gtattccag                                                19

<210> SEQ ID NO 210
<211> LENGTH: 19
<212> TYPE: DNA
<213> ORGANISM: Mycobacterium avium
<220> FEATURE:
<221> NAME/KEY: misc_feature
<222> LOCATION: (1)..(19)
<223> OTHER INFORMATION: Primer P902CN

<400> SEQUENCE: 210
caagaccgac gccaaagac                                                19

<210> SEQ ID NO 211
<211> LENGTH: 20
<212> TYPE: DNA
<213> ORGANISM: Mycobacterium avium
<220> FEATURE:
<221> NAME/KEY: misc_feature
<222> LOCATION: (1)..(20)
<223> OTHER INFORMATION: Primer P901DN

<400> SEQUENCE: 211
gttccagcgc cgaaagtatt                                               20

<210> SEQ ID NO 212
<211> LENGTH: 18
<212> TYPE: DNA
<213> ORGANISM: Mycobacterium avium
<220> FEATURE:
<221> NAME/KEY: misc_feature
<222> LOCATION: (1)..(18)
<223> OTHER INFORMATION: Primer P902DN

<400> SEQUENCE: 212
caagaccgac gccaaaga                                                 18

<210> SEQ ID NO 213
<211> LENGTH: 620
<212> TYPE: DNA
<213> ORGANISM: Mycobacterium avium
<220> FEATURE:
<221> NAME/KEY: misc_feature
<222> LOCATION: (1)..(620)
<223> OTHER INFORMATION: Mycobacterium avium subspecies M.
      Paratuberculosis species specific F57 DNA fragment

<400> SEQUENCE: 213
ggatctcggc cccgatagct ttcctctcct tcgtcaccaa ctggcgcggg tccaggaacg    60
cttggcactc gtcaatcacc acgaacacca gcggaacctg cggcgtcggg ccgcgatccc   120
aaaagttgga cgatccgaat atgttgttgc cctgtctaat tcgatcacgg actagaccgg   180
tcgcgtcatt cagaatcgct gcaatctcag gcagctccag atcgtcattc atgaatcggc   240
agctacgagc acgcaggcat tccaagtcct gaccaccctt cccgtcgatg acagcgaact   300

-continued

```
ggaccgccgc tgacgcaccg aacgacccca gagcactcgt cagccacgcg gttttccccg    360
accctggtac gcctcccact acaacgcccg atacgttcgc caacgggagc gactggtaga    420
cgcccatttc atcgataccc aaactcagag accacgagtg ggcggctggc acagacgacc    480
attcaagcgg cgaactaagc ggatcgacaa ttctcagctg caactcgaac acacctggga    540
ccggctcggt gacaacaaca ttcggtacac caatagctga cgccagcttc ggagccgcca    600
cctgccactg tctgagatcc                                                620

<210> SEQ ID NO 214
<211> LENGTH: 1317
<212> TYPE: DNA
<213> ORGANISM: Mycobacterium avium

<400> SEQUENCE: 214
tcgcgtgagg ctctgtggtg aaacgaccaa ggatcactac cgagaggaac atcgcgatgg     60
ccctggatca gtctgccttg ctggaggtgc tggacgcatt acgcaatgcc gatgccgctg    120
atcggatcaa gcaggccgcc gagacgattt atcaggcact catcgatgcg gagctgacgg    180
cggtgatcgg cgccggtccg catgaacgga gcgcatcacg aaccaaccag cgcaatgggt    240
ctcggccgcg cacactgtcg acgatcgctg gcgatttgga gttgcggatt cccaagcttc    300
ggtcgggctc gttcttcccg gcgctgctgg agcggcgccg ccgggtcgat cagtgcttgt    360
tcgcggtggt gatggaggcc tatttgcacg gcacctccac ccgcaaagtc gacgatttgg    420
ttaaagccct cggcgcggac gccggcatct ccaaaagcga ggtctcccgg atttgcgccg    480
atctggacac cgaggtaggc gccttcgggg accggcctct atccgagcag cacttcccgt    540
atgtgttcct cgacgccact tactgcaagg ctcgggtcaa ccatcgggtg gtctcccaag    600
cggtcgtcat cgccaccggt gtcgcggttg acggacgccg tgaagtgctc ggcttcgacg    660
tcggtgactc cgaggacggc gcgttttgga cggcgtttct gcgctcactg aaaacccgcg    720
gcctgtccgg ggtgcagctg gtgatctctg atgcccacac cgggttgcgc agcgccatcg    780
aggccatcct catcggcgca tcttggcaac gatgccgggt gcacttcctg cgcaacgtgc    840
tcgcccaggt gcccaaggga tcagccgaga tggtcgccgc agcgatccgc accatcttcg    900
cccaacccga cgccgaacat gtgcgagagc aactcgacac catcgccggc atgctcggcc    960
gccaactgcc caaggtcgaa acgatgctgc gcgaggccgc cgacgacatc accgcattcg   1020
ccgatttccc tgtcctgcac tggaaaaaga tctggagcac caacccctc gaacgactca   1080 acaaggagat caaacgccgc accgacgtcg tcggcgtctt ccccaacccc gccgcgctgc   1140
tacggctggc cggctccgtt ctcgtcgaag cccacgacga atggcaagtc gccgaaaagc   1200
gctatctctc cgagaccacc ctggccctat tacatccccg ctccgattca gccgaccaat   1260
ccgttgccgt ccccgccgcc atcacggcat agtggaaact cgcagagcct caggcga     1317
```